US012564610B2

(12) United States Patent
Vasudevan

(10) Patent No.: US 12,564,610 B2
(45) Date of Patent: Mar. 3, 2026

(54) HUMAN PERIVENTRICULAR ENDOTHELIAL CELL THERAPY FOR NEUROPSYCHIATRIC DISORDERS

(71) Applicant: The McLean Hospital Corporation, Belmont, MA (US)

(72) Inventor: Anju Vasudevan, Waltham, MA (US)

(73) Assignee: The McLean Hospital Corporation, Belmont, MA (US)

( * ) Notice: Subject to any disclaimer, the term of this patent is extended or adjusted under 35 U.S.C. 154(b) by 814 days.

(21) Appl. No.: 17/769,647

(22) PCT Filed: Oct. 19, 2020

(86) PCT No.: PCT/US2020/056366
§ 371 (c)(1),
(2) Date: Apr. 15, 2022

(87) PCT Pub. No.: WO2021/077105
PCT Pub. Date: Apr. 22, 2021

(65) Prior Publication Data
US 2024/0058388 A1     Feb. 22, 2024

Related U.S. Application Data

(60) Provisional application No. 62/923,512, filed on Oct. 19, 2019.

(51) Int. Cl.
*A61K 35/30*     (2015.01)
*A61P 25/24*     (2006.01)
*C12N 5/071*     (2010.01)

(52) U.S. Cl.
CPC .............. *A61K 35/30* (2013.01); *A61P 25/24* (2018.01); *C12N 5/069* (2013.01); *C12N 2501/115* (2013.01); *C12N 2501/165* (2013.01); *C12N 2501/415* (2013.01); *C12N 2501/999* (2013.01); *C12N 2506/02* (2013.01)

(58) Field of Classification Search
None
See application file for complete search history.

(56) References Cited

U.S. PATENT DOCUMENTS

| | | |
|---|---|---|
| 2012/0015395 A1 | 1/2012 | Shusta et al. |
| 2016/0298089 A1 | 10/2016 | Kim et al. |
| 2017/0283772 A1 | 10/2017 | Qian et al. |
| 2017/0362584 A1 | 12/2017 | Bani et al. |
| 2018/0171291 A1 | 6/2018 | Gerecht et al. |

FOREIGN PATENT DOCUMENTS

WO     WO 2019/058140     3/2019

OTHER PUBLICATIONS

Li et al (Cell Research (2018) 28:221-248. doi:10.1038/cr.2017.135; published online Oct. 31, 2017) (Year: 2017).*

Vissapragada et al., "Bidirectional crosstalk between periventricular endothelial cells and neural progenitor cells promotes the formation of a neurovascular unit," Brain Res., May 2014, 1565:8-17.

Alvarez-Dolado and Broccoli, "GABAergic neuronal precursor grafting: implications in brain regeneration and plasticity," Neural plasticity, Jun. 2011, 2011:384216, 11 pages.

Alvarez-Dolado et al., "Cortical inhibition modified by embryonic neural precursors grafted into the postnatal brain," J Neurosci, Jul. 2006, 26(28):7380-7389.

Appelt-Menzel et al., "Establishment of a human blood-brain barrier co-culture model mimicking the neurovascular unit using induced pluri- and multipotent stem cells," Stem Cell Reports, Apr. 2017, 8(4):894-906.

Ardhanareeswaran et al., "Human induced pluripotent stem cells for modelling neurodevelopmental disorders," Nat Rev Neurol., May 2017, 13(5):265-278, 14 pages.

Bellin et al., "Induced pluripotent stem cells: the new patient?," Nat Rev Mol Cell Biol., Nov. 2012, 13(11):713-726, 14 pages.

Brennand et al., "Modelling schizophrenia using human induced pluripotent stem cells," Nature, May 2011, 473(7346):221-225, 7 pages.

Can et al., "The tail suspension test," J Vis Exp, Jan. 2012, 59:e3769, 6 pages.

Castiglioni et al., "Induced pluripotent stem cell lines from Huntington's disease mice undergo neuronal differentiation while showing alterations in the lysosomal pathway," Neurobiology of disease, Apr. 2012, 46(1):30-40.

Corbin et al., "Telencephalic cells take a tangent: non-radial migration in the mammalian forebrain," Nat Neurosci, Nov. 2001, 4 Suppl:1177-1182.

Cunningham et al., "hPSC-derived maturing GABAergic interneurons ameliorate seizures and abnormal behavior in epileptic mice," Cell Stem Cell, Nov. 2014, 15(5):559-573.

Datta et al., "Human Forebrain Endothelial Cell Therapy for Psychiatric Disorders," Mol Psychiatry, Sep. 2021, 26(9):4864-4883.

Egawa et al., "Drug screening for ALS using patient-specific induced pluripotent stem cells," Sci Transl Med, Aug. 2012, 4(145):145ra104, 9 pages.

Garitaonandia et al., "Novel Approach to Stem Cell Therapy in Parkinson's Disease," Stem Cells Dev., Jul. 2018, 27(14):951-957, 20 pages.

(Continued)

*Primary Examiner* — Peter Paras, Jr.
*Assistant Examiner* — Khoa Nhat Tran
(74) *Attorney, Agent, or Firm* — Fish & Richardson P.C.

(57)     ABSTRACT

Described herein are methods for generating human forebrain endothelial cells, compositions comprising the cells, and methods of use thereof in therapy. Provided herein are methods for generation of human embryonic forebrain-like endothelial cells (e.g., periventricular endothelial cells) from human embryonic stem cells; the methods include addition or GABA and WNT7A for efficient differentiation, and isolation of GABRB37CD31+ cell population by FACS.

14 Claims, 29 Drawing Sheets

(56)                References Cited

OTHER PUBLICATIONS

Giandomenico and Lancaster, "Probing human brain evolution and development in organoids," Curr. Opin. Cell Biol., Feb. 2017, 44:36-43.

Hess et al., "Home improvement: C57BL/6J mice given more naturalistic nesting materials build better nests," J Am Assoc Lab Anim Sci, Nov. 2008, 47(6):25-31.

Hunt and Baraban, "Interneuron Transplantation as a Treatment for Epilepsy," Cold Spring Harb Perspect Med, Dec. 2015, 5(12):a022376, 14 pages.

International Preliminary Report on Patentability in International Appln. No. PCT/US2020/056366, dated Apr. 19, 2022, 7 pages.

International Search Report and Written Opinion in International Appln. No. PCT/US2020/056366, dated Jan. 26, 2021, 10 pages.

Jiao et al., "DAVID-WS: a stateful web service to facilitate gene/protein list analysis," Bioinformatics, 2012, 28(13):1805-1806.

Kelava et al. "Dishing out mini-brains: Current progress and future prospects in brain organoid research," Dev. Biol., 2016, 420(2):199-209.

Kikuchi et al., "Human iPSR cell-derived dopaminergic neurons function in a primate Parkinson's disease model," Nature, Aug. 2017, 548(7669):592-596.

Kim et al., "Efficient Specification of Interneurons from Human Pluripotent Stem Cells by Dorsoventral and Rostrocaudal Modulation," Stem Cells, 2014, 32(7):1789-1804.

Kumar et al. "Isolation and culture of endothelial cells from the embryonic forebrain," J Vis Exp, Jan. 2014, 83:e51021, 8 pages.

Lancaster et al., "Cerebral organoids model human brain development and microcephaly," Nature, 2013, 501(7467):373-379.

Lassiter et al., "Embryonic stem cell-derived neural progenitors transplanted to the hippocampus migrate on host vasculature," Stem Cell Res., 2016, 16(3):579-588.

Lee et al., "Large-scale screening using familial dysautonomia induced pluripotent stem cells identifies compounds that rescue IKBKAP expression," Nat Biotechnol., 2012, 30(12):1244-1248.

Levitt et al., "Regulation of neocortical interneuron development and the implications for neurodevelopmental disorders," Trends Neurosci., 2004, 27(7):400-406.

Lewis et al., "Schizophrenia as a disorder of neurodevelopment," Annu Rev Neurosci., 2002, 25(1):409-432.

Lewis et al.. , "Cortical inhibitory neurons and schizophrenia," Nat Rev Neurosci., Apr. 2005, 6(4):312-324.

Li et al., "Development of human in vitro brain-blood barrier model from induced pluripotent stem cell-derived endothelial cells to predict the in vivo permeability of drugs," Neurosci Bull., 2019, 15 pages.

Li et al., "Endothelial cell-derived GABA signaling modulates neuronal migration and postnatal behavior," Cell Research, 2018, 28:221-48, 28 pages.

Li et al., "Endothelial VEGF Sculpts Cortical Cytoarchitecture," J Neurosci, Sep. 2013, 33(37):14809-15.

Lippmann et al., "Defined Human Pluripotent Stem Cell Culture Enables Highly Efficient Neuroepithelium Derivation Without Small Molecule Inhibitors," Stem Cells, 2014, 32(4):1032-1042.

Lippmann et al., "Derivation of blood-brain barrier endothelial cells from human pluripotent stem cells," Nat Biotechnol., Aug. 2012, 30(8):783-791.

Liu et al., "Medial ganglionic eminence-like cells derived from human embryonic stem cells correct learning and memory deficits," Nat Biotechnol., 2013, 31(5):440-447.

Livak et al., "Analysis of relative gene expression data using real-time quantitative PCR and the 2(-Delta Delta C(T)) Method," Methods, 2001, 25(4):402-408.

Mansour et al., "An in vivo model of functional and vascularized human brain organoids," Nat Biotechnol., 2018, 36(5):432-441.

Marin et al., "A long, remarkable journey: tangential migration in the telencephalon," Nat Rev Neurosci., 2001, 2(11):780-790.

Marin, "Interneuron dysfunction in psychiatric disorders," Nat Rev Neurosci., 2012, 13(2):107-120.

Maroof et al. "Directed differentiation and functional maturation of cortical interneurons from human embryonic stem cells," Cell Stem Cell, May 2013, 12(5):559-572.

Matsui et al., "Regeneration of the damaged central nervous system through reprogramming technology: Basic concepts and potential application for cell replacement therapy," Exp Neurol., 2014, 260:12-18.

Morizane et al., "MHC matching improves engraftment of iPSC-derived neurons in non-human primates," Nature Communications, 2017 8:385, 12 pages.

Moy et al. "Sociability and preference for social novelty in five inbred strains: an approach to assess autistic-like behavior in mice," Genes Brain Behav., 2004, 3:287-302.

Nicholas et al., "Functional maturation of hPSC-derived forebrain interneurons requires an extended timeline and mimics human neural development," Cell Stem Cell, May 2013, 12(5):573-586.

Nolte et al., "Benefits and risks of intranigral transplantation of GABA-producing cells subsequent to the establishment of kindling-induced seizures," Neurobiology of Disease, 2008, 31(3):342-354.

Parent et al., "Reprogramming patient-derived cells to study the epilepsies," Nat Neurosci., 2015, 18(3):360-366.

Paşca et al., "Functional cortical neurons and astrocytes from human pluripotent stem cells in 3D Culture," Nat. Methods, 2015, 12(7):671-678.

Renner et al., "Self-organized developmental patterning and differentiation in cerebral organoids," EMBO J., 2017, 36(10):1316-1329.

Ribecco-Lutkiewicz et al., "A novel human induced pluripotent stem cell blood-brain barrier model: Applicability to study antibody-triggered receptor-mediated transcytosis," Sci Rep., 2018, 8(1):1873, 17 pages.

Ritchie et al., "limma powers differential expression analyses for RNA-sequencing and microarray studies," Nucleic Acids Res., 2015, 43(7):e47, 13 pages.

Schwarz et al., "Human pluripotent stem cell-derived neural constructs for predicting neural toxicity," Proc. Natl. Acad. Sci. USA, 2015, 112(40):12516-12521.

Shetty et al., "Potential of GABA-ergic cell therapy for schizophrenia, neuropathic pain, and Alzheimer's and Parkinson's diseases," Brain Res., 2016, 1638:74-87.

Silverman et al., "Repetitive self-grooming behavior in the BTBR mouse model of autism is blocked by the mGluR5 antagonist MPEP," Neuropsychopharmacology, 2010, 35(4):976-989.

Song et al., "Human autologous iPSC-derived dopaminergic progenitors restore motor function in Parkinson's disease models," J Clin Invest., 2020, 130(2):904-920.

Sonntag et al., "Pluripotent Stem Cell-based therapy for Parkinson's disease: current status and future prospects," Prog Neurobiol., Sep. 2018, 168:1-20.

Southwell et al., "Interneurons from embryonic development to cell-based therapy," Science, Apr. 2014, 344(6180):1240622-0-1240622-8, 10 pages.

Spatazza et al., "Transplantation of GABAergic interneurons for cell-based therapy," Prog Brain Res., 2017, 231:57-85.

Tabar et al., "Pluripotent stem cells in regenerative medicine: challenges and recent progress," Nat Rev Genet., Feb. 2014, 15(2):82-92.

Takao et al., "Light/dark transition test for mice," J Vis Exp., 2006, 2 pages.

Treiman, "GABAergic mechanisms in epilepsy," Epilepsia, 2001, 42, Suppl 3: 8-12.

Tyson and Anderson, "GABAergic interneuron transplants to study development and treat disease," Trends Neurosci 2014; 37: 169-177.

Upadhya et al., "Human induced pluripotent stem cell-derived MGE cell grafting after status epilepticus attenuates chronic epilepsy and comorbidities via synaptic integration," Proc Natl Acad Sci USA, 2019, 116:287-296.

Vasudevan et al., "Compartment-specific transcription factors orchestrate angiogenesis gradients in the embryonic brain," Nat Neurosci., 2008, 11(4):429-439.

(56) References Cited

OTHER PUBLICATIONS

Wichterle et al., "Young neurons from medial ganglionic eminence disperse in adult and embryonic brain," Nat Neurosci., 1999, 2(5):461-466.

Won et al., "Autonomous Vascular Networks Synchronize GABA Neuron Migration in the Embryonic Forebrain," Nat Commun, 2013, 4:2149, 14 pages.

Wonders et al., "The origin and specification of cortical interneurons," Nat Rev Neurosci., 2006, 7(9)687-696.

Yin et al., "Engineering Stem Cell Organoids," Cell Stem Cell, 2016, 18(1):25-38.

Zhu et al., "Cortical GABAergic Interneuron/Progenitor Transplantation as a Novel Therapy for Intractable Epilepsy," Front Cell Neurosci., 2018, 12(167):1-9.

* cited by examiner

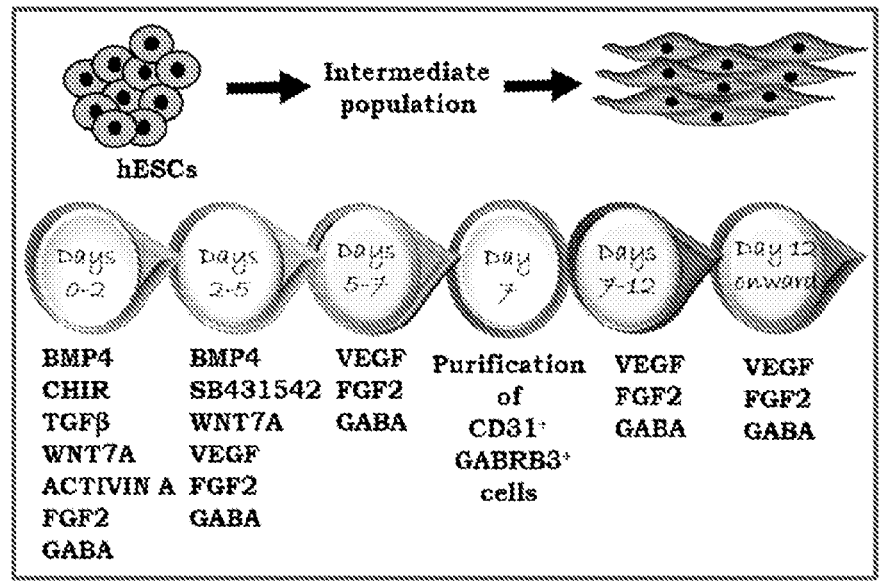
*FIG. 1A*
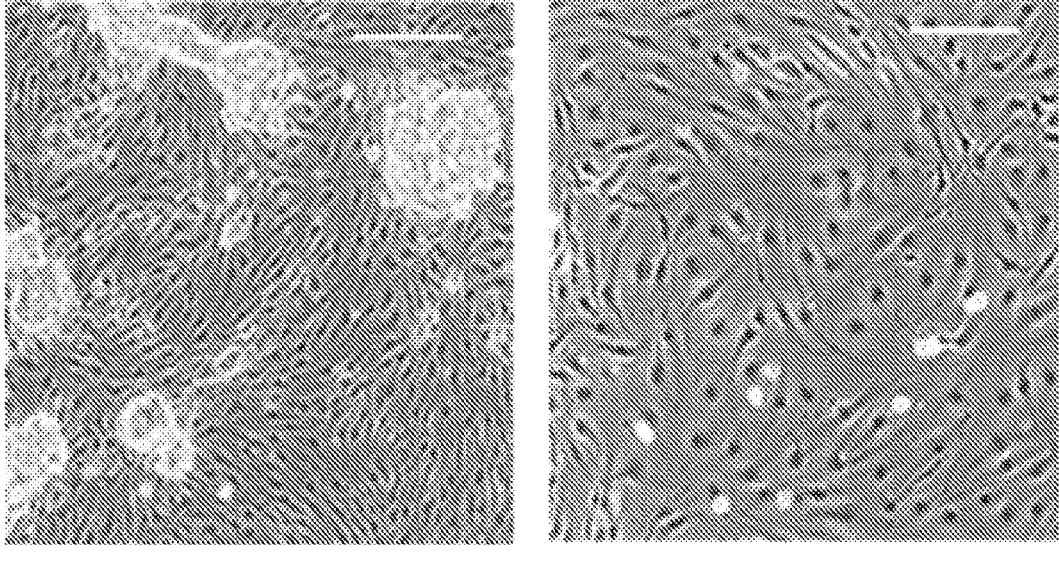
*FIG. 1B*                    *FIG. 1C*

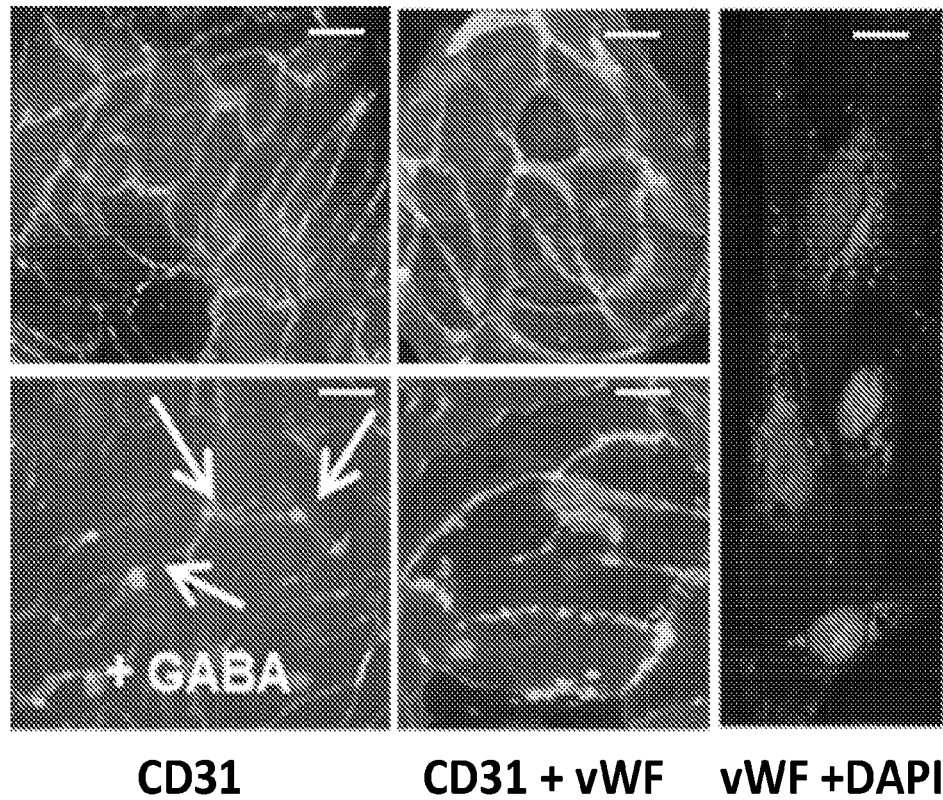
CD31      CD31 + vWF      vWF +DAPI
*FIG. 1D*          *FIG. 1E*          *FIG. 1F*

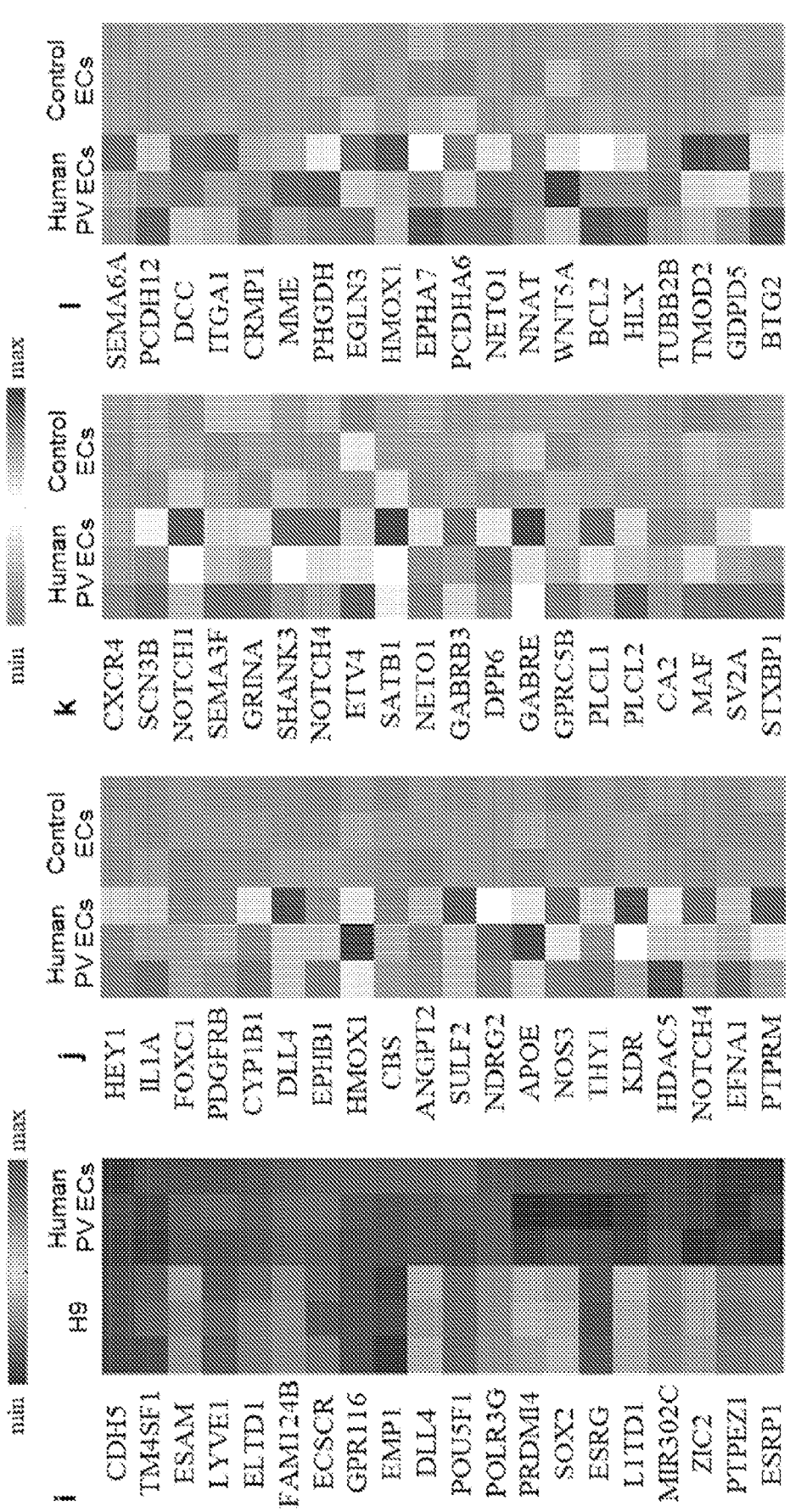
*FIGs. 1I-L*

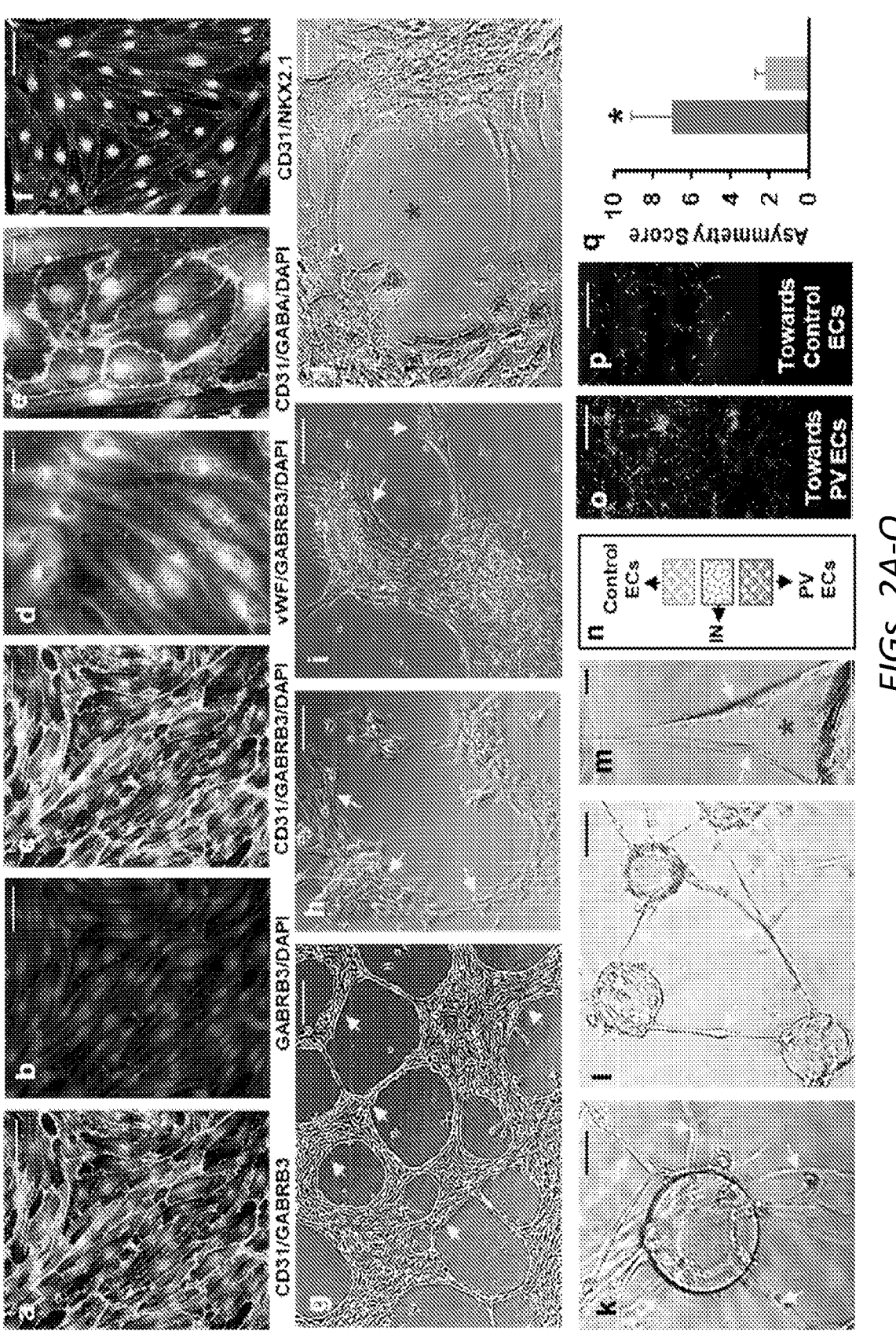
FIGs. 2A-Q

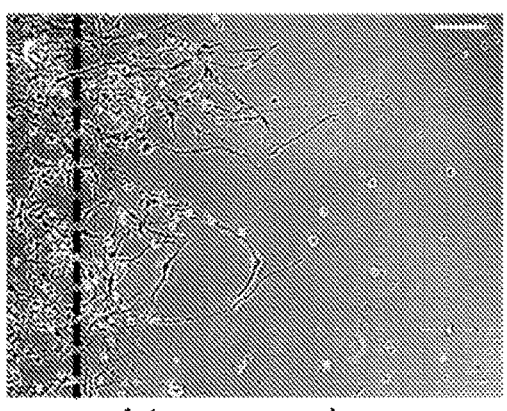
Interneurons only
*FIG. 2R*
Interneurons + control ECs
*FIG. 2S*
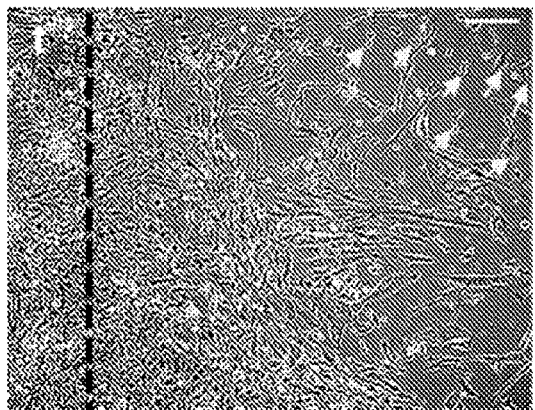
Interneurons + Periventricular ECs
*FIG. 2T*
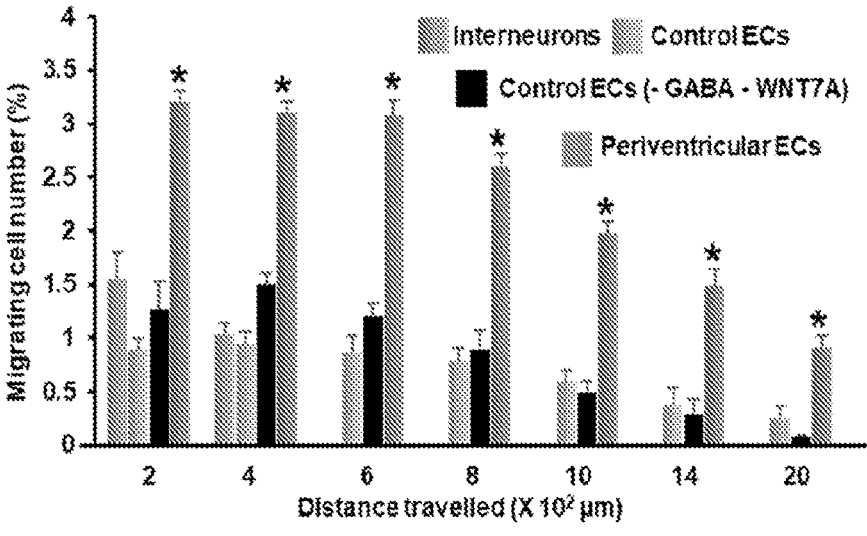
*FIG. 2U*

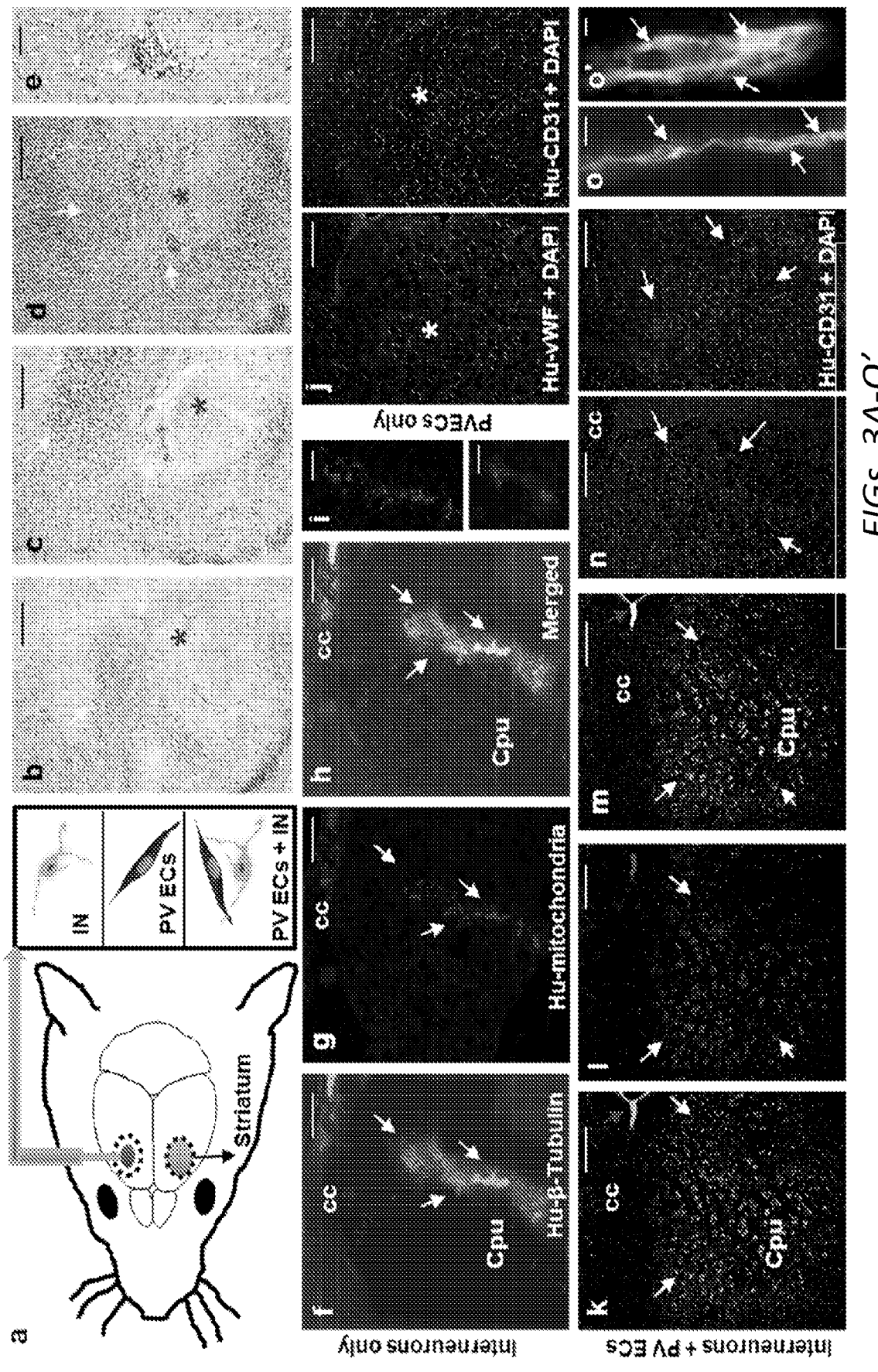
FIGs. 3A-O'

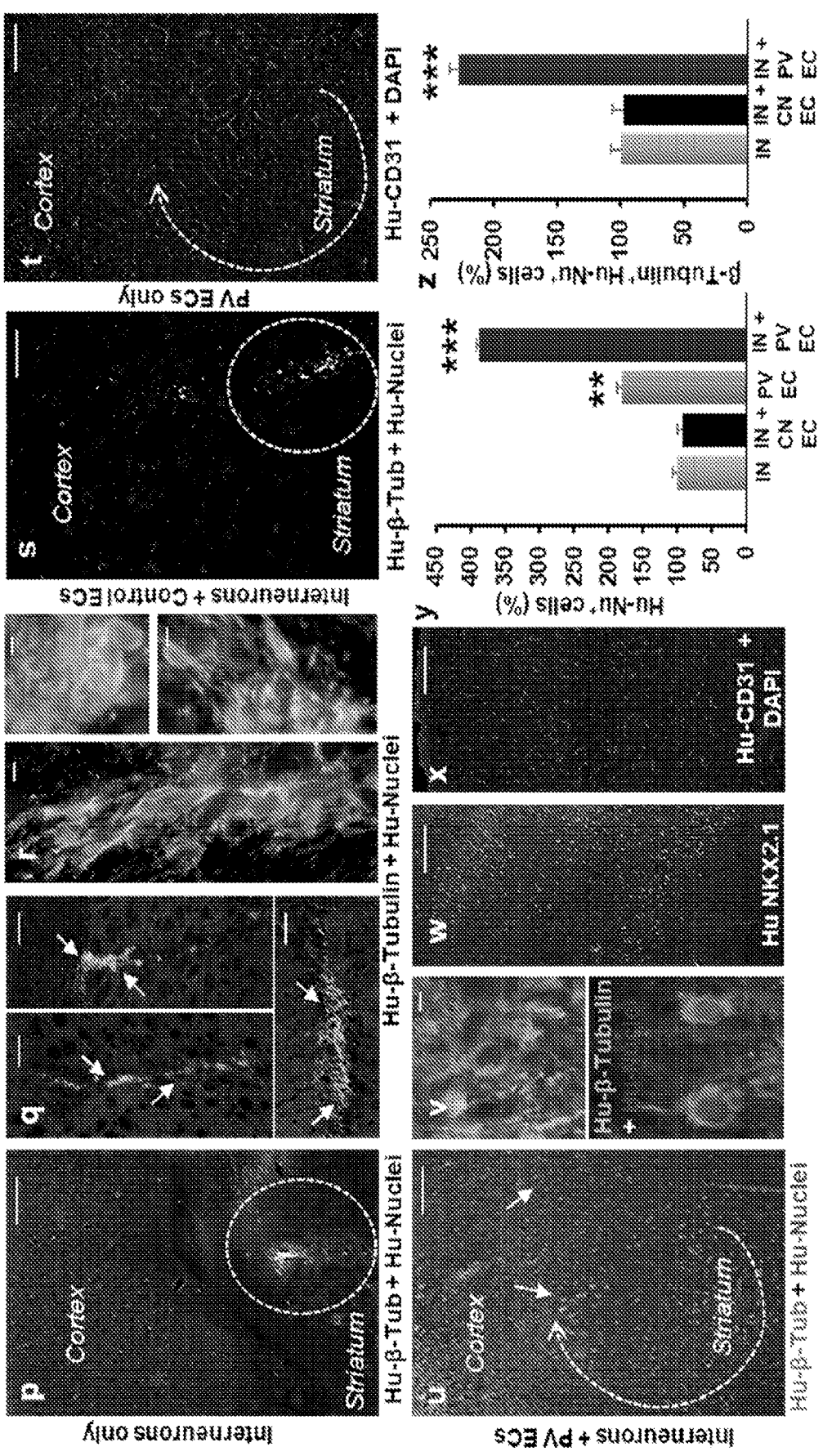
*FIGs. 3P-Z*

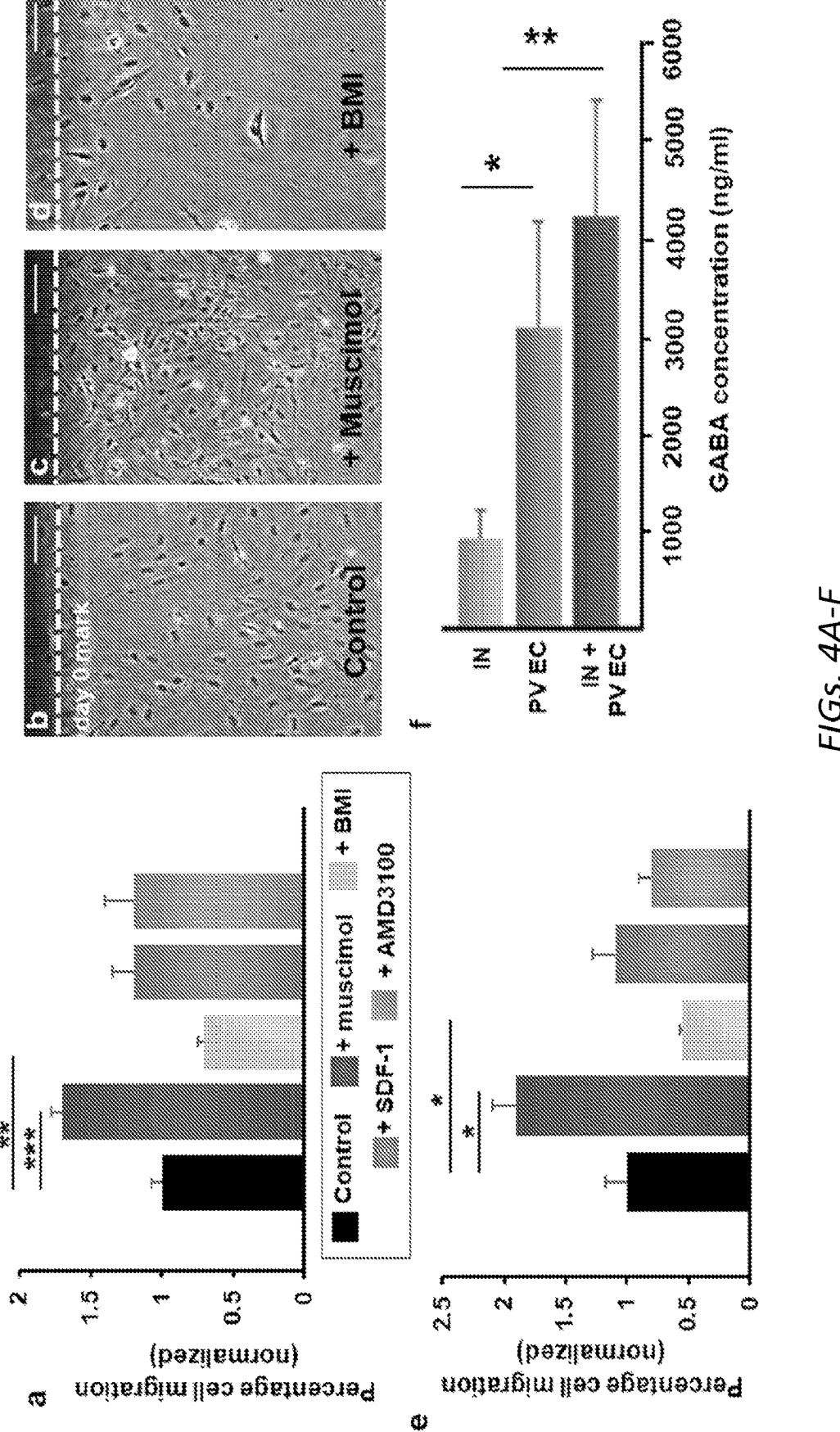
FIGs. 4A-F

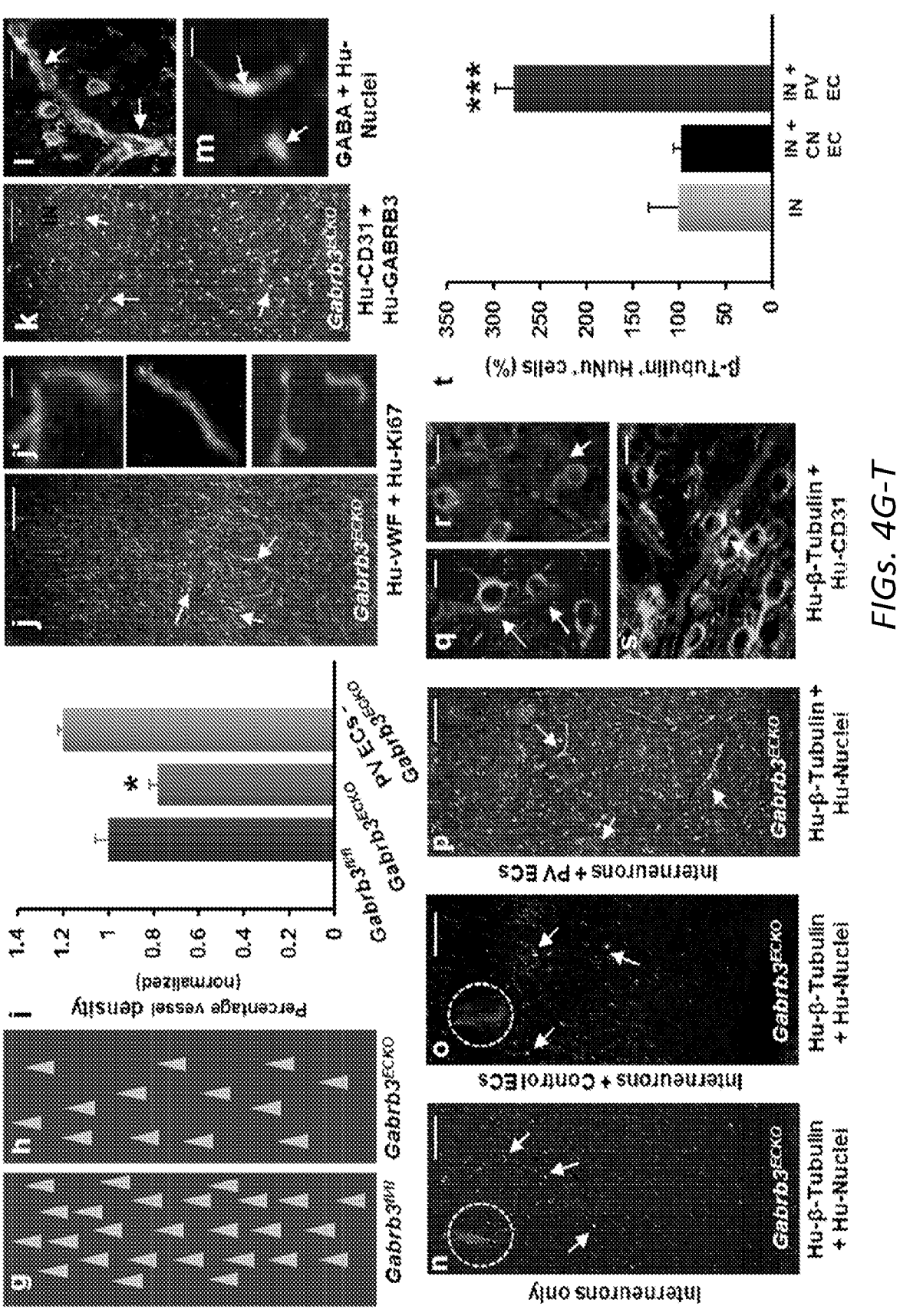
FIGs. 4G-T

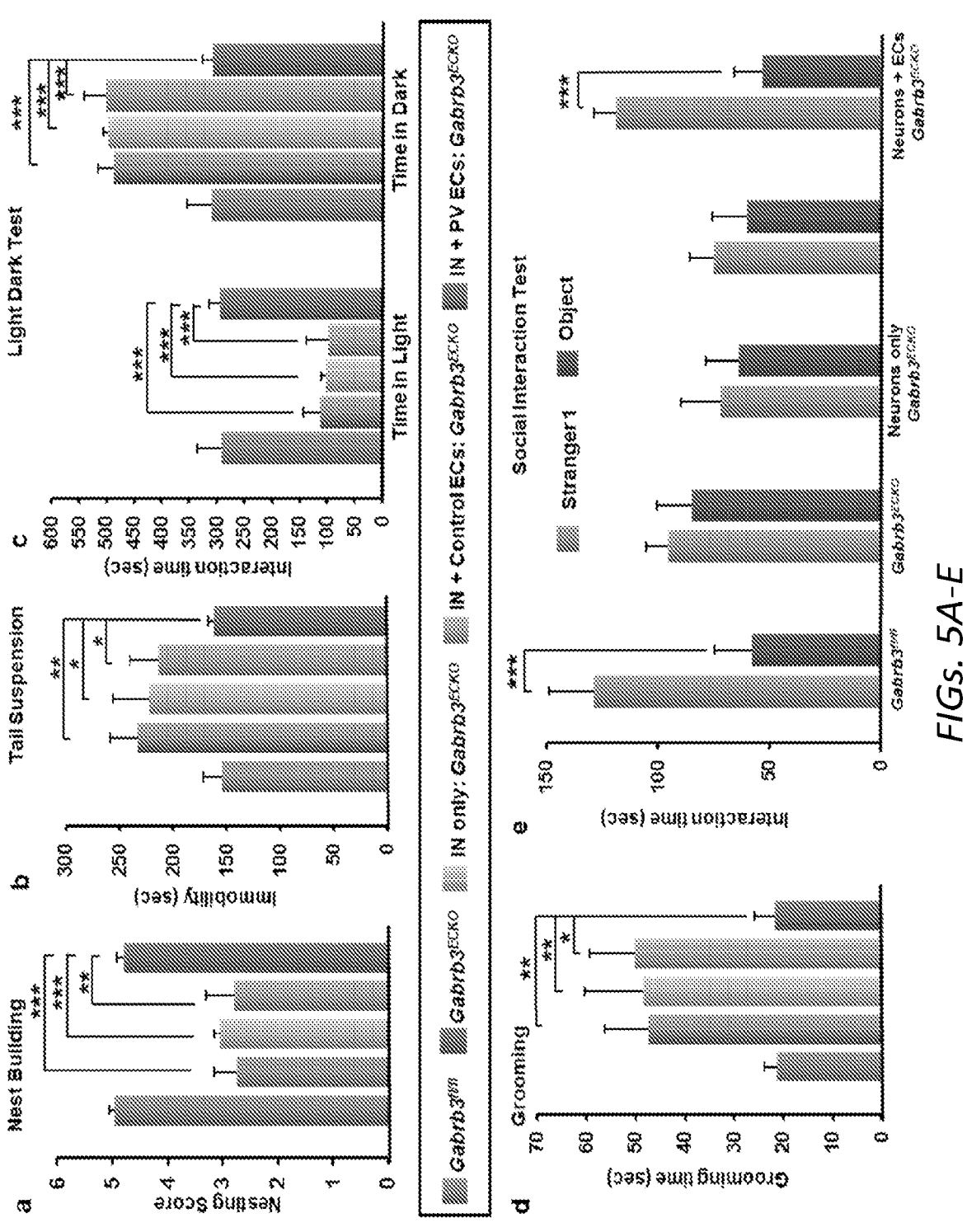
FIGs. 5A-E

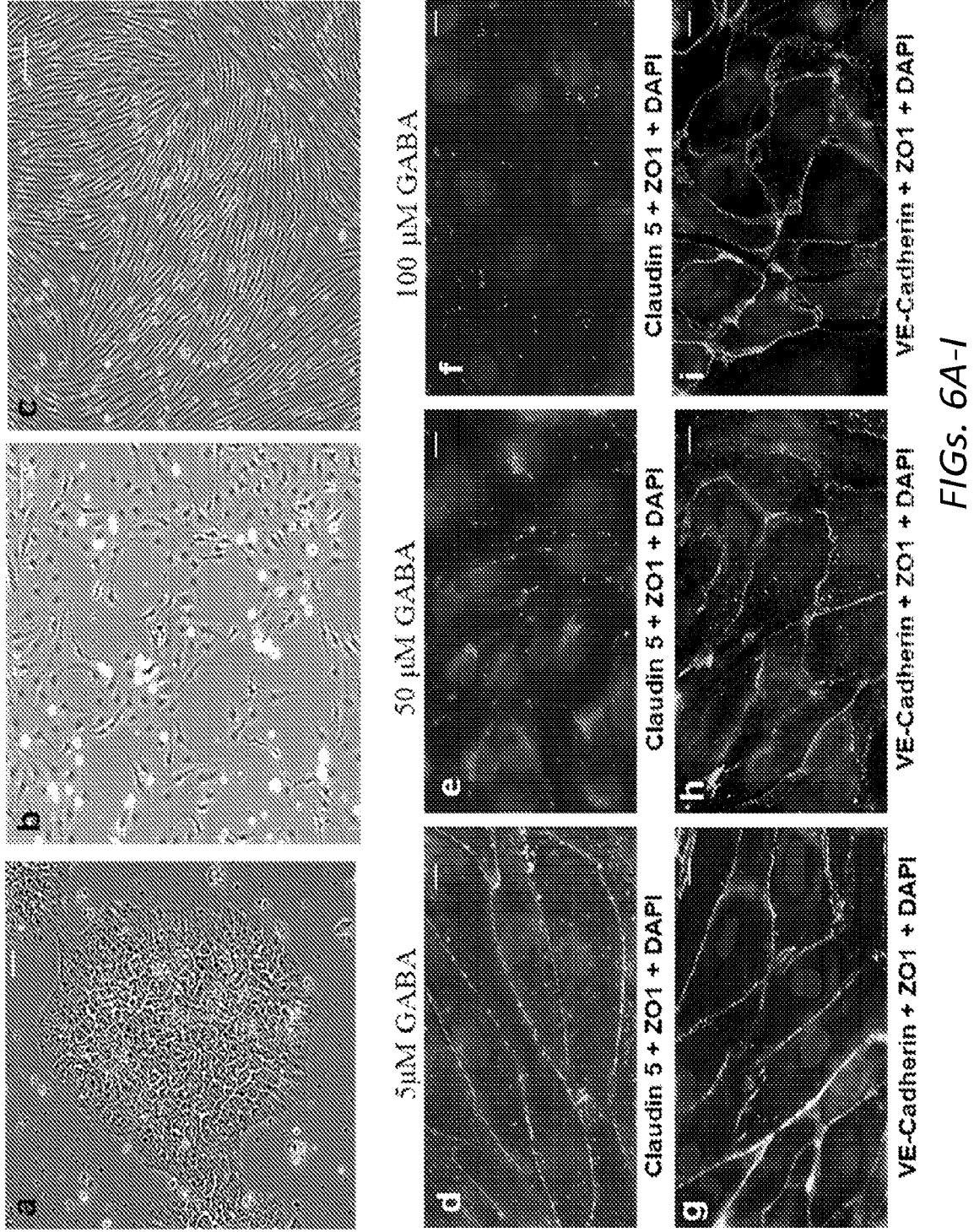
FIGs. 6A-I

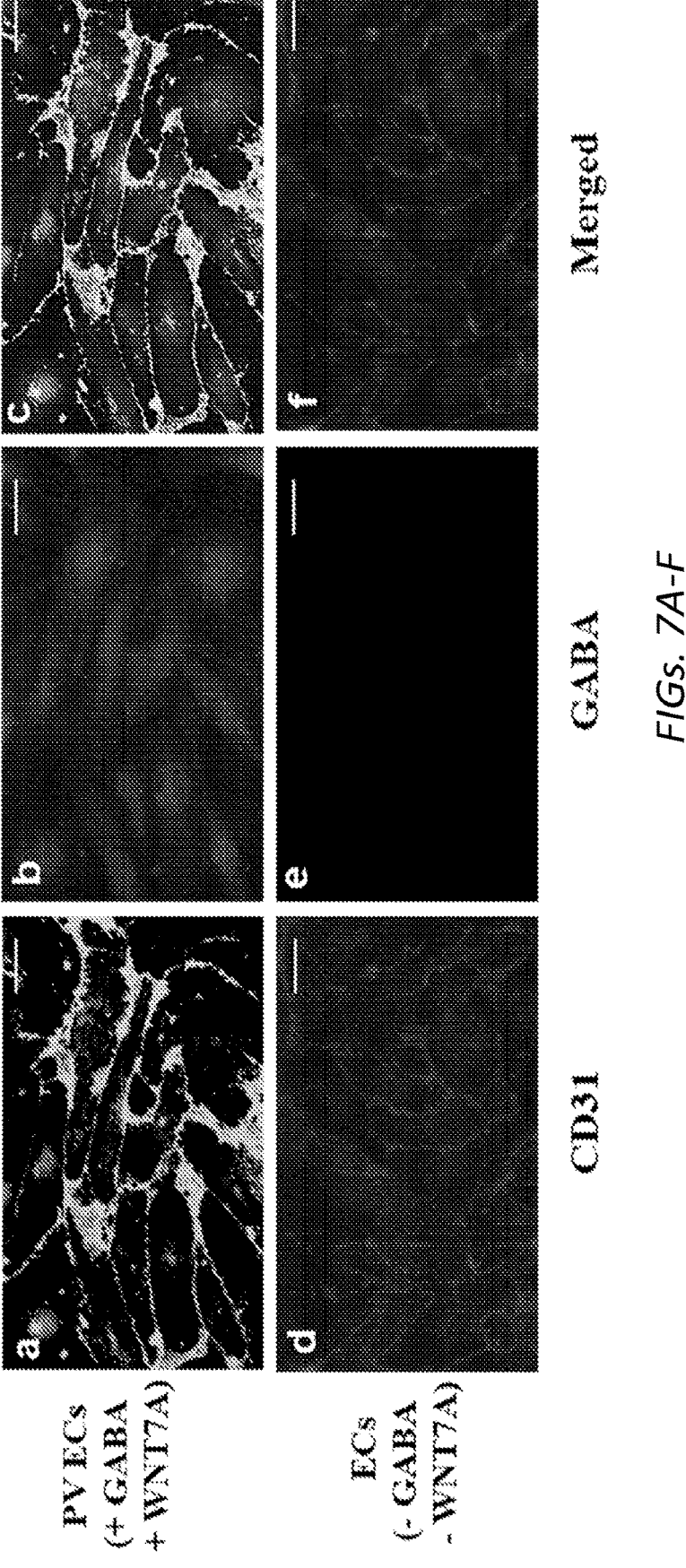
FIGs. 7A-F

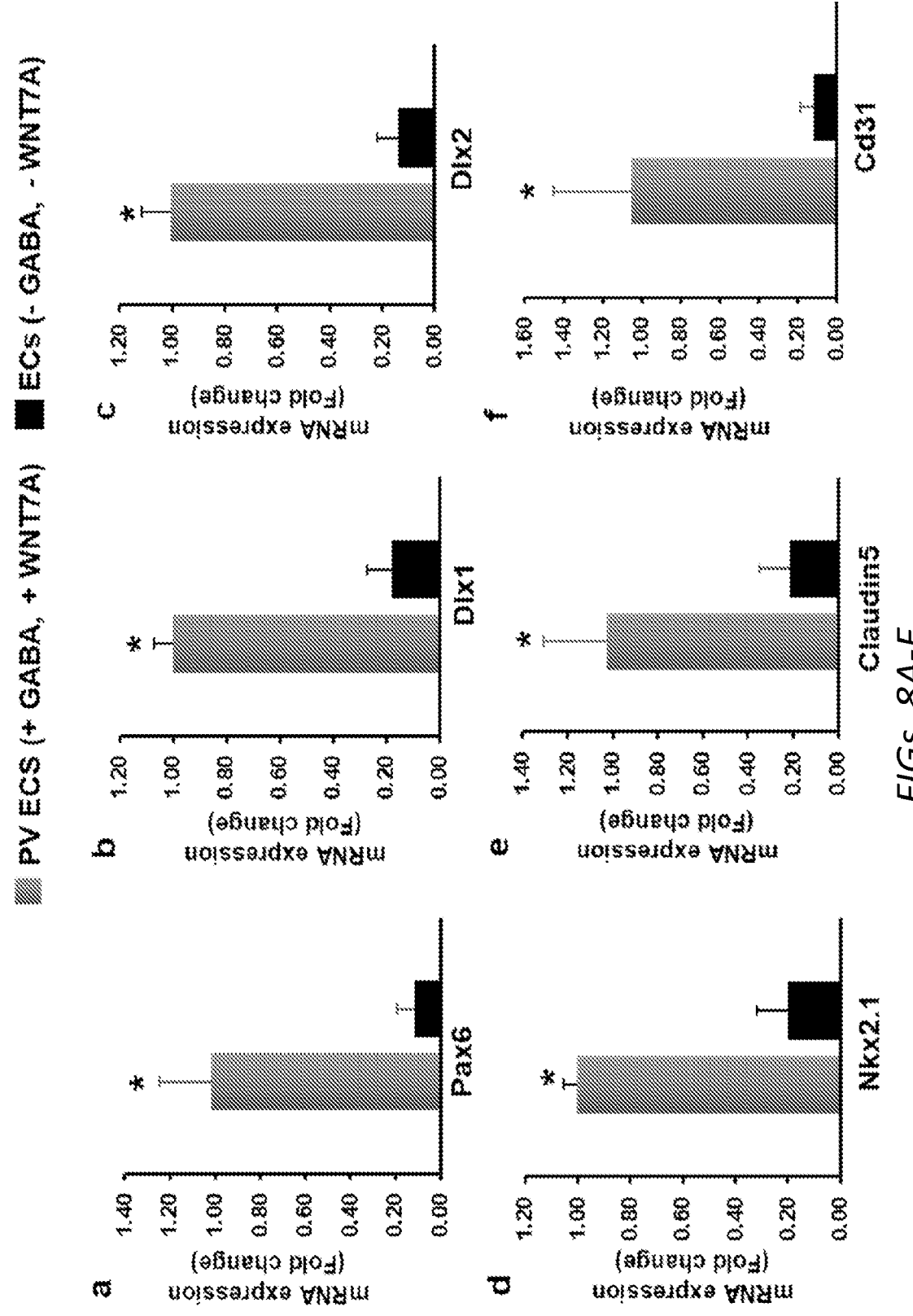
FIGs. 8A-F

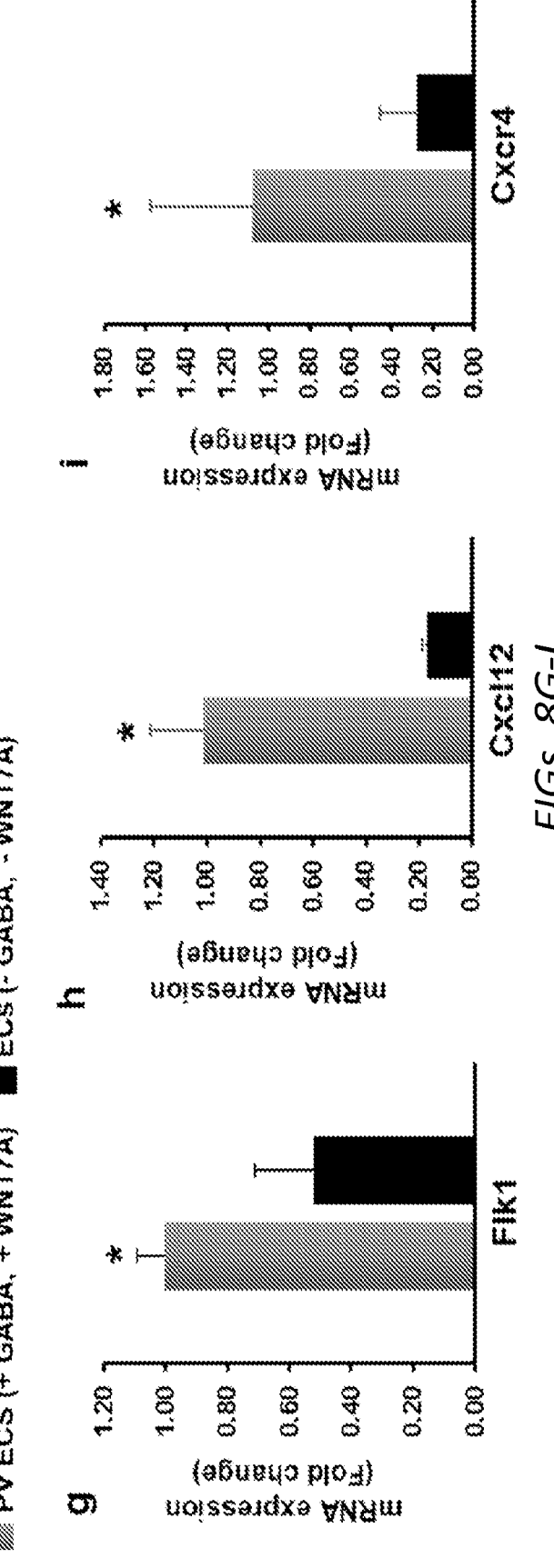
FIGs. 8G-I

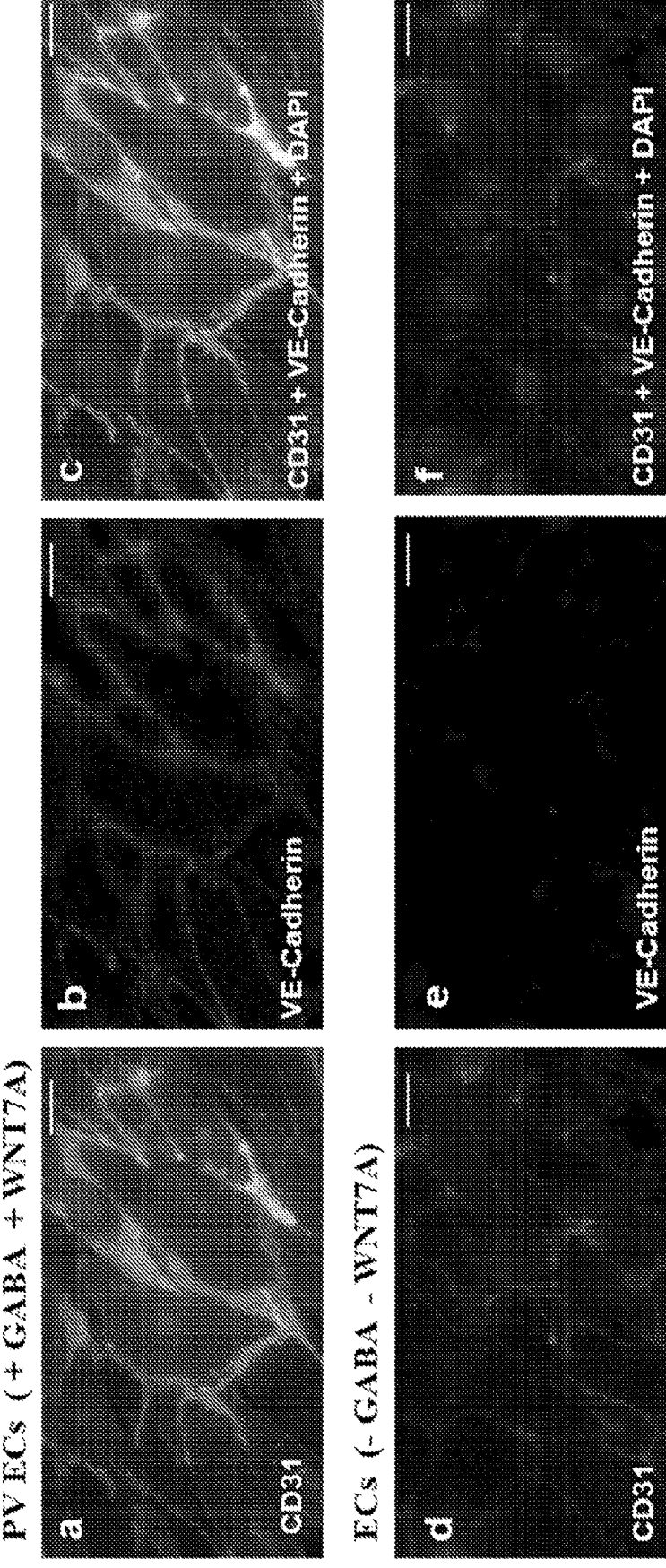
*FIGs. 9A-F*

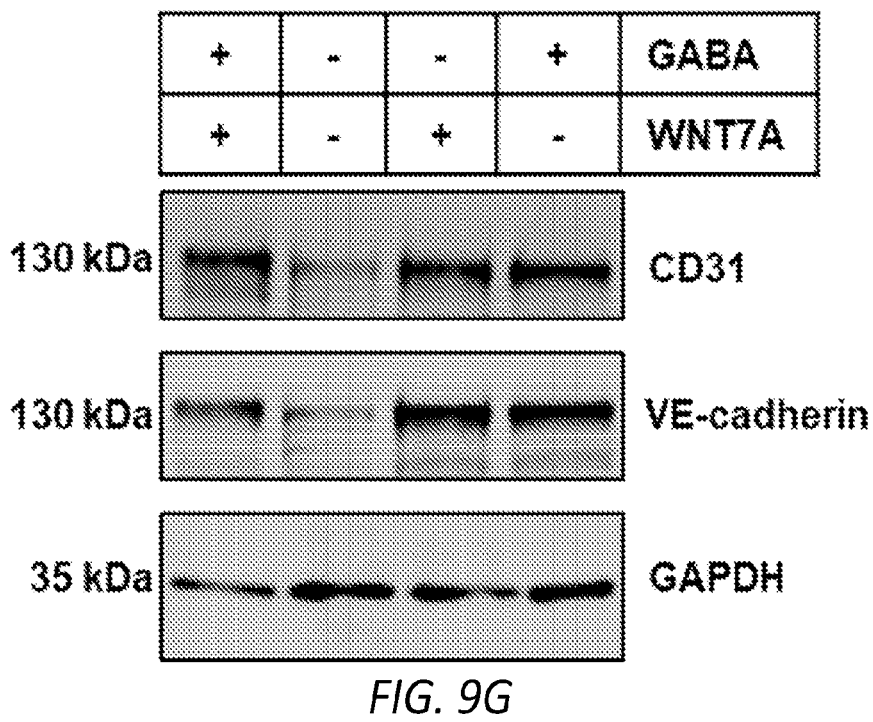
*FIG. 9G*
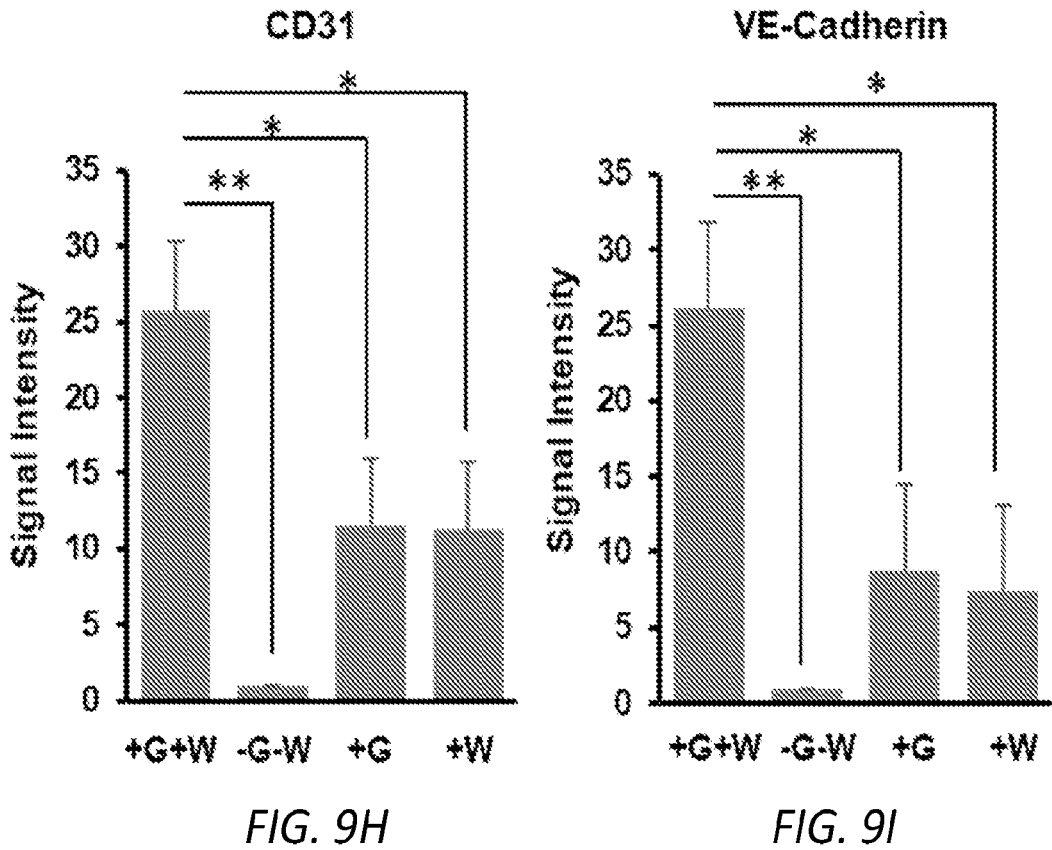
*FIG. 9H*                    *FIG. 9I*

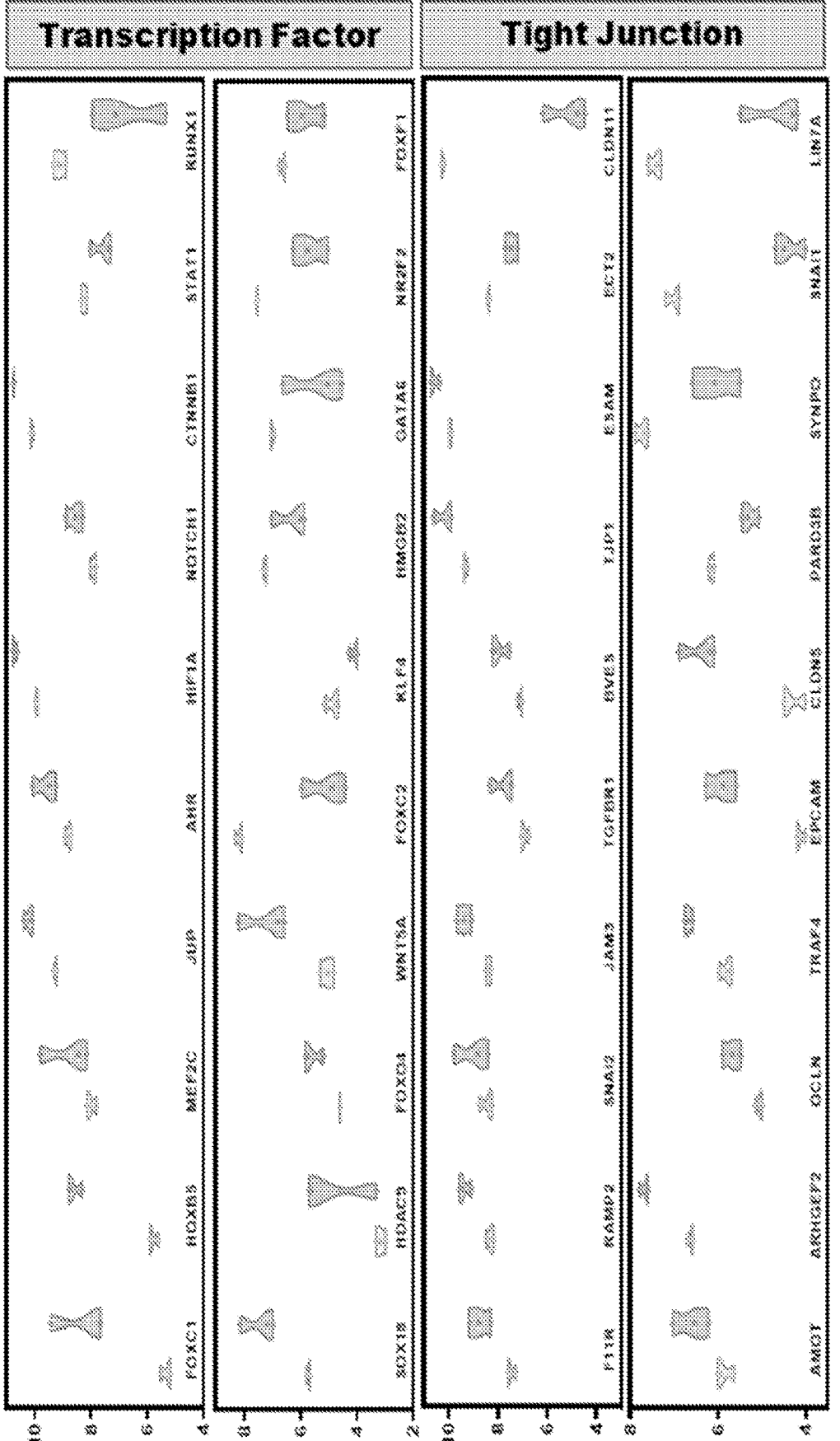
FIG. 11, continued

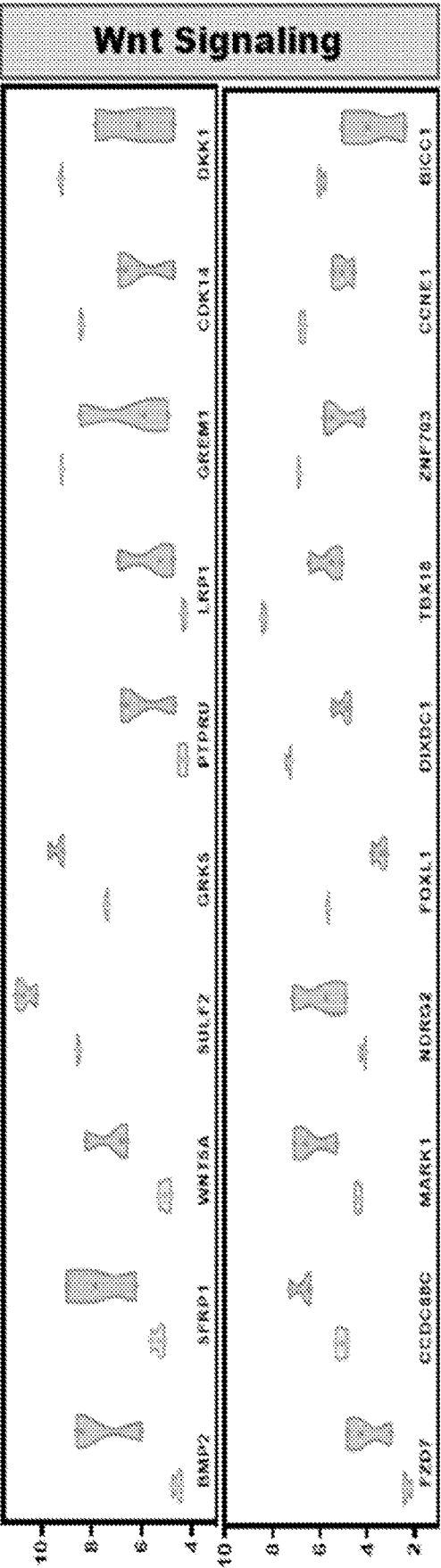
*FIG. 11, continued*

*Gabrb3* $^{fl/fl}$
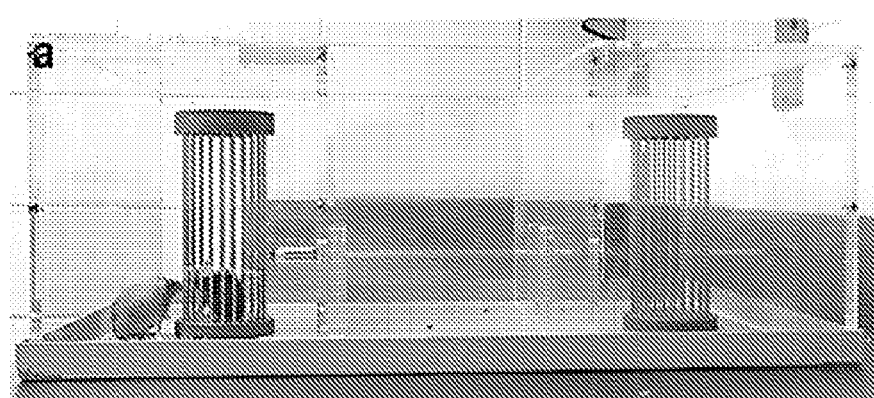
*Gabrb3* $^{ECKO}$
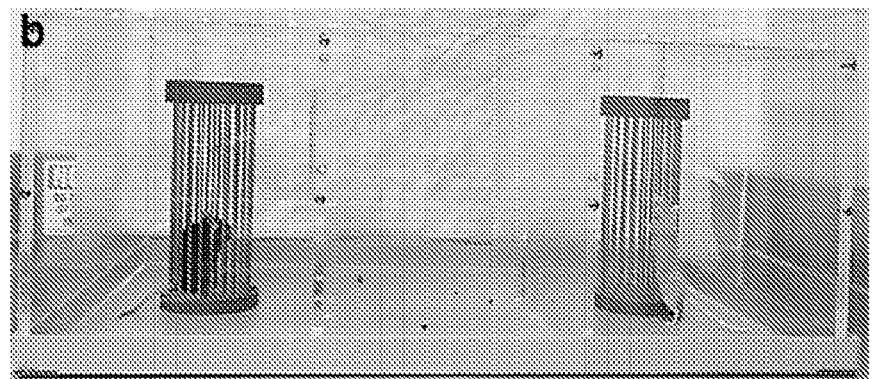
Interneurons
+ PV ECs :
*Gabrb3* $^{ECKO}$
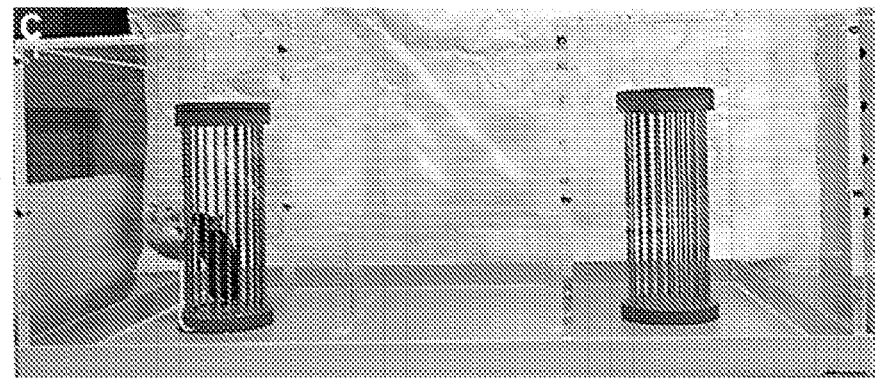
Interneurons
only:
*Gabrb3* $^{ECKO}$
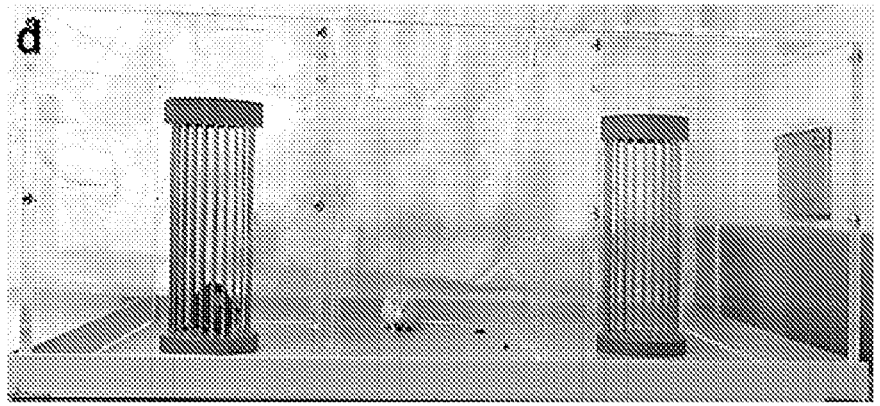
*FIGs. 14A-D*

HUMAN PERIVENTRICULAR ENDOTHELIAL CELL THERAPY FOR NEUROPSYCHIATRIC DISORDERS

CLAIM OF PRIORITY

This application is the National Stage of International Application No. PCT/US2020/056366, filed on 19 Oct. 2020, which claims the benefit of U.S. Provisional Application Ser. No. 62/923,512, filed on 19 Oct. 2019. The entire contents of the foregoing are incorporated herein by reference.

FEDERALLY SPONSORED RESEARCH OR DEVELOPMENT

This invention was made with Government support under Grant Nos. MH110438 and NS100808 awarded by the National Institutes of Health. The Government has certain rights in the invention.

TECHNICAL FIELD

Described herein are methods for generating human forebrain-like endothelial cells, compositions comprising the cells, and methods of use thereof in therapy.

BACKGROUND

Abnormal migration, positioning and reduction in GABAergic interneurons during the critical prenatal developmental period results in dysfunctional cortical neuronal synchrony implicated in brain diseases such as autism, epilepsy and schizophrenia[1-5], conditions awaiting more effective treatments. Cell transplantation is a powerful tool to introduce new cells with intrinsic plasticity to overcome cellular deficits and initiate repair and regeneration. To be successful, grafted cells should possess the ability to migrate and disperse through affected areas, differentiate into fully mature neurons, functionally integrate, and modulate circuitry activity in the damaged host brain. A better comprehension of the cellular and molecular mechanisms of interneuron development has led to use of their neuronal precursors in transplantation[6-8]. While the origin and specification of cortical GABAergic interneurons was well established[9-11], mechanisms that underlined their migration was not fully understood. Our studies served to address this critical gap by showing that embryonic forebrain vascular networks are strategically positioned to provide physical support and critical guidance cues for GABAergic interneuron migration in the developing telencephalon[12-14]. Additionally, our work has established novel autonomous links between the periventricular vascular network and the origin of psychiatric disorders, from the earliest developmental time points[13, 15]. Understanding brain development thus begins with an appreciation of all of its cellular components. Deeper insights into the anatomy, origin, molecular regulation, function and dysfunction of the periventricular vascular network in the last decade[12-15] was crucial for understanding its direct significance for psychiatric disorders.

SUMMARY

Abnormalities of or reductions in GABAergic interneurons are implicated in the pathology of severe neuropsychiatric disorders, for which effective treatments are still elusive. Transplantation of human stem cell-derived interneurons is a promising cell-based therapy for treatment of these disorders. In mouse xenograft studies, human stem cell derived-interneuron precursors could differentiate in vivo, but required a prolonged time of four to seven months to migrate from the graft site and integrate with the host tissue. This poses a serious roadblock for clinical translation of this approach. For transplantation to be effective, grafted neurons should migrate to affected areas at a faster rate. Endothelial cells of the periventricular vascular network are the natural substrates for GABAergic interneurons in the developing mouse forebrain, and provide valuable guidance cues for their long-distance migration. Additionally, periventricular endothelial cells house a GABA signaling pathway with direct implications for psychiatric disease origin. As shown herein, this discovery translates into humans, with significant therapeutic implications. The present inventors generated human periventricular endothelial cells, using human pluripotent stem cell technology, and extensively characterized its molecular, cellular and functional properties. Co-culture of human periventricular endothelial cells with human interneurons significantly accelerated interneuron migration in vitro and led to faster migration and wider distribution of grafted interneurons in vivo, compared to neuron-only transplants. Furthermore, the co-transplantation strategy was able to rescue abnormal behavioral symptoms in a pre-clinical model of psychiatric disorder, within one month after transplantation. This strategy facilitates angiogenesis-mediated treatment of psychiatric disorders.

Thus, provide herein are methods for generating a population of human forebrain periventricular endothelial cells. The methods include providing a population of pluripotent stem cells: (i) culturing the population of pluripotent stem cells in a first, stem cell media comprising Wnt7a protein and gamma amino-butyric acid (GABA), for a first time period sufficient to generate mesodermal cells; (ii) culturing the mesodermal cells in a second, vascular inducing medium comprising an inhibitor of transforming growth factor beta (TGFβ) signaling, vascular endothelial growth factor-A (VEGF-A), WNT7A e.g., about and GABAe, for a time sufficient to generate endothelial-like cells;
(iii) culturing the endothelial-like cells in a third, endothelial cell culture medium, (e.g., E6 medium) comprising growth factors, e.g., VEGF-A and FGF2, and GABA, for a time sufficient for development of a population of cells comprising CD31⁺GABRB3⁺ endothelial cells, and (iv) optionally isolating CD31⁺GABRB3⁺ cells from the mixture, thereby generating a population of human forebrain periventricular endothelial cells.

In some embodiments, the population of pluripotent stem cells comprise human embryonic stem cells or induced pluripotent stem cells (iPSC); in some embodiments the cells can be identified by the presence of markers OCT4 and TRA1-60.

In some embodiments, the first, stem cell media comprises E8 media with one or more growth factors; bone morphogenetic protein 4 (BMP4); Activin A; and a small molecule activator of WNT signaling.

In some embodiments, the growth factors comprise Fibroblast growth factor 2 (FGF2) and either TGFβ or NODAL.

In some embodiments, the small molecule activator of WNT signaling is a compound listed in Table A, preferably CHIR99021.

In some embodiments, the inhibitor of TGFβ signaling is a small molecule inhibitor of TGF-β/Smad signaling pathway, preferably SB431542.

In some embodiments, the endothelial-like cells express CD31 and von In some embodiments, the growth factors in the third, endothelial cell culture medium comprise VEGF and FGF2.

In some embodiments, the cells in the population of human forebrain perivascular endothelial cells express one or more periventricular endothelial cell markers selected from the group consisting of GABRB3, GABA, NKX2.1, PAX6, and ISL1.

In some embodiments, the methods further include maintaining the purified CD31$^+$GABRB3$^+$ cells in endothelial cell culture medium comprising growth factors and GABA.

In some embodiments, the concentration of GABA in the first and second media is 1-10 uM, preferably 5 uM.

Also provided herein are populations of human forebrain perivascular endothelial cells generated by a method described herein, and compositions comprising the populations of human forebrain periventricular endothelial cells, in a sterile carrier. In some embodiments, the cells are frozen.

Further provided herein are methods of treating a mammal, the method comprising administering to the brain of the mammal a population of human forebrain periventricular endothelial cells generated by a method described herein, and optionally a population of neuronal cells. Also provided are populations of human forebrain periventricular endothelial cells generated be a method described herein, for use in transplantation into a mammal, e.g., in combination with a population of neuronal cells.

In some embodiments, the methods increase numbers of interneurons in the forebrain of the mammal. In some embodiments, the mammal is in need of such treatment. In some embodiments, the mammal is a human.

In some embodiments, the neuronal cells are GABAergic interneurons, e.g., calretinin+, parvalbumin+, somatostatin+ or Neuropeptide Y+ neurons.

In some embodiments, the cells are transplanted into the cerebral cortex or into the hippocampus of the mammal. In some embodiments, the cells are transplanted into the cingulate cortex, motor cortex, somatosensory cortex, or piriform cortex in the cerebral cortex.

In some embodiments, the subject has a neuropsychiatric or neurological disease or disorder. In some embodiments, the neuropsychiatric or neurological disease or disorder is schizophrenia, epilepsy, autism, severe depression, cortical lesions, or a neurodegenerative disease (e.g., Alzheimer's disease). In such methods, the endothelial cells generated using a method described herein can be transplanted in combination with suitable neuronal cells, e.g., neuronal cells that are missing or depleted from the brain of the subject. In some embodiments, e.g., wherein the subject has a vascular disease or disorder, cerebral ischemia or stroke, the method can include transplanting only the endothelial cells generated using a method described herein, without additional neuronal cells.

Provided herein are methods to generate human periventricular endothelial cells expressing gamma amino-butyric acid (GABA) from human Embryonic Stem Cells (e.g., as shown in FIG. 1A of the Specification) comprised of exposing a human ES cell line in media sequentially to: (a) factors that induce or promote a mesodermal phenotype; (b) factors that induce or promote a vascular phenotype; and (c) factors that induce or promote a periventricular endothelial cell phenotype.

In some embodiments, the factors that induce or promote the mesodermal phenotype include, but are not limited to, Bone Morphogenetic Protein 4, Activin A and a small molecule activator of the WNT pathway. In some embodiments, the small molecule activator of the WNT pathway is CHIR99021.

In some embodiments, the factors that induce or promote the vascular phenotype include, but are not limited to, an inhibitor of the TGFβ signaling pathway and Vascular Endothelial Growth Factor-A. In some embodiments, the inhibitor of the TGFβ signaling pathway is SB431542.

In some embodiments, the factors that induce or promote a periventricular endothelial cell phenotype include, but are not limited to, Wnt7a and gamma amino-butyric acid (GABA). In some embodiments, the concentration of GABA is 5 μM.

In some embodiments, the media includes, but is not limited to, E8.

Also provided herein are methods to isolate differentiated human periventricular endothelial cells from other differentiated cells comprised of sorting said differentiated human periventricular endothelial cells from other differentiated cells by fluorescence activated cell sorting (FACS) and wherein a cell surface marker unique to embryonic periventricular endothelial cells is used to isolate said differentiated cells. In some embodiments, the cell surface marker unique to embryonic periventricular endothelial cells is CD31+ GABRB3+.

Also provided herein are methods to improve human GABAergic interneuron migration comprised of providing a source of vasculature or endothelial cells for GABAergic interneurons such that said GABAergic interneurons can align and migrate along the surface of said vasculature or endothelial cells. In some embodiments, the source of vasculature or endothelial cells for GABAergic interneurons is human periventricular cells expressing GABA prepared by a method described herein.

In some embodiments, the improved GABAergic interneuron migration is an in vitro culture or microfluidic system.

In some embodiments, the improved GABAergic interneuron migration is in vivo.

Additionally, provided herein are methods to treat or repair brain damage or neurological or neuropsychiatric diseases in a patient comprised of co-transplanting in said patient a source of neuronal cells or neuronal cell precursors and a source of vasculature or endothelial cells for providing the effective guidance and migration of said transplanted neuronal cells. In some embodiments, the ratio of neuronal cells or neuronal cell precursors to vasculature or endothelial cells is 1:1. In some embodiments, the source of neuronal cells is GABAergic interneurons. In some embodiments, the source is human periventricular cells expressing GABA prepared by a method described herein. In some embodiments, the neurological or neuropsychiatric diseases include (but are not limited to) autism, epilepsy, and schizophrenia.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-L. Derivation of human periventricular endothelial cells from human embryonic stem cells. (a) Schematic of an exemplary human periventricular endothelial cell differentiation protocol. (b-c) Phase contrast images of the day 6 cell population (b) and pure population of human periventricular endothelial cells at day (c). (d) Periventricular endothelial cells showed robust CD31 expression upon addition of WNT7a and GABA from day 0-5 of differentiation, while addition of GABA alone, selectively increased CD31 expression on endothelial cell-cell junctions. (e) Co-labeling with endothelial cell markers, vWF and CD31 of human periventricular endothelial cells. (f) High magnification image of vWF labeling of periventricular endothelial cells. (g) Flow cytometry analysis showing CD31$^+$GABRB3$^-$, CD31$^-$GABRB3$^+$ and double positive CD31$^+$GABRB3$^+$ populations. (h) Frequencies of human periventricular endothelial cells are CD31$^+$/GABRB3$^+$. Data represents mean±SD (n=6, *P<0.05, Student's t-test). (i) Heat map showing top 20 differentially expressed genes in H9 cells versus H9-derived periventricular endothelial cells (PV ECs), indicating efficient endothelial cell differentiation. (j-l) Heat maps showing top 20 upregulated genes in H9-derived periventricular endothelial cells versus control endothelial cells in three different categories: angiogenesis (j), GABA pathway (k) and neurogenesis (l) categories. Scale bars: b, 100 μm (applies to c), d, 50 μm (applies to e, f).

FIGS. 2A-V. Molecular and functional characterization of H9-derived human periventricular endothelial cells. (a-c) Images of GABRB3 and CD31 expression in all human periventricular endothelial cells and merged images with DAPI. (d-f) Co-labeled images of vWF and GABRB3 (d), CD31 and GABA (e), and CD31 and NKX2.1 (f) in periventricular endothelial cells. (g) Bright-field image showing the tube-formation (arrows) ability of human periventricular endothelial cells. (h j) Tube formation assay in 3D-fibrin gels. When cultured in fibrin gel, human periventricular endothelial cells aligned (arrows) and formed tubular structures with a lumen (asterisk) within 48 hours. (k-m) Sprouting and tube formation in fibrin gels. Nascent sprouts (arrows) are observed on day 2 (k) that continue to proliferate, migrate, and form intercellular tubes (arrows in l) with a clear lumen (asterisk, m). (n) Schematic of the chemoattraction assay. Using a three-well culture insert, interneurons (IN) were seeded in the middle (dotted rectangle), while periventricular endothelial cells (PV ECs; orange dotted rectangle) and control endothelial cells (ECs; dotted rectangle) were seeded on either side. (o, p) β-Tubulin labeled images of interneurons showing robust migration towards periventricular endothelial cells (o) but not towards control endothelial cells (p). (q) Quantification of chemoattraction of interneurons towards periventricular endothelial cells versus control endothelial cells. Data represents mean±S.D, (n=10, *P<0.05, Student's t test). Scoring scheme modified from Won et al.[13] (r-t) Migration of interneurons in interneuron-only culture (r), when co-seeded with control endothelial cells (s), and co-seeded with periventricular endothelial cells (t) 48 hours after seeding. The black dotted line represents the day 0 mark. Interneurons when co-seeded with periventricular endothelial cells migrated over a farther distance (shown in arrows in t) than compared to when seeded alone (r) or seeded with control endothelial cells (shown in white arrows in s). (u) Quantitation of long-distance migration ability of human periventricular endothelial cells, in comparison to interneurons, control endothelial cells (HAEC-like) and endothelial cells derived without GABA and WNT7A at 48 hours post-seeding. Robust migration of periventricular endothelial cells over long distance was observed. Data represents mean±S.D, (n=10, ***P<0.001, *P<0.05, Student's t-test). (v) Quantification of distance migrated by interneurons when seeded alone, co-seeded with control endothelial cells, and co-seeded with periventricular endothelial cells. Graph shows the distance travelled by the 50 farthest interneurons in each condition on day 5. Migration of interneurons was significantly accelerated when co-seeded with periventricular endothelial cells. Data represents mean±S.D, (n=10, ***P<0.001, Student's t test). Scale bars: a, 100 μm (applies to b, c, f, g-l, o, p, r-t), d, 50 μm (applies to e, m).

FIGS. 3A-Z. Human periventricular endothelial cells significantly promoted interneuron migration in vivo. (a) Schema of transplantation strategy in adult NOD SCID mouse. Human interneurons plus periventricular endothelial cells were co-transplanted in the striatum of 8 weeks old adult NOD-SCID mice. Interneurons-only, periventricular endothelial cells-only or interneurons plus control endothelial cells were also transplanted in separate experiments. One month after transplantation, brains were collected and processed for histology or IHC. (b-e) H & E staining of co-transplanted brain showing the graft core (asterisk) and the cell distribution close to graft (arrows). (f-i) Individual markers human β-Tubulin (f), human mitochondria (g) and a co-labeled image of both with DAPI (h) illustrate grafted neurons in interneuron-only transplanted brain that remained mostly within the graft area (white arrows). Arrow marks lateral ventricle boundary. (i) Magnified images of stalled neurons that are human mitochondria$^+$ at graft sites. (j, two panels) In periventricular endothelial cells-only transplanted brains, grafted endothelial cells labeled with human vWF and CD31 markers showed robust migration within the striatum. Nuclei were stained with DAPI. (k-m) In interneuron+periventricular endothelial cell co-transplanted brains, interneurons showed significantly higher migration ability, and distributed widely in the striatum (white arrows). A co-labeled image of human β-Tubulin, human mitochondria and DAPI is shown in m. Arrows mark the lateral ventricle boundary. (n, two panels) Robust migration (white arrows) of periventricular endothelial cells in co-transplanted striatum. (o, o') Co-labeling with isolectin B4 and anti-human CD31 shows how newly formed CD31$^+$ vessels anastomose with host vessels. (p) In interneuron-only transplanted brains, grafted neurons showed very little migration into the cortex (asterisks). The white dotted area marks the grafted site in the striatum where most of the neurons remained restricted. (q, r—three panels each) Additional stalled neurons (white arrows) from different brains are shown at 20× (q) and 40× (r) magnifications. (s) In neurons+control endothelial cells (without GABA and WNT7A) transplanted brain, grafted neurons remain stalled at the graft site (marked by white dotted circle). (t) In periventricular endothelial cells-only transplanted brain, endothelial cells migrated efficiently into the cortex. (u) In co-transplanted brains, grafted interneurons showed robust migration into cortical region (white arrows). (v) Magnified images (40×) of grafted human interneurons in the cortex. (w) Migrated cells in the cortex of co-transplanted brains show human-NKX2.1 labeling. (x) Robust distribution of human-CD31$^+$ endothelial cells in the cortex of co-transplanted brains. (y) Cell count analyses of human-nuclei[+] cells that have migrated into the cortex after 30 days. Data represents mean±S.D, (n=20, *P<0.001, P<0.01, Student's t test). (z) Quantification of β-Tubulin[+]/human nuclei[+] neurons in the cortex of transplanted brains 30 days after grafting. Data represents mean±S.D, (n=20, ***P<0.001, Student's t test). Significantly higher percentage of interneurons in neuron+periventricular endothelial cell co-transplanted brains showed long-distance migration compared to those in interneuron-only condition or interneuron+control endothelial cells derived without GABA and WNT7A condition. For (y) and (z), cell numbers in cingulate, motor, somatosensory and piriform cortex at all bregma levels were analyzed. Scale bars: b, 100 μm (applies to b-d, f-h, j, k-n, p, s-u, w, x), e, 50 μm (applies to i, o, q), r, 25 μm (applies to o', v). Cpu: striatum; cc: corpus callosum; IN: interneurons-only; CN EC: control endothelial cells derived without GABA and WNT7A; PV ECs: periventricular endothelial cells.

FIGS. 4A-T. Human periventricular endothelial cell-derived GABA regulates cell migration. (a-d) Migration of periventricular endothelial cells in response to addition of GABA$_A$ receptor agonist muscimol (100 μM), GABA$_A$ receptor antagonist BMI (100 μM), chemokine SDF-1α (40 nM) and CXCR4 inhibitor AMD3100 (100 μM). (a) Quantitation of migration assay. Addition of muscimol resulted in higher percentage of cells migrating out, while addition of BMI resulted in less cell migration, compared to control (no chemicals added). Presence of SDF1 or AMD3100 showed no significant effect on migration of periventricular endothelial cells (n=5, mean±SD, P<0.01, *P<0.001, Student's t-test). (b-d) Representative phase contrast images showing periventricular endothelial cell migration in control, +muscimol, and +BMI conditions. (e) Quantitation of interneuron migration when co-cultured with periventricular endothelial cells pre-treated with chemicals for 48 hours. Interneurons co-cultured on muscimol-treated periventricular endothelial cells showed increased migration than those co-cultured on untreated periventricular endothelial cells (control), while interneurons co-cultured with BMI-treated periventricular endothelial cells showed decreased migration compared to control (n=5, mean±SD, *P<0.05, Student's t-test). Treatment of periventricular endothelial cells with SDF or AMD3100 had no effect on interneuron migration. (0 Quantitation of GABA secretion measured by ELISA. GABA level was significantly higher in interneuron+periventricular endothelial cell co-culture and in periventricular endothelial cell-only population, compared to interneuron-only population. (n=6, mean±SD, *P<0.05, **P<0.01, Student's t-test). (g, h) Schema depicting normal vasculature (lattice pattern) and GABAergic interneurons (triangles) in Gabrb3$^{fl/fl}$ cerebral cortex (g), while in Gabrb3$^{ECKO}$ cerebral cortex (h) there is both a vascular deficit (dotted pattern) and a deficit in GABAergic interneurons (triangles). (i) Quantification of vessel densities. Periventricular endothelial cell-transplanted Gabrb3$^{ECKO}$ mice showed significant rescue in vessel densities in the cerebral cortex when compared to Gabrb3$^{ECKO}$ mice (n=6, mean±SD, *P<0.05, Student's t-test). (j-k) Transplanted human periventricular endothelial cells undergo proliferation as shown by human vWF/Ki67 co-labeling (j; high magnification images shown in j'), and continue to express GABRB3 (k) and GABA (l, m) in vivo (white arrows). (n-o) Migration pattern of transplanted interneurons in somatosensory cortical region of transplanted Gabrb3$^{ECKO}$ brain. Grafted interneurons showed poor migratory ability (white arrows) and remained mostly near the grafted site (dotted white area) in interneuron-only transplanted brain (n) and interneuron+control endothelial cell co-transplanted brain (o). (p) In interneuron+periventricular endothelial cell co-transplanted brains, interneurons showed extensive migration and widespread distribution (white arrows). (q-s) Magnified images showing close interactions between transplanted interneurons and new vessels formed by human periventricular endothelial cells. (t) Quantitation of β-Tubulin+/human nuclei+ neurons in cortex (including cingulate, motor, somatosensory and piriform cortical regions) of Gabrb3$^{ECKO}$ transplanted brain, 30 days after grafting. Significantly higher number of grafted neurons in interneuron+periventricular endothelial cell co-transplanted Gabrb3$^{ECKO}$ brains showed migration all over cortex, compared to those in interneuron-only or interneuron+control endothelial cell transplanted brains. Data represents mean±S.D, (n=20, ***P<0.001, Student's t test). Scale bar: b, 100 μm (applies to c, d, j, k, n-p), 1, 50 μm (applies to j' m, q, r, s). IN: interneurons; CN EC: control endothelial cells derived without GABA and WNT7A; PV ECs: periventricular endothelial cells.

FIGS. 5A-G. Co-transplantation of human periventricular endothelial cells with human interneurons in cortex ameliorates behavioral abnormalities in Gabrb3$^{ECKO}$ mice. (a-e) Quantification of behavioral tests performed in five different groups of mice: sham control Gabrb3$^{fl/fl}$, Gabrb3$^{ECKO}$, only interneurons transplanted into the cortex of Gabrb3$^{ECKO}$ mice, interneurons+control endothelial cells derived without GABA and WNT7A co-transplanted (1:1 ratio) into the cortex of Gabrb3$^{ECKO}$ mice and interneuron+periventricular endothelial cells co-transplanted (1:1 ratio) into the cortex of Gabrb3$^{ECKO}$ mice. In all transplanted and sham control mice, tests were done 30 days post-transplantation. In each case, data represents mean±S.D, (n=6, *P<0.05, Student's t test). (a) Nesting behavior was assayed by a five-point nesting score. Interneuron+periventricular endothelial cell co-transplanted mice showed normal nesting behavior, similar to sham control mice. Interneuron-only transplanted mice and interneuron+control endothelial cell co-transplanted mice showed poor nest building abilities, similar to Gabrb3$^{ECKO}$ mice. (b) Tail suspension test. Interneuron+periventricular endothelial cell co-transplanted Gabrb3$^{ECKO}$ mice showed an immobility time comparable to sham control mice, while interneuron-only transplanted mice and interneurons+control endothelial cell transplanted mice showed longer immobility time, similar to Gabrb3$^{ECKO}$ mice. (c) Quantification of exploration time in light-dark box test. Interneuron+periventricular endothelial cell co-transplanted Gabrb3$^{ECKO}$ mice spent similar time exploring light and dark sides of the box, as observed in sham control mice. Interneuron-only transplanted Gabrb3$^{ECKO}$ mice and interneuron+control endothelial cell co-transplanted Gabrb3$^{ECKO}$ mice behaved like Gabrb3$^{ECKO}$ mice and continued to spend more time in the dark side of the box. (d) Quantification of self-grooming time. Interneuron+periventricular co-transplanted Gabrb3$^{ECKO}$ mice showed shorter grooming times, comparable to sham control mice. On the other hand, interneuron-only transplanted Gabrb3$^{ECKO}$ mice and interneuron+control endothelial cell co-transplanted Gabrb3$^{ECKO}$ mice continued to show long grooming times, similar to that observed for Gabrb3$^{ECKO}$ mice. (e) In a three-chamber social interaction test, interneuron+periventricular endothelial cell co-transplanted Gabrb3$^{ECKO}$ mice spent a significantly longer amount of time interacting with a stranger mouse than with an inanimate object, similar to that observed in sham control mice. In contrast, behavior of interneuron only-transplanted Gabrb3$^{ECKO}$ mice and interneuron+control endothelial cell co-transplanted mice were reminiscent of Gabrb3$^{ECKO}$ mice. They did not show any specific preference for the stranger mouse and spent similar time exploring both the stranger mouse and an inanimate object. These behavioral tests show that co-transplantation of interneurons with human periventricular endothelial cells led to an effective rescue of behavioral deficits in Gabrb3$^{ECKO}$ mice after one month of transplantation. (f) Summary schema illustrating the importance of WNT7A/GABA addition to the differentiation medium and isolation of GABRB3$^+$/CD31$^+$ endothelial cells by FACS for the efficient generation of human periventricular endothelial cells, that release high levels of GABA and promote robust neuronal chemoattractivity and migration. (g) Summary schema depicting a novel co-transplantation strategy of human periventricular endothelial cells with human GABAergic interneurons into multiple brain regions in two different mouse models (NOD-SCID and Gabrb3$^{ECKO}$) that independently confirm robust cell migration and distribution. The benefit of this co-transplantation manifested as an improvement in behavioral function (light-dark box illustrated in schema) in Gabrb3$^{ECKO}$ mice, signifying the importance of novel angiogenesis-based treatment strategy for psychiatric disorders.

FIGS. 6A-I. Human periventricular endothelial cell morphology and effect of GABA. Phase contrast images of: (a) an undifferentiated colony of the embryonic stem cell line H9, (b) human periventricular endothelial cells after 2 days of splitting and (c) a confluent culture of human periventricular endothelial cells. (d-i) GABA concentration impacts tight junction formation in human periventricular endothelial cells. (d-f) Addition of 5 uM GABA increases tight junction formation (d), observed by antibody staining against tight junction proteins Claudin5 and ZO-1, in comparison to higher concentration of 50 μM (e) or 100 μM (f) GABA. (g-i) Expression of VE-Cadherin, an adherens junction protein, is not affected by increase in GABA levels. Scale bar: a, 50 μm (applies to d-i); b, 100 um (applies to c).

FIGS. 7A-F: Effect of GABA and WNT7A. Double staining with antibodies against CD31 (left column) and GABA (center column) show that GABA and WNT7A are required for the expression of endogenous GABA in human periventricular endothelial cells. (a-c) Periventricular endothelial cells express GABA when derived in the presence of GABA and WNT7A. (d-f) GABA is not detected in endothelial cells derived without GABA and WNT7A. These cells also have significantly lower levels of CD31 (shown also in FIGS. 8A-I and FIGS. 9A-I). Scale bar: a, 100 μm (applies to b-f).

FIGS. 8A-I. Differences in gene expression between human periventricular endothelial cells and control endothelial cells derived without GABA and WNT7A. Real time qPCR analysis show decreased levels of Pax6, Dlx1, Dlx2, Nkx2.1, Claudin 5, Cd31, Flk1, Cxcl12 and Cxcr4 (8A-I, respectively) in control endothelial cells derived without GABA and WNT7A, in comparison to human periventricular endothelial cells. Bar graphs show fold change±SD values of relative transcript expression normalized to GAPDH and compared with values obtained from three independent experiments (n=3, *P<0.05, Student's t test).

FIG. 9A-I. Decrease in expression of CD31 and VE-Cadherin in endothelial cells derived without GABA and WNT7A. (a-f) Immunocytochemical staining show substantially low expression of CD31 and VE-Cadherin in endothelial cells that are generated without addition of GABA and WNT7A (d-f), in comparison to human periventricular endothelial cells (a-c). (g) A representative western blot image showing CD31 and VE-Cadherin protein levels in human periventricular endothelial cells (+GABA, +WNT7A) versus in endothelial cells derived without GABA and WNT7A, with WNT7A but not GABA, and with GABA but not WNT7A. (h,i) Quantification of signal intensities from western blot confirms significant decrease in levels of CD31 and VE-Cadherin proteins in endothelial cells when derived without addition of GABA and/or WNT7A. Each data point represents mean±SD values calculated from three independent biological replicates per group. (n=3, *P<0.05, **P<0.01, Student's t test). G: GABA; W: WNT7A; PV ECs: periventricular endothelial cells FIG. 10. Tissue fate mapping of control endothelial cell gene expression confirmed their cardiac-like identity.

FIGS. 14A-D. Rescue of social-interaction deficit in co-transplanted Gabrb3$^{ECKO}$ mice. (a) In a three-chambered social approach task, control Gabrb3$^{fl/fl}$ mouse spent more time with stranger mouse than with an in-animate novel object. (b) Gabrb3$^{ECKO}$ mice showed no extra preference for stranger mouse, and spent similar time exploring both the chambers. (c) Co-transplanted Gabrb3$^{ECKO}$ mice showed significantly higher preference towards interacting with stranger mouse. (d) Interneuron-only transplanted mice did not show a preference for stranger mouse, and spent more time investigating the inanimate cage. They also spent a considerable amount of time in the middle chamber. PV ECs=periventricular endothelial cells.

DETAILED DESCRIPTION

Due to the restricted availability of human fetal tissue for cell therapy, human pluripotent stem cell (hPSC) technology provides an unprecedented opportunity to study disease mechanisms[16-22]. Multiple groups have successfully derived human interneuron/interneuron progenitors from hPSCs[23-26] and transplantation of interneurons/interneuron progenitors has emerged as a promising treatment option for psychiatric disorders[27-32]. When transplanted in mouse[33] and rat[34] models of epilepsy, hPSC-derived interneuron precursors, survived well, fired action potentials, formed functional synaptic connections and could reduce abnormal seizure activities. Though showing great promise, one issue that needs improvement is the migration efficiency of transplanted cells. At two weeks post transplantation, transplanted interneurons displayed minimal migration, and it was only at four to seven months post transplantation, that some migration and integration into host brain was observed[23, 25, 33, 34]. Therefore, the beneficial effects of interneuron graft-in-disease models were observed only several months after transplantation. This presents an obstacle for the clinical translation of interneuron-based therapy, especially for very sick or severely affected patients. Another drawback that has been described with GABA producing cell types after transplantation is their transient effects, due to reductions in GABA levels[35, 36]. A decrease in GABA-mediated inhibition is a critical contributing factor for hyperexcitability and seizure initiation and increased secretion of GABA, by grafted cells, is important for increasing the seizure threshold. Thus, at present, while transplantation of GABAergic interneurons represents the most promising cell-based therapeutic alternative for GABA related diseases, there are difficulties that need to be overcome.

Figure 5F:
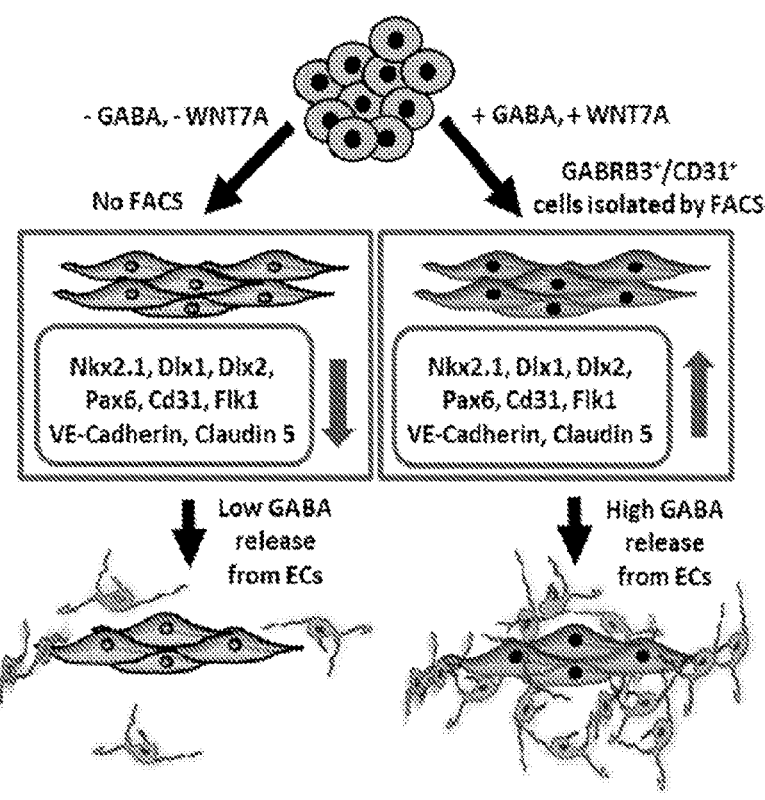

The key fundamental discovery that pre-formed vascular networks are the natural guides for GABAergic neuronal migration from the earliest developmental time point assumes a new significance here that can serve to improve hPSC-derived GABAergic neuronal migration. The periventricular vascular network not only acts as a physical substrate for neuronal migration in the embryonic forebrain, but also has a very unique gene expression profile, unlike endothelial cells from other brain regions or organs[12-15]. Periventricular endothelial cells show enriched expression of cell surface marker, $GABA_A$ receptor β3 subunit (GABRB3) as opposed to pial endothelial cells or control endothelial cells prepared from midbrain and hindbrain[15]. Therefore, GABRB3 serves as a valuable tool to selectively sort human endothelial cells which are akin to mouse periventricular endothelial cells. Additionally we know that periventricular endothelial cells express and release GABA that promotes rapid and extensive long-distance migration of GABAergic interneurons[15]. Neuronal GABA cannot compensate for the roles of endothelial GABA and interneurons stall in their migration in the absence of endothelial GABA[15]. This close neuro-vascular interaction during embryonic brain development that is sealed by space and time is the key missing link in interneuron-based therapy. Interestingly, it has been reported that transplanted neuronal precursors align and migrate along the surface of host blood vessels[37, 38] as though in search of a missing or lost counterpart. All of this fundamental knowledge provided us with strong rationale to generate human periventricular endothelial cells from human embryonic stem cells and to tap into the potential of these endothelial cells to improve human GABAergic interneuron migration in vitro and in vivo. Methods for Generating Human Embryonic Forebrain-Like Endothelial Cells Provided herein are methods for generation of human embryonic forebrain-like endothelial cells (e.g., periventricular endothelial cells) from human embryonic stem cells; the methods include addition or GABA and WNT7A for efficient differentiation, and isolation of GABRB3+/CD31+ cell population by FACS (FIG. 5f).

The present methods can be performed using stem cells, e.g., cells from a human embryonic stem cell line (e.g., H9, H1) or embryonic stem cell-like (ESC-like) induced pluripotent stem cells (iPSCs), e.g., generated from primary cells autologous to a subject to be treated using a method described herein. In some embodiments, the stem cells express markers of pluripotency, i.e., OCT4 and TRA1-60.

Methods for generating iPSC are known in the art. In some embodiments, the methods for generating hiPSC can include obtaining a population of primary somatic cells from a subject, e.g., a subject who is afflicted with PD and in need of treatment for PD. Preferably the subject is a mammal, e.g., a human. In some embodiments, the somatic cells are fibroblasts. Fibroblasts can be obtained from connective tissue in the mammalian body, e.g., from the skin, e.g., skin from the eyelid, back of the ear, a scar (e.g., an abdominal cesarean scar), or the groin (see, e.g., Fernandes et al., Cytotechnology. 2016 March; 68(2): 223-228), e.g., using known biopsy methods. Other sources of somatic cells for hiPSC include hair keratinocytes (Raab et al., Stem Cells Int. 2014; 2014:768391), blood cells, or bone marrow mesenchymal stem cells (MSCs) (Streckfuss-Bömeke et al., Eur Heart J. 2013 September; 34(33):2618-29). In some embodiments, the primary cells (e.g., fibroblasts) are exposed to (cultured in the presence of) factors sufficient to induce reprogramming to iPSC. Although other protocols for programming can be used (e.g., as known in the art or described herein), in preferred embodiments the present methods can include introducing (contacting or expressing in the cell) four transcription factors, i.e., Oct4, Sox2, Klf4, and L-Myc, known colloquially as the as Yamanaka 4 factors (Y4F). See, e.g., Takahashi and Yamanaka, Cell. 2006; 126(4):663-676; Takahashi et al., Cell. 2007; 131(5):861-872; Yu et al. Science. 2007; 318(5858):1917-1920; Park et al., Nature. 2008; 451(7175):141-146. In some embodiments, the methods also include contacting or expressing in the cell one or more miRNAs, e.g., (i) at least one miR-302 cluster member and (ii) at least one miR-200 cluster member; see US 20160298089 and Song et al., J Clin Invest. 2020; 130(2): 904-920.
Phase I In the first phase of the protocol, lasting about 2 days, e.g., about 44-52 hours, e.g., about 48 hours, mesodermal cell fate is induced in the stem cells by culturing them in media suitable for culture of stem cells, e.g., media comprising growth factors, E8 media (comprising insulin, selenium, transferrin, L-ascorbic acid, FGF2, and TGFβ (or NODAL) in DMEM/F12, see Chen et al., Nat Methods. 2011 May; 8(5): 424-429), supplemented with a mesoderm inducer, e.g., bone morphogenetic protein 4 (BMP4) or BMP-4/7 heterodimers, e.g., at about 2-10 ng/ml, e.g., about 5 ng/ml), Activin A (e.g., at about 15-50 ng/ml, e.g., about 25 ng/ml), and a small molecule activator of WNT pathway, e.g., a GSK3beta inhibitor (e.g., at about 0.1-5 µM, e.g., about 1 µM), e.g. as shown in Table A, as well as WNT7A protein (e.g., at about 100-1000 ng/ml, e.g., about 500 ng/ml) and a low concentration of GABA (e.g., at about 2-7.5 µM, e.g., about 5 µM).

TABLE A

| Small molecule activators of Wnt signalling | |
|---|---|
| Compound | Target |
| CHIR-98023 | GSK-3β |
| CHIR-99021 | GSK-3β |
| CHIR-99030 | GSK-3β |
| Hymenialdisine | GSK-3β |
| debromohymeialdisine | GSK-3β |
| dibromocantherelline | GSK-3β |
| Meridianine A | GSK-3β |

TABLE A-continued

Small molecule activators of Wnt signalling

| Compound | Target |
|---|---|
| alsterpaullone | GSK-3β |
| cazapaullone | GSK-3β |
| Aloisine A | GSK-3β |
| NSC 693868 | GSK-3β |
| (1H-Pyrazolo[3,4-b]quinoxalin-3-amine) | |
| Indirubin-3'-oxime | GSK-3β |
| (Indirubin-3'-monoxime; 3-[1,3-Dihydro-3-(hydroxyimino)-2H-indol-2-ylidene]-1,3-dihydro-2H-indol-2-one) | |
| A 1070722 | GSK-3β |
| (1-(7-Methoxyquinolin-4-yl)-3-[6-(trifluoromethyl)pyridin-2-yl]urea) | |
| L803 | GSK-3β |
| L803-mts | GSK-3β |
| TDZD8 | GSK-3β |
| NP00111 | GSK-3β |
| HMK-32 | GSK-3β |
| Manzamine A | GSK-3β |
| Palinurin | GSK-3β |
| Tricantin | GSK-3β |
| IM-12 | GSK-3β |
| (3-(4-Fluorophenylethylamino)-1-methyl-4-(2-methyl-1H-indol-3-yl)-1H-pyrrole-2,5-dione) | |
| NP031112 | GSK-3β |
| NP00111 | GSK-3β |
| NP031115 | GSK-3β |
| VP 2.51 | GSK-3β |
| VP2.54 | GSK-3β |
| VP 3.16 | GSK-3β |
| VP 3.35 | GSK-3β |

Phase II

During about days 2-5 (e.g., the subsequent 110-130 hours, e.g., about 120 hours), vascular induction is promoted by a vascular inducing medium, preferably comprising E6 medium (i.e., Dulbecco's modified Eagle's medium [DMEM]/F12, ascorbic acid, sodium bicarbonate, selenium, human transferrin, and human insulin (Lippmann et al., Stem Cells 2014; 32:1032-1042) along with inhibiting TGFβ signaling (e.g., using a small molecule inhibitor of TGF-β/Smad signaling pathway, e.g., SB431542 (e.g., at about 2-7.5 μM, e.g., about 5 μM) as known in the art or described herein) and by addition of vascular endothelial growth factor-A (VEGF-A, e.g., at about 25-75 ng/ml, e.g., about 50 ng/ml), BMP4 (e.g., at about 25-75 ng/ml, e.g., about 50 ng/ml), FGF2 (e.g., at about 50-150 ng/ml, e.g., about 100 ng/ml), WNT7A protein (e.g., at about 250-750 ng/ml, e.g., about 500 ng/ml) and a low concentration of GABA (5 μM) are also maintained in the media during phase II.

Non-limiting examples of small molecule inhibitors of TGF-β/Smad signaling pathway include SB431542; LDN-193189; Galunisertib (LY2157299); LY2109761; SB525334; A-83-01; AUDA; PD 169316; BIBF-0775; ITD-1; SB505124; Dorsomorphin (Compound C) 2HCl; Pirfenidone; GW788388; LY364947; RepSox; LDN-193189 2HCl; Sulfasalazine; K02288; SD-208; TP0427736 HCl; LDN-214117; SIS3 HCl; LY 3200882; Vactosertib; DMH1; LDN-212854; ML347; Halofuginone; and Dorsomorphin (Compound C), all of which are commercially available. Others are known in the art.

Phases III-IV

From about days 5-7 of differentiation, the cells are maintained in E6 media comprising growth factors (e.g., VEGF-A, e.g., at about 25-75 ng/ml, e.g., about 50 ng/ml and FGF2, e.g., at about 50-150 ng/ml, e.g., about 100 ng/ml) and GABA (e.g., at about 2-7.5 μM, e.g., about 5 μM). On day 7, differentiated CD31⁺GABRB3⁺ cells (usually >60% of total differentiated cells) can be isolated, e.g., by fluorescence activated cell sorting (FACS) (see, e.g., FIGS. 1G, H) and can then be further maintained in endothelial cell culture medium, e.g., E6 medium with growth factors (e.g., VEGF-A (e.g., at about 25-75 ng/ml, e.g., about 50 ng/ml), FGF2 (.g., at about 50-150 ng/ml, e.g., about 100 ng/ml), and GABA (e.g., at about 2-7.5 μM, e.g., about 5 μM).

Populations of Cells

Also provided herein are populations of cells derived using a method described herein. These cells functionally replicate the natural cells, in that they migrate into the brain and form vasculature that provides a migration-promoting path for co-transplanted neurons, e.g., GABAergic interneurons. The cells express one or more endothelial cell markers, i.e., CD31 and/or von Willebrand Factor (vWF) and one or more periventricular endothelial cell markers, i.e., GABRB3, GABA, NKX2.1, PAX6, and/or ISL1. They do not express pluripotent markers, e.g., OCT4 or TRA1-60.

Methods of Use

The general notion that it is not important which kind of human vasculature is used or that their purpose is to merely improve tissue survival and metabolic exchange is incorrect. Endothelial cells from different organs are not exclusively homogenous, responding to the metabolic demands of cell populations. Cell autonomous programs within CNS endothelial cells dictate complex aspects of their vascular function and specific neurovascular interactions[12-15] that can be re-capitulated only by developing isogenic vasculature to induce precise structural organization. In that respect, human periventricular endothelial cells generated using a method as described herein have significant potential as a source of cells for transplantation, e.g., into the forebrain, and can be used for human brain development modeling and disease.

Figure 5G:
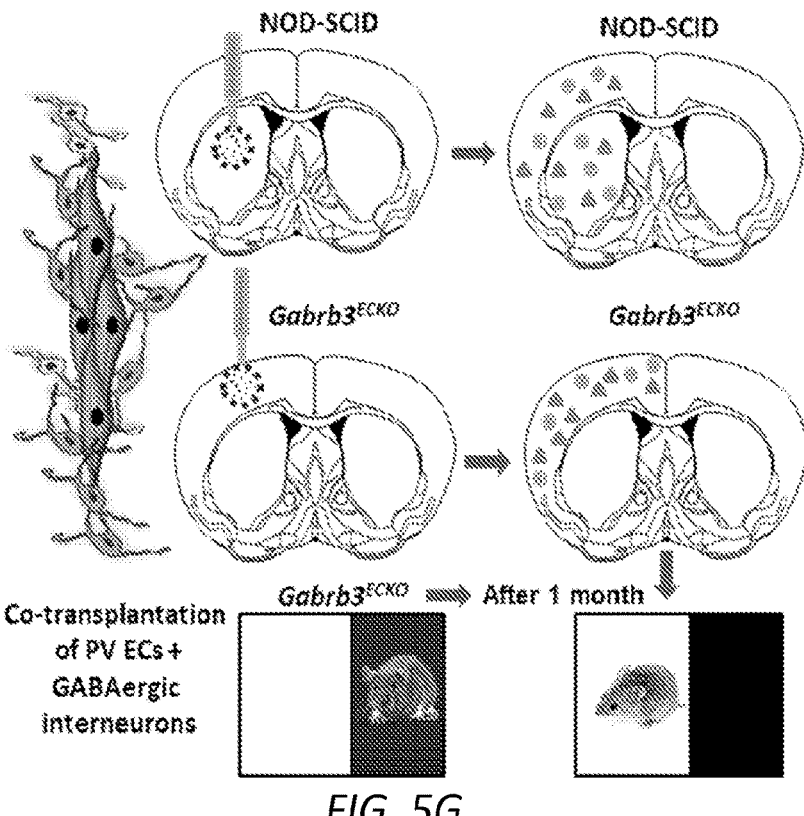

The human periventricular endothelial cells generated using the present methods provide a migration promoting corridor that help human GABAergic interneurons migrate long distances within shorter periods of time to integrate themselves with the host tissue, thereby providing greater significance for faster repair of brain damage. As shown herein, when transplanted into adult striatum, both endothelial cells and interneurons dispersed significantly and migrated both tangentially and long distance into the cerebral cortex, recapitulating the embryonic situation. Thus the embryonic stem cell-derived periventricular endothelial cells can be used in brain repair strategies, e.g., targeting different regions of the forebrain (e.g., as shown in FIG. 5g). These human embryonic forebrain-like endothelial cells can be used to treat or ameliorate a number of neuropsychiatric and neurological diseases including schizophrenia, epilepsy, autism, severe depression, vascular diseases, cerebral ischemia or stroke associated with neuronal cell death, cortical lesions, and neurodegenerative disorders, e.g., Alzheimer's disease (AD). As used herein, to "treat" means to ameliorate one or more symptoms of the disease.

Thus for example, these cells can be used alone for induction of forebrain specific angiogenesis, for treatment of forebrain vascular diseases, cerebral ischemia or stroke, by transplantation into or near an affected area of the brain. Thus in cases where the vasculature is abnormal and there is reduced blood flow in the brain, cells generated using a method described herein can be used for transplantation treatment strategies.

Also provided herein is a co-transplantation strategy with both endothelial and neuronal cell types, with significant benefits for brain repair. The identification of the molecular components involved in forebrain GABAergic interneuron development triggered the efficient generation of GABAergic neuronal populations based on ES cell engineering (see, e.g., Kim et al., Stem Cells. 2014; 32:1789-804; Maroof et al., Cell Stem Cell. 2013; 12:559-72; Nicholas et al., Cell Stem Cell. 2013; 12:573-86). However, these GABAergic interneurons have been used in transplantation without their natural substrate or guide, causing them to stall at transplantation sites with an inability to migrate into regions that require new neurons.

In some embodiments, the human forebrain endothelial cells generated using a method described herein can be used in co-transplantation protocols with GABAergic interneurons or subtypes (i.e., neurons that are calretinin+, parvalbumin+, somatostatin+ or Neuropeptide Y+) and with glutamatergic projection neurons, or with precursors thereof. Methods for generating these neurons are known in the art, see, e.g., Kim et al., Stem Cells. 2014; 32:1789-804; Maroof et al., Cell Stem Cell. 2013; 12:559-72; Nicholas et al., Cell Stem Cell. 2013; 12:573-86. The cells can be transplanted into the appropriate brain region in the cerebral cortex (e.g., in the cingular, motor, somatosensory, piriform) or hippocampus. In preferred embodiments, the human periventricular endothelial cells are generated from autologous (patient-derived) iPSCs. As shown herein, forebrain endothelial cell therapy improved behavioral function in an animal model. Gabrb3ECKO mice, a model of psychiatric disorder with partial loss of endothelial cell-secreted GABA in the embryonic telencephalon, have reductions in both blood vessels and GABAergic interneurons; therefore, transplantation of interneurons only did not rescue the abnormal behavioral symptoms. Co-transplantation of both the human periventricular endothelial cells and GABAergic interneurons resulted in behavioral rescue.

Methods for transplantation of cells into the brain are known in the art. In some embodiments, the cells are administered by being implanted directly into or near the affected area of the subject's brain, e.g., unilaterally or bilaterally, e.g., into one or more of the appropriate brain regions in the cerebral cortex (e.g., in the cingular, motor, somatosensory, piriform) or hippocampus, e.g., using magnetic resonance imaging-guided stereotactic surgery. See, e.g., Garitaonandia et al., Stem Cells Dev. 2018 Jul. 15; 27(14):951-957; Kikuchi et al., Nature 548: 592-596 (31 Aug. 2017); MOrizane et al., Nature Communications 8:385 (2017); Sonntag et al., Prog Neurobiol. 2018 September; 168:1-20.

Although the present methods exemplify humans, the methods can also be used in other mammals, e.g., primates and non-primate veterinary subjects including cats, dogs, and horses.

Brain Organoids

Human periventricular endothelial cells generated using the present methods can be used in brain organoid technology. Lack of blood vessels within growing brain organoids limits their application, both with respect to disease modeling and in the context of clinical transplantation. The current technique available for vascularization of organoids involves complex in vivo grafting of organoids'. The present methods for co-culture with periventricular endothelial cells can be used to improve forebrain organoid development, compartmentalization and structure as well as minimize organoid to organoid growth and variability. Exemplary methods to prepare brain organoids are known in the art, see, e.g., Mansour et al., Nat Biotechnol. 2018; 36:432-41; Kelava and Lancaster, Dev. Biol. 420, 199-209 (2016); Lancaster et al., Nature 501, 373-379 (2013); Paca et al., Nat. Methods 12, 671-678 (2015); Renner et al., EMBO J. 36, 1316-1329 (2017); Yin et al., Cell Stem Cell 18, 25-38 (2016); Giandomenico and Lancaster, Curr. Opin. Cell Biol. 44, 36-43 (2017); Schwarz et al., Proc. Natl. Acad. Sci. USA 112, 12516-12521 (2015). In some embodiments, the organoids can be developed from iPSCs obtained from patients to provide patient specific or disease-specific models, which can provide insights into disease etiology and pathogenesis.

EXAMPLES

The invention is further described in the following examples, which do not limit the scope of the invention described in the claims.

Materials and Methods

The following materials and methods were used in the Examples below.

Endothelial cell differentiation and culture: H9 cells (WiCell, Madison, WI) were maintained in E8 media (Thermo Fisher Scientific) on Matrigel (BD Biosciences)-coated plates and passaged once a week with 0.5 mM EDTA (Thermo Fisher Scientific) in PBS. On day 0 of differentiation, H9 cells were dissociated with Accutase (Sigma), and plated at a density of $10^5$ cells/cm$^2$ on Matrigel-coated plates. Cells were cultured for two days in E8 medium supplemented with BMP4 (5 ng/ml, Peprotech), Activin (25 ng/ml, Peprotech), CHIR 99021 (1 µM,) WNT7A (500 ng/ml, Peprotech), and GABA (5 µM, Sigma). Rock inhibitor, Y-27632 (1004, Selleck Chemicals) was added for first 24 hours to improve cell survival. On day 2, cells were switched to vascular inducing medium composed of E6 medium (Thermo Fisher Scientific) containing BMP4 (50 ng/ml), SB431542 (5 µM, Cayman Chemicals), GABA (5 µM), WNT7A (500 ng/ml), FGF2 (100 ng/ml, Peprotech) and VEGF-A (50 ng/ml, Peprotech). On day 5, cells were split at 1:6 ratio using Accutase and plated on Matrigel-coated plates in periventricular endothelial cell (PVEC) medium consisting of E6 with VEGF-A (50 ng/ml), FGF2 (100 ng/ml) and GABA (5 µM). On day 7, periventricular endothelial cells were isolated from the mixed population by fluorescence-activated cell sorting (FACS) and seeded on Matrigel-coated plates in periventricular endothelial cells medium at a density of $6\times10^5$ cells/cm$^2$. For routine culturing, periventricular endothelial cells were dissociated using Accutase, and seeded on Matrigel-coated plates at a density of $6\times10^5$ cells/cm$^2$ (high density seeding) or $1.2\times10^5$ cells/cm$^2$ (low density seeding), with medium change every alternate day. Periventricular endothelial cells were cryopreserved after at least one passaging in freezing medium composed of 90% periventricular endothelial cells medium and 10% DMSO. As a source of neurons, we used human iPSC-derived GABAergic neurons from Cellular Dynamics (Madison, WI, Cat #R1013). As control for microarray analysis and for cell migration assays, we used human-iPSC derived endothelial cells from Cellular Dynamics (Madison WI, Cat #R1022), whose gene expression profile is similar to human aortic endothelial cells (HAECs; https://fujifil-medi.com/assets/CDI130925MIPTEC04.pdf). The human GABAergic neurons and human HAEC-like endothelial cells were cultured using the manufacturer's protocol. Cell Lines were routinely tested for mycoplasma contamination using a Mycoplasma Detection Kit (InvivoGen, San Diego, CA). Cells used in this study were verified to be mycoplasma free before undertaking any experiment with them.

Periventricular endothelial cell isolation by fluorescence activated cell sorting (FACS): On day 7 of differentiation, cells were dissociated with Accutase and filtered through a 35 μm nylon mesh cell strainer cap to obtain a single cell suspension. Cell suspension was washed with ice-cold FACS buffer (2% FCS and 0.1% NaN$_3$ in PBS) and incubated with Fcγ blocker (BD Biosciences Pharmingen, 1 μg/ml) for 30 min. Cells were then washed in ice-cold FACS buffer and stained with PE/Cy7 anti-human CD31 antibody (BioLegend, Cat #303117) and anti-human GABRB3 antibody (Creative Diagnostics, Cat #DCABH-10376) conjugated with APC using an antibody conjugation kit (Abeam) for 1 hr. Cells were washed in ice-cold FACS buffer and CD31$^+$GABRB3$^+$ endothelial cells were isolated by fluorescence-activated cell sorting using a BD FACS Aria-II flow cytometer (BD Biosciences, San Jose, CA).

Gene expression profile analysis: Total RNA was extracted using the RNeasy plus minikit (Qiagen) according to manufacturer's instruction. RNA quality was determined using nanodrop and an Agilent 2100 bioanalyzer. Microarray hybridization was performed using the Human Gene Array 2.0ST gene chip (Affymetrix) at the Boston University Microarray and Sequencing Resource (BUMSR) Core, Boston, MA. Principal component analysis (PCA) was performed after normalizing gene-level expression values from CEL files of Affymetrix human gene 2.0 ST arrays by using the implementation of the Robust Multiarray Average (RMA) in the Affymetrix transcriptome analysis console (TAC) (v4.0.1, Applied Biosystem, Foster City, CA, USA). For exploratory group analysis, a Volcano plot, and a hierarchical clustering heatmap using TAC software were created after curating with a threshold parameter, 1.5-fold expression, $P<0.05$, FDRq<0.1. Relative Log Expression (RLE) and Normalized Unsealed Standard Error (NUSE) using the affyPLM package (version 1.34.0) and differential expression were assessed using the moderated (empirical Bayesian) t-test implemented in the limma package (v 3.14.4)[44]. Heatmap visualization was performed using Morpheus (Broad Institute, Boston, MA, USA). Violin plot visualization for expression level comparison of samples was generated with the log 2 expression value using GraphPad Prism v8.0 (GraphPad Software, La Jolla California USA). The gene ontology for gene enrichment study, was performed in three GO TERM annotation categories by using the Database for Annotation, Visualization and Integrated Discovery (DAVID) v6.8 with modified Fisher's exact test[45] and was visualized using GraphPad Prism software.

Tube formation assay: For the Matrigel-based tube formation assay, 10$^5$ periventricular endothelial cells (at passage number P2 or P3) were suspended in 400 ul of periventricular endothelial cells medium and seeded in one well of 24-well culture plates precoated with growth factor-reduced Matrigel (BD Biosciences). Cells formed tubular structures within 24 hours which were imaged using light microscope. The ability of periventricular endothelial cells to form tubes in 3D was assessed using the Fibrin Gel In Vitro Angiogenesis Assay Kit (Chemicon). 5×10$^5$ cells per ml of medium were seeded in one well of a 24-well plate coated with a fibrin matrix as described by the manufacturer. After 24 hours, cells were covered with a second layer of fibrin and fresh medium added. Capillary tube networks formed inside the fibrin gel within two days and were imaged using a light microscope.

Sprouting assay: Sprouting of periventricular endothelial cells was observed using a fibrin gel bead assay. Briefly, 10$^6$ periventricular endothelial cells (at passage P2 or P3) were coated onto 2500 Cytodex beads and allowed to attach overnight. Next day, beads were embedded in fibrin gels in 24-well culture plates (500 beads/ml), and human primary lung fibroblasts (ATCC) were plated on top of the gel (20,000 fibroblasts/well). Budding and sprouting of endothelial cells from the beads were observed from day 2 onwards and lumen formation was visible from day 4.

Long-distance migration assay: In preparation for migration assays, two-well silicone culture inserts (from ibidi GmbH, Cat #80209) were converted into one-well inserts by cutting with a sharp, sterile blade. Individual one-well inserts were placed in the middle of a 35 mm dish coated with Poly-Ornithine and Laminin. The boundary of the insert was marked on the back of each dish with a thin marker. For this assay, periventricular endothelial cells, control endothelial cells and endothelial cells derived without GABA and WNT7A were used at passage number P2 or P3, while GABA interneurons cultured for six weeks were used. 10$^4$ periventricular endothelial cells or endothelial cells derived without GABA and WNT7A were seeded in each insert in periventricular endothelial cell medium without GABA. Same number of GABAergic interneurons or control endothelial cells were seeded per insert in their respective manufacturer's recommended medium. The insert was removed after 48 hours and cells cultured for five days. After 5 days, cells were fixed and fluorescently labeled with an anti-human CD31 antibody (for endothelial cells) or an anti-human β-Tubulin antibody (for neurons) and DAPI. The distance between each cell body and the edge of the insert-boundary was measured using ImageJ.

Co-culture migration assay: Periventricular endothelial cells or control endothelial cells at passage number P2 or P3, and GABA interneurons cultured for six-weeks were used for this assay. 3×10$^4$ GABAergic interneurons and 3×10$^4$ periventricular endothelial cells were co-suspended in 70 ul of co-culture medium (50% PVEC medium without GABA and 50% GABA neuron maintenance medium from Cellular Dynamics) and seeded in a one-well insert (prepared as described above) in a poly-Ornithine/Laminin coated 35 mm dish. As control, 3×10$^4$ GABAergic interneurons only or 3×10$^4$ GABAergic interneurons and the same number of control endothelial cells were co-seeded. Inserts were removed after 2 days, and co-culture was maintained for five days. After 5 days, cells were fixed and double-labeled with anti-human CD31 and anti-human β-Tubulin antibodies. Neuronal migration was assessed by measuring the distance travelled by β-Tubulin$^+$ neurons from the day 0 mark using ImageJ software.

Chemo-attractivity assay: For this assay periventricular endothelial cells at passage number P2 or P3, control endothelial cells at passage P2, and GABA interneurons cultured for six weeks were used. Three-well culture inserts (ibidi GmbH, Cat #80369) were placed in the center of poly-Ornithine/laminin coated 35 mm dish. 3×10$^4$ GABA neurons were seeded in the center well. Equal number (10$^4$ cells) of periventricular endothelial cells and control endothelial cells were seeded in the two side wells. The inner edge of the neuronal well was demarcated at the back of the dish using a thin sharpie. Inserts were removed one day post-seeding, and cells were fixed after 36 hours. Cells were double labeled with anti-human CD31 and anti-human β-Tubulin antibodies and imaged. The chemo-attractive response of β-Tubulin$^+$ neurons towards endothelial cells in each experiment were imaged and quantified using a scoring scheme modified from Won et al.[13].

Migration assays with chemicals: To assess the roles of GABA or SDF-1/CXCL12 signaling on migration of human periventricular endothelial cells, $10^4$ cells were seeded in one well insert and allowed to migrate in the presence of respective agonist or antagonist in periventricular endothelial cell medium (without GABA). After five days, cells were fixed, stained with anti-human CD31 antibody (Millipore), imaged and the distance migrated was calculated using ImageJ. To examine the effect of endothelial GABA or endothelial SDF-1/CXCL12 signaling on interneuron migration, human periventricular endothelial cells were seeded in 35 mm dish ($10^5$ cells/cm$^2$) and incubated with respective chemical for a period of 48 hours. $3 \times 10^4$ GABAergic interneurons were seeded on top of the periventricular endothelial cells using a one-well insert, and allowed to migrate over the pre-incubated periventricular endothelial cells for 2 days. Migration of neurons was assayed by staining with anti-human β-Tubulin antibody (Biolegend) and imaged. The concentration of chemicals used in the assays are as follows: muscimol (Sigma) 100 uM, BMI (Sigma) 100 uM, AMD3100 (Sigma) 50 μM, recombinant human SDF-1α (Peprotech) 40 nM. The chemicals were kept at −20° as concentrated stock solutions and diluted on the day of the experiment.

Animals: Adult NOD-SCID mice (8 weeks old) were purchased from Charles River Laboratories, MA. Tie2-cre mice and Gabrb3 floxed (Gabrb3$^{fl/fl}$) mice were obtained from Jackson Labs. The Tie2-cre transgene is known for uniform expression of cre-recombinase in endothelial cells during embryogenesis and adulthood[14, 15]. To selectively delete Gabrb3 in endothelial cells, Tie2-cre transgenic mice (males) were crossed to Gabrb3$^{fl/fl}$ mice (females) to generate Tie2-cre; Gabrb3$^{fl/+}$ mice (males). These were further crossed with Gabrb3$^{fl/fl}$ mice (females) to obtain the Gabrb3 conditional knock-out (Tie2-cre; Gabrb3$^{fl/fl}$ mice). Animal experiments were in full compliance with the NIH Guide for Care and Use of Laboratory Animals and were approved by the McLean Institutional Animal Care Committee (IACUC).

Stereotaxic surgery and cell transplantation: NOD-SCID mice, Gabrb3$^{fl/fl}$ mice and Gabrb3$^{ECKO}$ mice were housed on a 12 h light/12 h dark cycle and had free access to food and water throughout the study. 8 weeks old mice were used for all transplantations. Cells for transplantation were suspended in transplantation medium composed of DMEM/F-12 with no phenol red (Thermo Fisher Scientific), BDNF (10 ng/ml, Peprotech), GDNF (10 ng/ml, Peprotech), Rock-Inhibitor (10 uM), and Boc-Asp(OMe) fluoromethyl ketone (20 uM, Cayman Chemicals). For co-transplantation, periventricular endothelial cells or control endothelial cells derived without WNT7A and GABA (at passage P2 or P3; 50,000 cells/ul) and GABAergic interneurons (at 6 weeks of differentiation; 50,000 cells/ul) were suspended in a 1:1 ratio. For interneuron-only or endothelial cell-only transplants, cells were suspended at a concentration of 50,000 cells/ul. Before surgery, mice were anesthetized with 4% isoflurane, and kept under 2% isoflurane gas throughout the procedure. All microinjections were performed through a pulled borosilicate glass pipette with a long, gently tapering shank using an UMP microsyringe pump (World Precision Instruments) and a Kopf stereotaxic frame (Kopf Instruments, CA). 1 μL of cell solution were injected at a rate of 0.125 μL/min. After each injection, the microcannula remained in position for 5 min before withdrawing slowly to avoid back-flow of cells. Injection coordinates were: for striatum-bregma: 0.49 mm, ventral: −3.0 mm, lateral: −1.8 mm; for neocortex-bregma: 0.49 mm, ventral: 1.8 mm, lateral: 2.0 mm. Transplanted Gabrb3$^{ECKO}$ mice received subcutaneous injections of cyclosporine (35 ul of 50 mg/ml stock, Perrigo), beginning two days before surgery, and continuing every day until mice were sacrificed. Transplanted mice were terminally anesthetized with a Ketamine/Xylazine cocktail (100 mg/kg and 10 mg/kg, respectively) and perfused intracardially with cold 4% formaldehyde for cryo-processing and immunohistochemistry (IHC), or with a zinc fixative (BD Biosciences Pharmingen) for paraffin histology and IHC.

Immunohistochemistry (IHC): For frozen section IHC, PFA-perfused brains were post-fixed in cold 4% formaldehyde for 48 hours, cryo-protected in a sucrose gradient, flash frozen in dry ice, and cryo-sectioned into 40 μm coronal sections. For immunostaining, sections were washed once with PBS, blocked in FBS containing 0.5% Triton X100 for 1 hour, and incubated with the primary antibody overnight at 4° C. The following day, slides were washed six times with PBS at room temperature, incubated with secondary antibodies (Alexa-568 and Alexa-488, 1:400) for 2 hours at room temperature, washed with PBS six times, and mounted onto slides with a DAPI-containing mounting medium (Vectashield). For paraffin IHC, brains were post fixed in Zinc fixative (BD Biosciences Pharmingen) for 48 hours, dehydrated in an alcohol gradient (70%, 80%, 95%, 100%), cleared in Xylene, embedded in paraffin wax, and sectioned into 8 um coronal sections. Prior to immunostaining of paraffin sections, tissue was deparaffinized and antigen retrieval was performed in a pH 9 solution (DAKO) at 96° C. Primary antibodies used for IHC were as follows: anti-human CD31 (1:100, Biolegend), anti-human vWF (1:100, Sigma), anti-human nuclei (1:100, Rockland), anti-human mitochondria (1:100, Millipore), anti-human β-TUBULIN (1:2000, Biolegend), anti-GABA (1:1000, Sigma), anti-GABRB3 (1:200, Sigma), anti-Caspase (1:50, Millipore), anti-Claudin5 (1:200, Sigma), anti-human Ki67 (1:50, Thermo Fisher Scientific), anti-ZO-1 (1:400, Thermo Fisher Scientific), isolectin B4 (1:50, Sigma), anti-NKX2.1 (1:250, Abcam), anti-OCT4 (1:200, SCBT), ant-TRA1-60 (1:200, Millipore). The secondary antibodies used were Alexa-594 and Alexa-488 (1:400, Thermo Fisher Scientific).

Immunocytochemistry: Cells were grown to 70-80% confluency on coverslips, fixed in 4% PFA for 15 minutes at room temperature, blocked in blocking solution (PBS supplemented with 1% Bovine Serum and 0.25% Triton X) for 1 hour at room temperature, and incubated with the primary antibodies overnight in 4° C. Next day, cells were stained with a secondary antibody (Alexa-594 or Alexa-488, 1:500, Thermo Fisher Scientific) for 2 hours at room temperature and mounted using ProLong™ Diamond Antifade Mountant with DAPI (Thermo Fisher Scientific). The primary antibodies were same as that for IHC and used at same dilutions (mentioned above), except for anti-human CD31 which was purchased from Millipore and used at a dilution of 1:100.

H and E staining: Brains were post fixed in a Zinc fixative (BD Biosciences Pharmingen) for 48 hours, dehydrated in an alcohol gradient (70%, 80%, 95%, 100%), cleared in Xylene, embedded in paraffin wax, and sectioned into 8 um coronal sections. Briefly, slides were deparaffinized in Xylene, hydrated in ethanol gradient (100%, 95%, 70%), rinsed in tap water, stained with Hematoxylin for 1 minute, rinsed again in tap water, stained in Eosin for 30 secs, dehydrated in an ethanol series (70%, 95%, 100%) followed by xylene, and mounted onto glass slides in permount (Sigma).

Figure 1G:
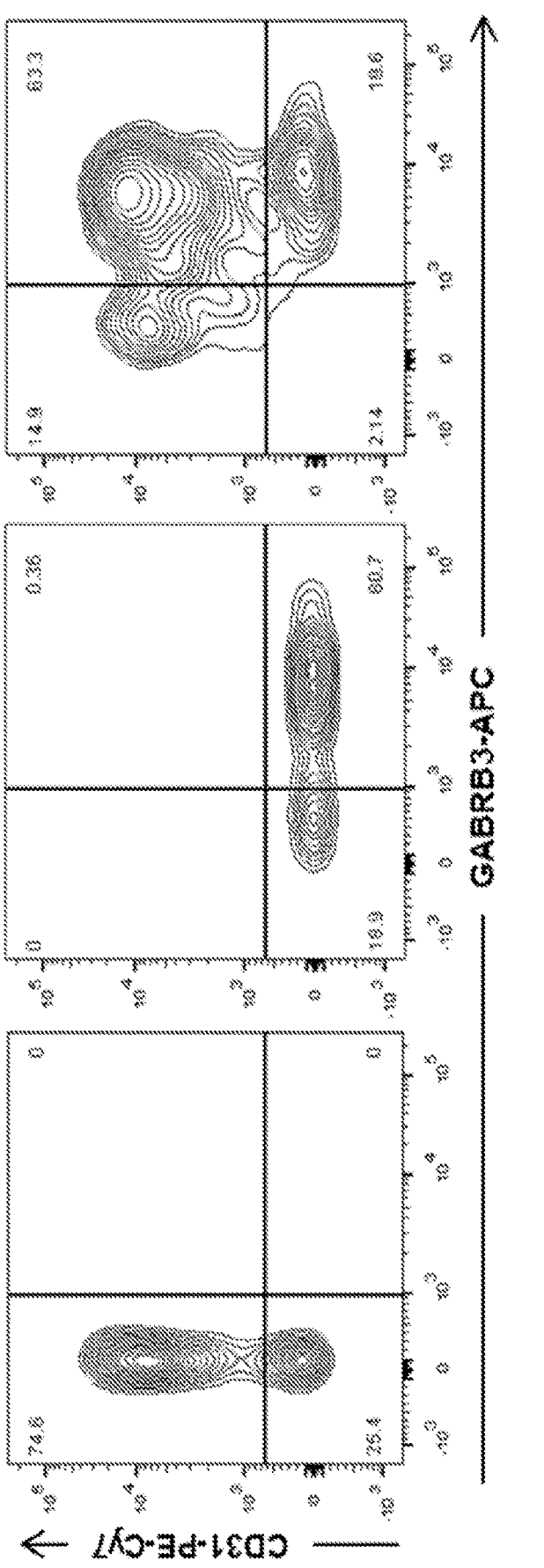
Figure 1H:
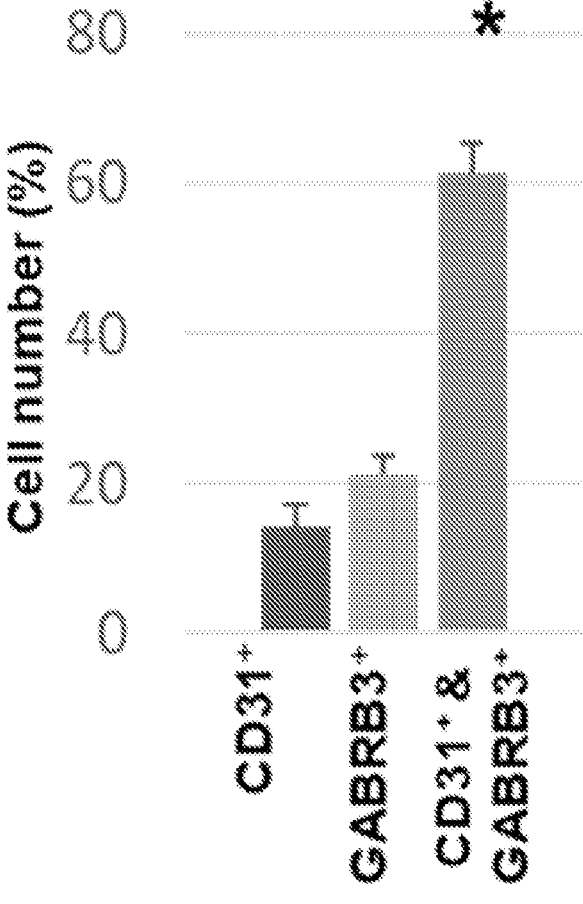

Microscopic analysis and cell counting: Twenty sections from each brain were used for IHC and histology experiments. All low and high magnification images were obtained with a FSX100 microscope (Olympus). Counting of human nuclei+ cells in each type of transplant was performed using ImageJ. The number of transplanted neurons that had migrated into the cerebral cortex was obtained by counting human nuclei+ and β-tubulin+ cells using the ImageJ software. Blinding was performed during cell counting analysis.

Behavioral experiments: All behavioral tests were done during the light phase of the light/dark cycle. Before behavioral testing, mice were acclimatized to the testing room for 1 hour. Behavioral assays were performed according to established protocols referenced here: nest building with shredded paper[46], self-grooming[47], light-dark box[48], tail suspension test[49], and three-chamber social interaction test[50]. Both males and females were used for all behavioral assays. Experimenters scoring behaviors were blinded to the genotypes. Results were analyzed using Student's t-test, and one-way ANOVA. Data is presented as mean±standard deviation. Values of $p<0.05$ were considered statistically significant.

ELISA: ELISA was used to detect and compare GABA levels released from human interneurons-only, human periventricular endothelial cells-only and periventricular endothelial cells-neuron co-culture. Periventricular endothelial cells-only and interneuron-only cultures were prepared by seeding cells in a 12 well plate at a density of $10^5$ cells/cm$^2$. The endothelial and interneuron co-culture was prepared by co-seeding both cells at a 1:1 ratio with a final density of $10^5$ cells/cm$^2$. Supernatants from cells were collected after 96 hours and stored at −80° C. GABA concentrations were quantitatively determined by competitive ELISA according to the manufacturers' protocol (GABA Research ELISA kits, Labor Diagnostica Nord, Germany), and absorbance was measured using a multiplate microplate fluorescence reader (Molecular Devices, CA) at 450 nm.

Quantitative real-time PCR: Total RNA was prepared using the RNeasy plus minikit (Qiagen). cDNA from total RNA was generated using the SuperScript™ III First-Strand Synthesis System (Thermo Fisher Scientific) as per manufacturer's protocol. PCR reactions were run on a CFX96 Touch Real Time PCR (Bio-Rad) with SsoAdvanced™ Universal SYBR® Green Supermix (Bio-Rad). Primers for qPCR were obtained from Thermo Fisher Scientific. The relative expression level for each gene was normalized to that of GAPDH gene and subsequent fold changes were determined according to published methodology[51].

Western Blot: Cell lysates were prepared in standard radioimmunoprecipitation (RIPA) buffer containing 1× protease Inhibitor cocktails, and protein was quantified using Bio-Rad protein quantification assay. Cell lysates were then separated in a 12% gel and immunoblotted onto a nitrocellulose (NC) membrane using the NOVEX SDS electrophoresis unit. Membrane was blocked for 1 hour at RT using the Odyssey blocking buffer (Licor), and incubated with primary antibodies; anti-CD31 (Thermo Fisher) and anti-VE-cadherin (Sigma) and anti-GAPDH (Proteintech) overnight at 4° C. Next day, membranes were washed and incubated with secondary antibodies, anti-mouse IRD 800 and anti-rabbit IRD 680 for 1 hour at RT in dark. Fluorescent signal was detected using Licor detection system and data analyzed using the lmageLite studio software.

Statistical analysis: All statistical analyses were performed using GraphPad Prism 7 (GraphPad Software, La Jolla CA). Power analysis was performed using Java Applets for Power and Sample size. Simple random sampling was used. Sample sizes assigned to the same experimental groups were equal. The exact sample size (n) for each experimental group is reported in individual figure legends. For in vitro assays, the number of cells examined, is mentioned in respective methods sections. For histology and IHC experiments, twenty sections from each brain were used for each experimental group. Uniform penetration of antibodies or stains throughout the section was ascertained and quality of the staining in each digital section was examined. Only those sections which showed uniform labeling were included in further analysis. Blinding was used during cell counting analysis and behavioral experiments. No data were excluded. Statistical significance of differences between groups was analyzed by two-tailed Student's t test (Prism; GraphPad software) and has been noted in individual figure legends. Significance was reported at $p<0.05$.

Example 1. Efficient Generation of Human Periventricular Endothelial Cells From Human Embryonic Stem Cells Brain endothelial cells have been derived from human pluripotent stem cells previously[39-42], but their analysis, gene expression studies and functions have largely focused on the blood-brain barrier attributes. Generation of embryonic forebrain specific periventricular endothelial cells has not been reported so far. Periventricular endothelial cells show enrichment in genes controlling neurogenesis, neuronal migration, chemotaxis, and axon guidance and can be distinguished from other endothelial cells by their specific transcription factor expression, signaling molecules and extracellular receptors[12-15]. Indeed, this specific population of endothelial cells houses a novel GABA signaling pathway that is distinct from the classical neuronal GABA signaling pathway in the embryonic forebrain. Vasculature is autonomous with respect to anatomy, patterning, gene expression, developmental regulation and function in different organs and/or regions at different time points. Developing strategies to generate embryonic forebrain-like vasculature will augment its region-specific vessel growth and function after transplantation and will be important for clinical applications. Based on our knowledge of gene expression of mouse periventricular endothelial cells of the embryonic forebrain, we first established a differentiation strategy to generate human periventricular endothelial cells from human ES cell lines (FIGS. 1A-C, FIGS. 6A-G, FIGS. 7A-F, FIGS. 8A-I, FIGS. 9A-I). The strategy was initially implemented using the human ES cell line H9, and robustness of the protocol was subsequently validated with the human ES cell line H1. From day 0-2 of differentiation, mesodermal cell fate was induced in H9 cells by culturing them in E8 media supplemented with bone morphogenetic protein 4 (BMP4), Activin A, and CHIR 99021 (small molecule activator of WNT pathway). From days 2-5, vascular induction was promoted by inhibiting TGFβ signaling (using the small molecular inhibitor SB431542) and by addition of vascular endothelial growth factor-A (VEGF-A). Since periventricular endothelial cells express Wnt7a and GABA, we added these components to the differentiating medium. A combination of WNT7A protein and low concentration of GABA (5 μM) from days 0 to 5 in the differentiating medium was critical for tight junction formation and production of endogenous GABA in these endothelial cells (FIGS. 6A-G, FIGS. 7A-F). Interestingly, higher levels of GABA (50 uM or 100 μM) disrupted the localization of tight junction proteins Claudin 5 and ZO-1, alluding to a correlation between GABA level and tight junction formation in periventricular endothelial cells (FIGS. 6D-I). Addition of WNT7A and GABA also significantly increased expression of transcription factors Pax6, Dlx1, Dlx2, Nkx2.1, tight junction component Claudin 5, Vegf receptor Flk1, cell-cell adhesion molecule Cd31 and chemokine 12 or Cxcl12 (also known as stromal cell-derived factor 1 or SDF1) and SDF1 receptor Cxcr4, (FIGS. 8A-I). Immunocytochemistry and western blotting data illustrate the importance of WNT7A and GABA co-addition in the differentiating medium for CD31 and VE-Cadherin expression (FIG. 1D, FIGS. 9A-I) in periventricular endothelial cells. From day 5 of differentiation, endothelial-like cells were observed in the differentiating cell population that expressed markers CD31 and vWF (FIGS. 1E, F). Of importance, on day 7, differentiated CD31+GABRB3$^+$ cells (>60% of total differentiated cells) were isolated by fluorescence activated cell sorting (FACS) (FIGS. 1G, H) and were further maintained in endothelial cell culture medium containing VEGF, FGF2 and GABA.

Figure 10:
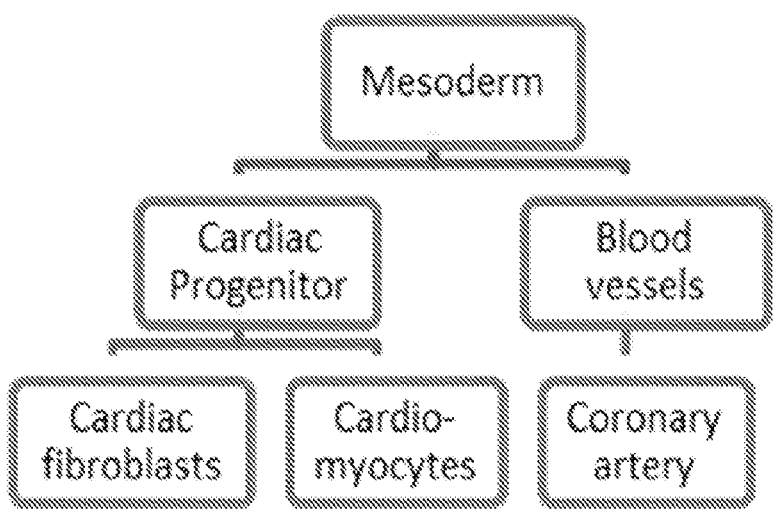
Figure 11:
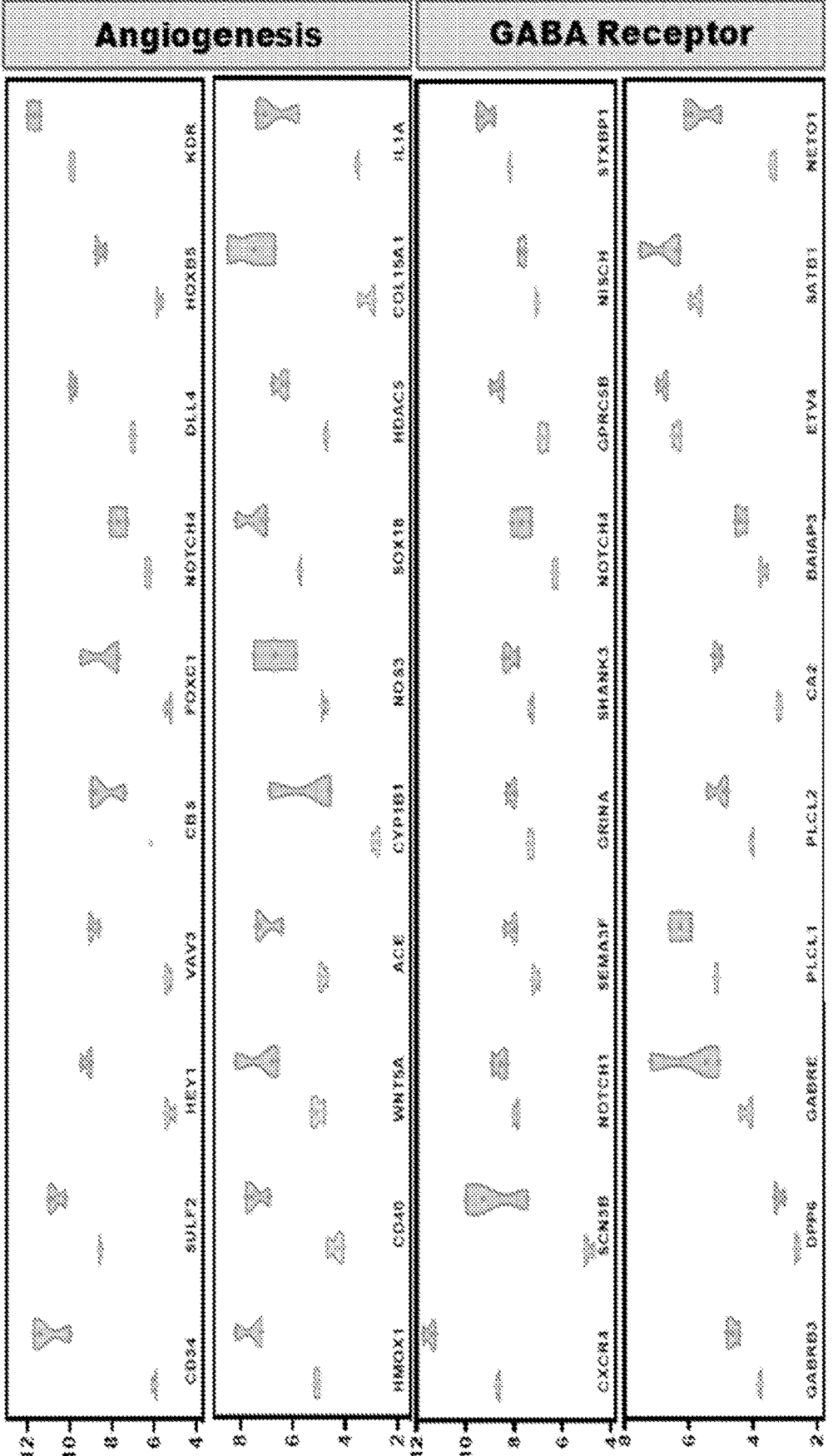
FIG. 11. Differentially expressed gene categories in human periventricular endothelial cells (PV ECs) versus control endothelial cells (ECs). Violin plot shows 5 specific categories of genes that are up- or down-regulated significantly in human PV ECs (right hand symbol) versus control ECs (left hand symbol). Expression levels in Y-axis are represented as binary logarithm (log 2) value. Each category is indicated on the right side. Differential expression of each gene between control ECs and human PV ECs is P<0.05.
Figure 12A:
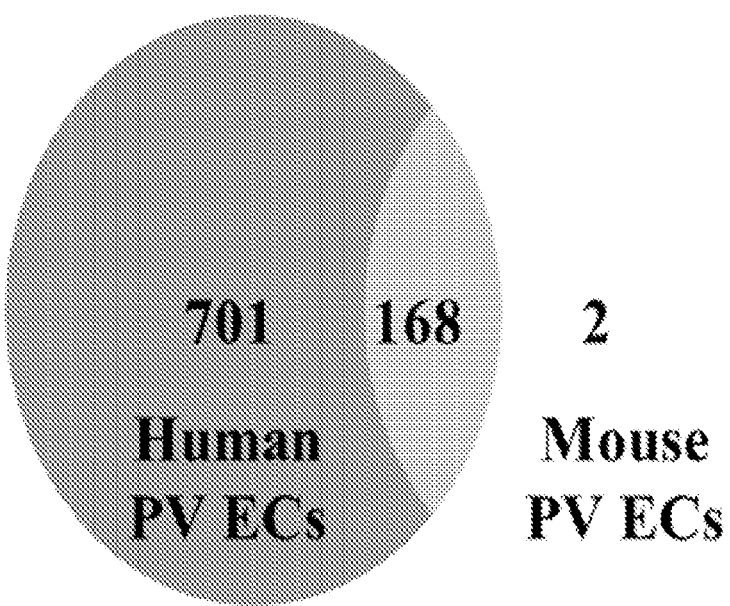
FIGS. 12A-B. Gene expression overlap between mouse and human periventricular endothelial cells. (a, b) Venn diagrams depict a significant overlap of genes related to categories—blood vessel development (a) and GABA pathway (b) between mouse periventricular endothelial cells (PV ECs) and human PV ECs.
Figure 12B:
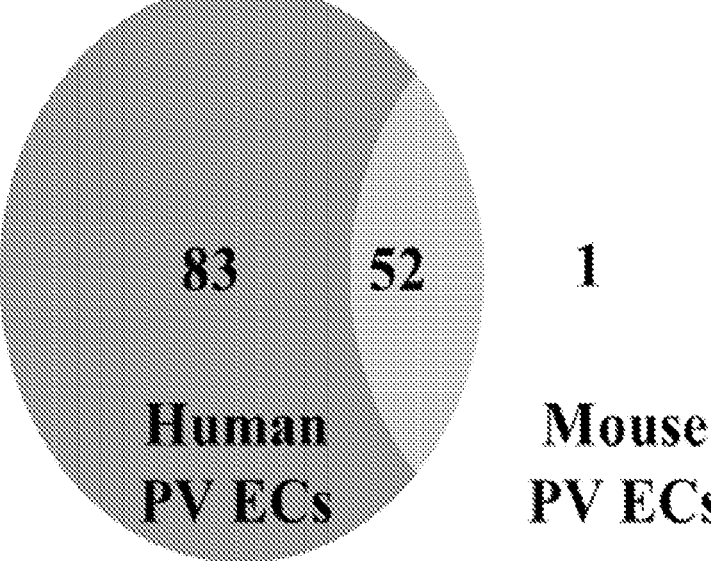
Figure 13A:
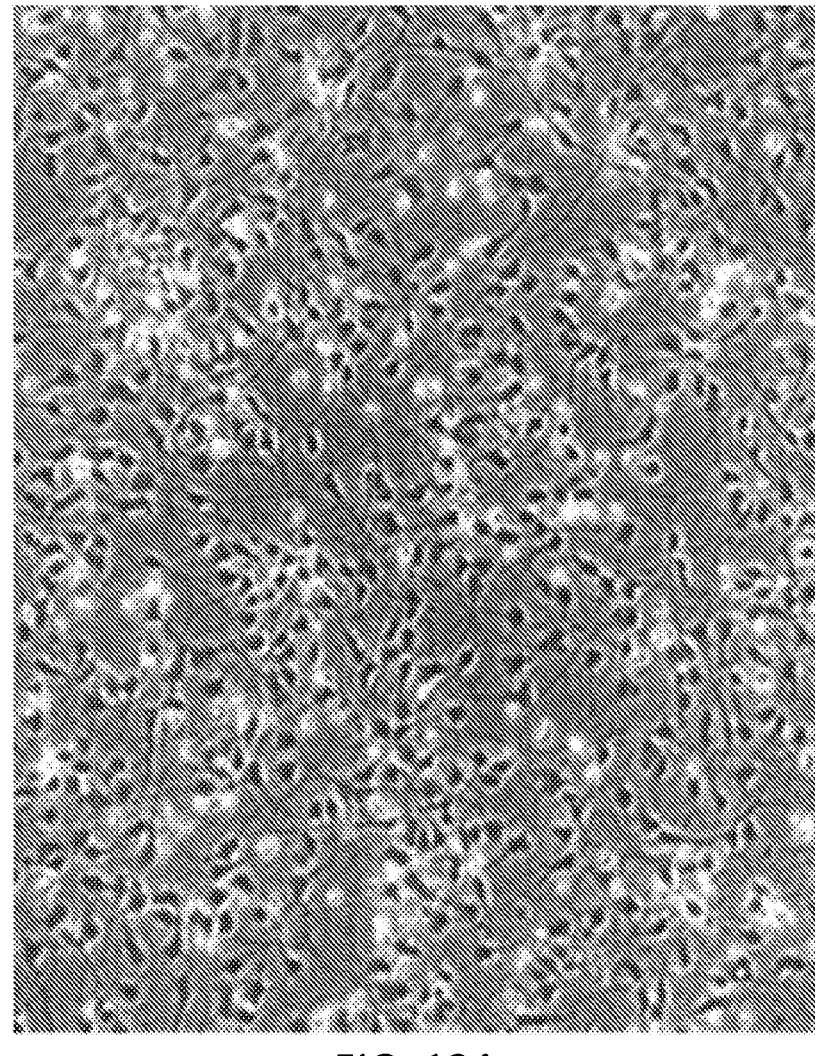
FIGS. 13A-F. Morphology and gene expression profiles of human GABAergic interneurons. (a) Phase contrast image of GABAergic interneurons that were cultured for 2 weeks after thawing. (b) RNA-seq data showing expression levels of interneuron-subtype specific markers: parvalbumin (PVALB), calbindin1 (CALB1), calbindin2 (CALB2), calretinin (CR), somatostatin (SST), vasointestinal protein (VIP), neuropeptide Y (NPY) and cholecystokinin (CCK). RNA-Seq libraries were made and run on Illumina HiSeq 2000 instrument. (c-f) Relative gene expression of different regional and neural subtype markers in GABAergic interneurons.
Figure 13B:
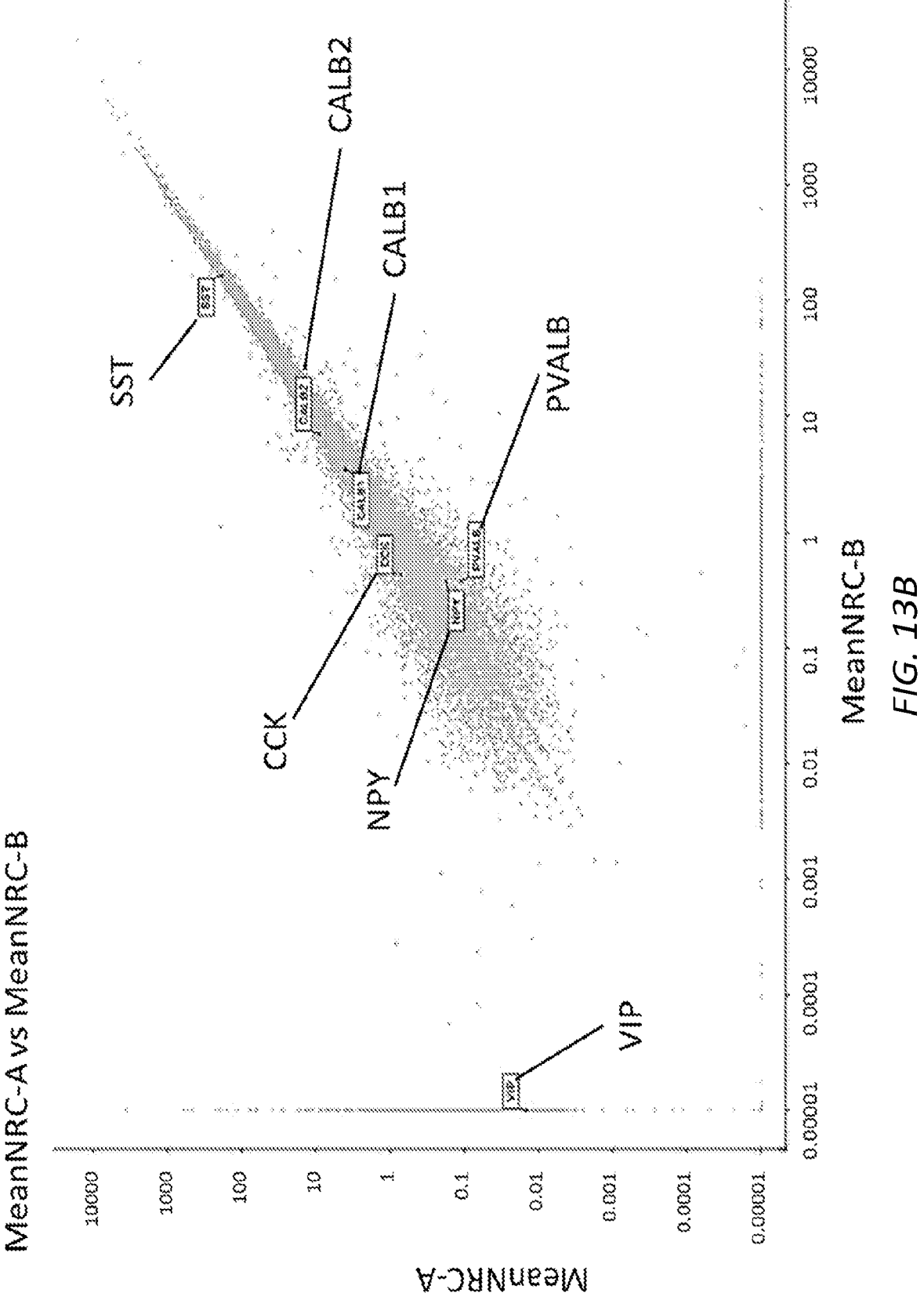
Figures 13C, 13D, 13E, 13F:
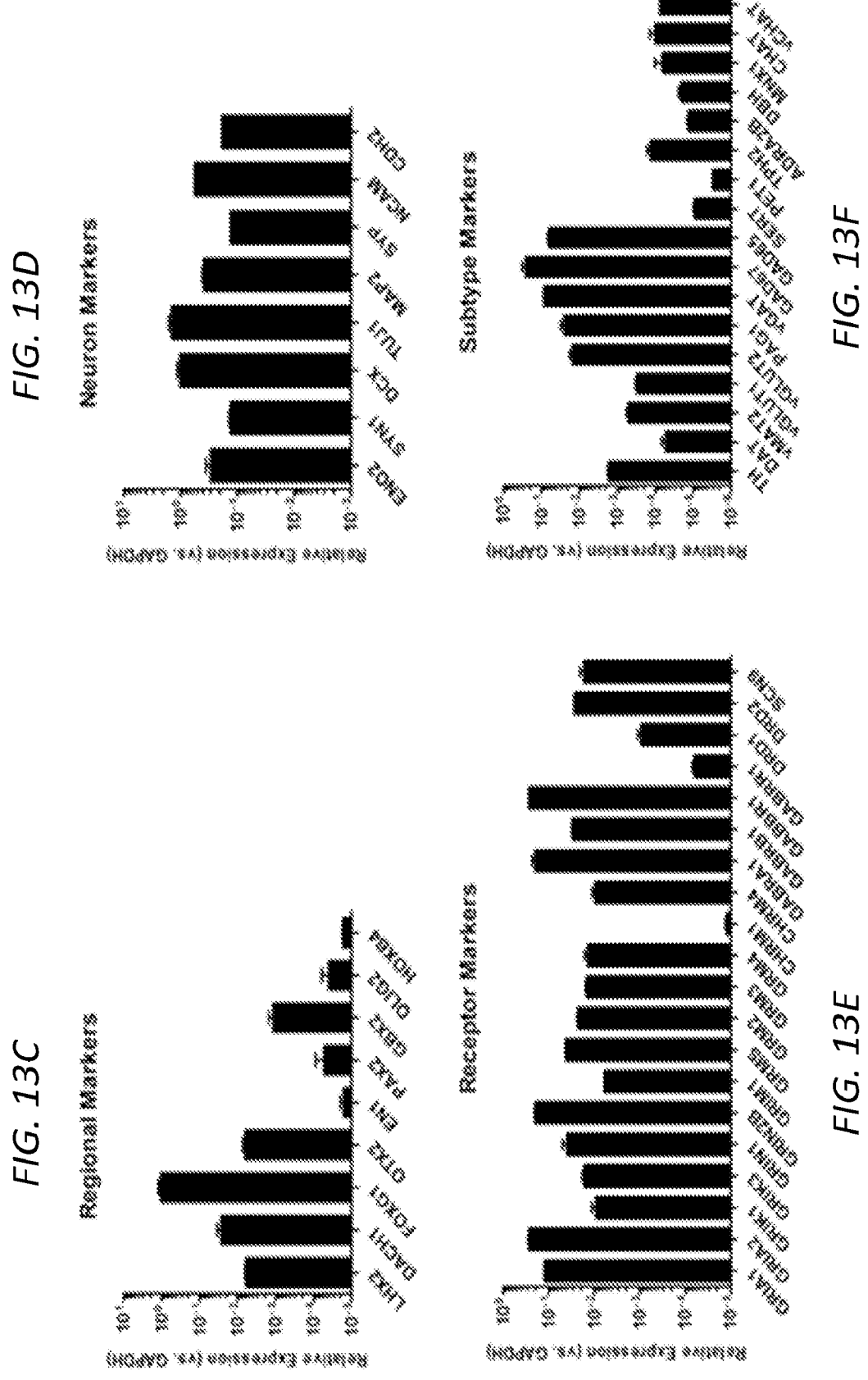

To test the efficacy and specificity of our differentiation protocol, we performed microarray analyses of H9 ES cells, molecular signature[12-15]. A clear separation between periventricular endothelial cells and control endothelial cells was observed along the PCA axis with respect to gene expression and gene ontology categories depicting biological processes. Fate mapping further confirmed the cardiac fate of control endothelial cells (FIG. 10). A violin plot portrays differential gene expression of top genes in several categories (angiogenesis, GABA receptor, transcription factor, tight junction and Wnt signaling) in periventricular endothelial cells versus control endothelial cells (FIG. 11). We also compared the gene expression profile of human periventricular endothelial cells with mouse periventricular endothelial cells and found a significant overlap in common blood vessel development and GABA pathway related genes (FIGS. 12A-B). Common genes that are expressed in mouse PVECs and human PVECs in (FIG. 12A) and (FIG. 12B) are listed in Table 1 and Table 2 respectively.

TABLE 1

| Common blood vessel development genes expressed in mouse and human PVECs |
| --- |
| MMP2, COL3A1, CADM4, CSPG4, FLT1, ALOX12, TBX4, KRIT1, RORA, ANGPTL4, LEP, GPNMB, FOXC2, TGM2, ADCYAP1, NTRK2, NOS1, SMO, COL1A1, SLC8A1, ISL1, PRKG1, CLEC14A, ADRA2B, PAX6, SCG2, PIK3CG, THSD7A, DYSF, EGFR, DPP4, HTR7, CD38, THBS4, GPR4, MAPKAPK3, COL15A1, GATA6, FZD5, SGPL1, EMP2, F2RL1, OSR1, DDAH1, FGG, PDGFA, SEMA3E, WDR35, C3AR1, MEOX2, ATF2, HK2, APOD, ADRA2A, CX3CL1, NCKAP1L, EDNRA, CALCRL, FGF18, CD40, PIK3R2, LTBP1, STK4, LIF, NRP2, LRP2, ITGA1, APLN, HRH1, DBH, DNM2, CHGA, DLL1, STRA6, RUNX1, ALDH1A2, KCNA5, P2RX1, ECM1, HOXA3, HIF1AN, TNFSF12, FN1, AHR, NR2E1, ADORA2B, PIK3R3, TAB1, PRRX1, HTR1D, MAPK11, AQP1, LEPR, CXCL10, BMP6, SERPINE1, ZFPM2, PTAFR, ROBO2, PDGFRB, STC1, LOX, TGFBR3, IL1A, CCR2, FYN, EDN3, VEGFC, NRCAM, HIPK2, LRG1, AKT1, GPC3, ANTXR1, PDGFRA, ADM, PCSK5, CCBE1, SEMA4A, PTGS2, BMP7, EDN2, CLDN1, HAS2, SIX1, ITGB3, CDC42, VTN, SEMA5A, BMP2, BMP4, MCAM, RSPO3, COL5A1, DCN, COL8A2, ITGB8, PRICKLE1, CX3CR1, HPGD, VEGFA, LAMA1, MMP19, SOCS3, EPHB2, WNT7B, CYFIP2, AGTR2, BGN, COL1A2, PRKCA, BAIAP2, GHSR, EIF2AK3, COL8A1, IL6, SEMA3C, EPHX2, DLL4, GATA4, HMGA2, NR2F2, PRDM1, TMEM100, FGFBP1, ANGPT2, ESM1, ITGA4 | human periventricular endothelial cells (FIGS. 1I-L) and commercially available human iPSC-derived human aortic endothelial cell (HAEC)-like cells (see Materials and Methods) as control. We extracted RNA from cells of these three groups and performed microarray hybridization and analysis. A comparison of gene expression between H9 cells and human periventricular endothelial cells showed a distinct upregulation of angiogenesis related genes in human periventricular endothelial cells only, while H9 cells depicted an upregulation of embryonic stem cell related genes or markers of pluripotency (FIG. 1I). GSEA analysis also revealed an enrichment of angiogenesis gene sets in only periventricular endothelial cells, indicating the effectiveness of the differentiation. Next, we compared the gene expression of human periventricular endothelial cells with control endothelial cells (FIGS. 1J-L). This resulted in an upregulation of 1947 genes and a downregulation of 1873 genes in human periventricular endothelial cells versus controls. Specific angiogenesis related genes were significantly unregulated in periventricular endothelial cells versus control endothelial cells (FIG. 1J), further indicating the distinct nature of the two endothelial cell types. Additionally, gene expression that is specific to the central theme of forebrain development like GABA neuron development (FIG. 1K) and neurogenesis (FIG. 1L) was enriched in periventricular endothelial cells versus control endothelial cells, reflective of periventricular endothelial cells' unique

TABLE 2

| Common GABA pathway genes expressed in mouse and human PVECs |
| --- |
| LRRTM2, LRFN5, GAD1, GAD2, KRAS, GABRB2, GABRB3, GABRA5, BSN, CNTN2, GABRA2, CDH10, GAP43, ERC2, FEZF2, ASCL1, GABRB1, NPAS4, DLX2, GABRA1, DLX1, CNTNAP4, LRRTM1, SLITRK1, JAKMIP1, KCND3, NRXN1, CNR1, KCND2, LHX6, GABRA4, CALB1, ARX, PTPRO, SEZ6L2C, GABRG2, SLC32A1, PLCL1, NKX2.1, ERBB4, NRG1, PAX6, LHX1, SLC32A1, ISL1, CXCR4, CDK5R1, FOXG1, EMX2, ETV1, GABRA1, NETO1 |

Example 2. Cellular and Functional Characterization of Human Periventricular Endothelial Cells We further assessed the expression of periventricular endothelial cell markers in purified human periventricular endothelial cell cultures by immunocytochemistry. All H1-derived periventricular endothelial cells in culture (100%) expressed endothelial cell markers—CD31, (FIGS. 2A, C, E, F), von Willebrand Factor (vWF) (FIG. 2D) and co-labeled with periventricular endothelial cell markers, GABRB3 (FIGS. 2A-C), GABA (FIG. 2E), NKX2.1 (FIG. 2F), PAX6 and ISL1, similar to mouse periventricular endothelial cells. Pluripotent markers OCT4 and TRA1-60 were not present in any cell, confirming absence of undifferentiated cells in the periventricular endothelial cell population. Effective proliferation, migration, sprouting, alignment, branching, lumen formation, and anastomosis are key elements of angiogenesis. Therefore, we performed in vitro assays to demonstrate the angiogenic properties of human periventricular endothelial cells. These endothelial cells formed tubular networks within 24 hours of seeding on Matrigel (FIG. 2g), demonstrating high angiogenic capacity. Additionally, human periventricular endothelial cells formed tubular networks in a three-dimensional milieu when cultured within fibrin gel matrix demonstrating budding, branching and lumen formation (FIGS. 2H-J). Later stages of endothelial cell branching and fusion of vessels (anastomosis) were also observed (FIG. 2H-J). Sprouting of new capillaries from existing blood vessels is another hallmark of angiogenesis. We performed a fibrin gel bead assay for sprouting, in which periventricular endothelial cells were coated on cytodex beads and embedded in three-dimensional fibrin gels. Periventricular endothelial cells started budding and sprouting within two days (FIG. 2K). Within the next days, long tubular vessels with clear intercellular lumens were formed (FIGS. 2L, M). In addition to general angiogenic properties, periventricular endothelial cells possess some unique properties. First, periventricular endothelial cells themselves have the ability to migrate long distance. Second, periventricular endothelial cells induce long-distance migration of GABAergic interneurons. We tested these properties in human periventricular endothelial cells using in vitro chemo-attractivity and migration assays. We used human GABAergic interneurons (Cellular Dynamics; FIGS. 13A-F) that have been extensively characterized with respect to their morphological, electrophysiological and molecular characteristics in several neuroscience research models, as a source of neurons for these assays. Using three-well culture inserts (ibidi GmbH), we seeded human interneurons in a small rectangular patch on a 35 mm poly-ornithine/laminin coated culture dish. Equal numbers of periventricular endothelial cells and control HAEC-like endothelial cells (that do not have periventricular-specific gene expression; FIGS. 1J-L; FIG. 10; FIG. 11; FIGS. 12A-N) were seeded as patches on either side of the neuronal patch, with the gap between each patch being 500 μm (FIG. 2N). The number of interneurons that migrated towards periventricular endothelial cells versus control endothelial cells was quantitated after 36 hours. Interneurons showed significantly higher chemo-attractive response towards periventricular endothelial cells compared to control endothelial cells (FIGS. 2O-Q), confirming that human interneurons respond selectively to chemo-attractive cues secreted by human periventricular endothelial cells.

Figure 2V:
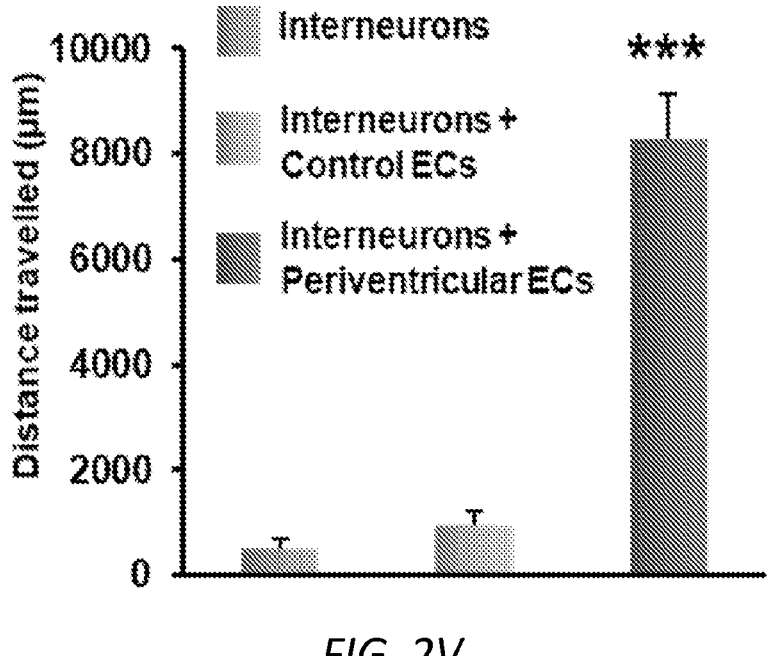

Next, we performed cell migration assays to test the long-distance migratory potential of human periventricular endothelial cells and its role in guiding human interneuron migration (FIGS. 2R-V). We compared the migration of periventricular endothelial cells with human interneurons, and with two types of control endothelial cells: a) HAEC like-human endothelial cells and b) endothelial cells derived from H9 cells in the absence of GABA and WNT7A (FIGS. 7A-F; FIGS. 9A-I; FIG. 10). Human periventricular endothelial cells seeded alone, travelled further distance compared to human interneurons or either set of control endothelial cells (FIG. 2U), confirming their cell-intrinsic capacity for long-distance migration. Also, for the same distance range, a higher percentage of periventricular endothelial cells migrated out than interneurons or control endothelial cells (FIG. 2U). To test the ability of human periventricular endothelial cells in facilitating human interneuron migration, we performed a co-culture migration assay where interneurons were co-seeded with human periventricular endothelial cells. Migration of co-seeded interneurons were compared to interneurons which were seeded alone, or seeded along with control human endothelial cells. When seeded along with periventricular endothelial cells, interneurons migrated significantly, both in terms of cell number and distance when compared to interneurons cultured along with control endothelial cells or interneurons alone (FIGS. 2R-T, V). Collectively, these data confirm the high angiogenic potential of human periventricular endothelial cells and its specificity with regard to instructing and promoting migration of human GABAergic interneurons.

Example 3. Co-Transplantation of Human
Periventricular Endothelial Cells With GABAergic
Interneurons Successfully Enhanced Neuronal
Migration In Vivo Next, we investigated whether human periventricular endothelial cells could facilitate human interneuron migration in vivo. To this end, we transplanted human periventricular endothelial cells along with human interneurons in a ratio of 1:1 into the striatum of adult NOD-SCID mice, on each side of the brain (FIG. 3A). The striatum provides a potentially powerful experimental system for studying cell migration and dispersion, with optimal cell survival after transplantation. One month after transplantation, histological staining was used to identify the graft (FIGS. 3B-E). Many cells were observed migrating out of the graft core into the host brain. To further investigate the migration pattern, we performed immuno-histochemistry and analysis in one-month old periventricular endothelial cell-interneuron co-transplanted brains. The staining patterns were compared to control NOD-SCID brains that had received (i) interneuron-only transplant, (ii) periventricular endothelial cells-only transplant, and (iii) interneuron+control endothelial cells that were derived without GABA and WNT7A. Grafted interneurons, double labeled with anti-human β-Tubulin, anti-human mitochondria and anti-human nuclei antibodies, revealed significant difference in migration pattern between transplanted brains. In interneuron-only and interneuron+control endothelial cell brains, most of the interneurons stayed within the graft site (FIGS. 3F-I, FIG. 3S). In contrast, in periventricular endothelial cells-only brain (FIG. 3J) and interneurons along with periventricular endothelial cells co-transplanted brain (FIG. 3K-M), cells migrated out from the graft site and spread widely in the striatum. Human periventricular endothelial cells were identified by anti-human vWF and anti-human CD31 labeling (FIGS. 3J, N, T, X). Labeling with anti-human CD31 and isolectin B4 revealed that new vessels formed by human periventricular endothelial cell transplantation were able to merge with host vessels (FIGS. 3O, O'). In the interneuron-only group and interneuron+control endothelial cell transplanted group, the majority of neurons remained stalled near the striatal graft site and only a limited number of grafted neurons were observed in the cerebral cortex (FIGS. 3P-S), indicative of failure of long-distance migration. Strikingly, in both the human periventricular endothelial cell group (FIG. 3T) and in the interneuron+periventricular endothelial cell co-transplanted group (FIGS. 3U-X), cells from the striatum were able to migrate long distance into several cortical areas, highlighting the enhanced migratory ability of human periventricular endothelial cells alone and along with interneurons. Immunostaining with anti-human NKX2.1 antibody indicated that grafted interneurons and periventricular endothelial cells continue to express NKX2.1 in the host brain (FIG. 3W). We quantified the percentage of human nuclei$^+$ cells, among total grafted cells, that had migrated into the cortex in all four transplanted groups. The cortex of interneuron plus periventricular endothelial cells transplanted brains had a significantly higher number of human nuclei$^+$ cells than either of the other groups (FIG. 3Y). Interestingly, periventricular endothelial cells-only cortex had almost double the number of grafted cells than interneuron-only cortex, showing that periventricular endothelial cells have a better migratory ability than interneurons or control endothelial cells in vivo (FIG. 3Y). Quantification of the neuronal number showed a significant increase in the number of interneurons in the cortex of interneuron+periventricular endothelial cell co-transplanted brains compared to interneuron-only brains and interneuron+control endothelial cell transplanted brains (FIG. 3Z). Cell death was minimal, as confirmed by double staining with anti-caspase and anti-human nuclei antibodies in all of our striatal transplantations. Taken together, these results show that human interneurons require human periventricular endothelial cells for long distance migration in vivo.

Example 4. Human Periventricular Endothelial Cell-Derived GABA Regulates Cell Migration GABA secreted from mouse periventricular endothelial cells plays both autocrine and paracrine roles. It enhances the migration of periventricular endothelial cells, triggers angiogenesis, and promotes robust migration of interneurons[13, 15]. We next studied whether GABA signaling from human periventricular endothelial cells also performed these functions (FIGS. 4A-F). GABA expression in human periventricular endothelial cells was qualitatively confirmed by immunostaining (FIG. 2E; FIG. 7L). In addition to expressing GABA, microarray analysis showed high level expression of chemokine receptor CXCR4 in human periventricular endothelial cells. CXCR4 and its ligand Stromal Derived Factor-1 (SDF1, also known as CXCL12) regulate cell migration in many developmental events. Therefore, we focused on both GABA and SDF-1/CXCR4 signaling pathways to delineate their role in the migratory events. To study their function in human periventricular endothelial cell migration, we performed a long-distance migration assay with endothelial cells in the presence of GABA$_A$ receptor agonist muscimol (100 μM), GABA$_A$ receptor antagonist bicuculline methiodide (BMI, 100 μM), human SDF-1 (40 nM) and CXCR4 receptor antagonist AMD3100 (50 μM). There was a significant increase in the number of migrating cells in the muscimol treated condition compared to control (no chemicals added) (FIGS. 4A-C). Correspondingly, there was a significant decrease in cell migration in BMI treated cells compared to control (FIGS. 4A, 4D). Addition of SDF-1 or AMD3100 produced no significant effect on endothelial cell migration (FIG. 4A). Next, we investigated the effect of these molecules on periventricular endothelial cell-mediated interneuron migration. Periventricular endothelial cells in culture were treated with the same agonists and antagonists for 48 hours. Interneurons were then seeded over these pre-treated endothelial cells and allowed to migrate for 48 hours. Interneurons co-cultured on muscimol-treated endothelial cells showed significantly higher migratory ability compared to control, while interneurons co-cultured with BMI-treated endothelial cells showed decreased migration (FIG. 4E). No discernible effect on interneuron migration was observed in SDF1 or AMD3100 treated conditions when compared to control (FIG. 4E). These results indicate that the SDF-1/CXCR4 signaling pathway may play other roles in periventricular angiogenesis, independent of cell migration. Using ELISA, we quantitatively analyzed GABA levels secreted from human periventricular endothelial cells and compared it with levels secreted from cultures of human interneurons and co-culture of both these cell types. Human periventricular cells secreted higher levels of GABA than human interneurons, while the co-culture of human periventricular endothelial cells and interneurons secreted the highest levels of GABA (FIG. 4F). Taken together these results show that, activation of the GABA$_A$ receptor pathway in human periventricular endothelial cells triggers GABA release that enhances endothelial cell migration, and mediates endothelial cell-guided chemoattractivity and migration of human interneurons.

Example 5. Rescue of Behavioral Symptoms in Gabrb3$^{ECKO}$ Mice in Four Weeks

In order to test the functional significance of co-transplantation of human periventricular endothelial cells with interneurons, when compared to interneuron-only transplants, we used a well-established pre-clinical model of psychiatric disorder—the Gabrb3 endothelial cell conditional knockout model (Gabrb3$^{ECKO}$ mice), in which there are both vascular and GABAergic interneuron deficits in the cingulate, motor, and somatosensory cortex[15]. The developmental dysfunction of endothelial GABA$_A$ receptors and reduction in endothelial GABA levels significantly impaired angiogenesis and GABAergic interneuron migration in the embryonic brain that persisted in the adult brain (FIGS. 4G, H) with lasting consequences for behavioral outcome[15]. These mice show behavioral dysfunction similar to psychiatric disease that is characterized by these core symptoms—depression, increased anxiety, communication deficits, impaired social recognition and reduced social interactions. Therefore, we transplanted interneurons only or co-transplanted human interneurons and periventricular endothelial cells into the somatosensory cortex of Gabrb3$^{ECKO}$ mice. As additional control groups, we transplanted human periventricular endothelial cells-only and interneurons+control endothelial cells (derived without GABA and WNT7A) into the Gabrb3$^{ECKO}$ somatosensory cortex. Grafted periventricular endothelial cells showed widespread distribution in the Gabrb 3$^{ECKO}$ cortex, rescued vascular densities (FIG. 4I), underwent cell proliferation (FIG. 4J), and continued to express GABRB3 and GABA in vivo (FIGS. 4K-M). Immunostaining of grafted interneurons in interneuron-only and interneuron+control endothelial cell co-transplanted brains showed that neurons exhibited limited migration and remained close to the transplantation site with poor migration and distribution (FIGS. 4N, O, T), similar to our observations in the interneuron-only and interneuron+control endothelial cell transplantations in the striatum (FIGS. 3F-I and FIGS. 3P-S). In sharp contrast, interneuron+periventricular endothelial cells co-transplanted brains showed widespread migration of grafted interneurons in the entire cortical area at one-month post-transplantation (FIGS. 4P, Q-T).

Subsequently, we evaluated the impact of the cell transplantation and migration on behavioral function in adult mice of interneuron-only transplanted group, interneuron+control endothelial cell transplanted group and interneuron+periventricular endothelial cell co-transplanted group, one month after transplantation. We compared the results with two groups, Gabrb3$^{ECKO}$ mice and Gabrb3$^{fl/fl}$ mice with sham surgery (FIGS. 5A-E). Gabrb3$^{ECKO}$ mice show poor nest building abilities. Interneuron+periventricular endothelial cell co-transplanted Gabrb3$^{ECKO}$ mice significantly improved their nest building ability and were comparable to sham control mice (FIG. 5A), while interneuron-only Gabrb3$^{ECKO}$ mice and interneuron+control endothelial cell co-transplanted Gabrb3$^{ECKO}$ mice failed to build proper nests (FIG. 5A). Next, we used the tail suspension test to evaluate transplanted and control mice for depressive behavior. When suspended by their tails, normal mice show escape-oriented movements and struggle to face up. Immobility of the mouse was defined as a depressive state when the mouse had given up. Gabrb3$^{ECKO}$ mice showed longer periods of immobility compared to sham control mice (FIG. 5B). Interneuron+periventricular endothelial cell co-transplanted Gabrb3$^{ECKO}$ mice had a significantly lower immobility time, similar to sham controls. In contrast, interneuron-only Gabrb3$^{ECKO}$ mice and interneuron+control endothelial cell co-transplanted Gabrb3$^{ECKO}$ mice continued to show depressive-like behavior and had no significant improvement in immobility time (FIG. 5$b$). Gabrb3$^{ECKO}$ mice showed high levels of anxiety as assessed with the classic light-dark transition test. This test measures the animal's innate preference for dark, enclosed places versus spontaneous exploratory behavior in bright, exposed places. Animals with increased anxiety spend less time in the light and more time in the dark part of the chamber. Interneuron-only Gabrb3$^{ECKO}$ mice and interneurons+control endothelial cell co-transplanted Gabrb3$^{ECKO}$ mice, similar to Gabrb3$^{ECKO}$ mice, showed an aversion to light and preferred to remain in the dark. However, Gabrb3$^{ECKO}$ mice co-transplanted with interneurons and periventricular endothelial cells spent equivalent times in light and dark areas, showing a rescue from increased anxiety-like behavior within one month of grafting (FIG. 5C). High levels of anxiety in Gabrb3$^{ECKO}$ mice also manifested by highly repetitive self-grooming behavior. Interneuron+periventricular endothelial cell co-transplanted Gabrb3$^{ECKO}$ mice showed a significant reduction in self-grooming time compared to Gabrb3$^{ECKO}$ mice, while interneuron-only and interneuron+control endothelial cells transplanted Gabrb3$^{ECKO}$ mice continued to have a long self-grooming time (FIG. 5D). Gabrb3$^{ECKO}$ mice have poor social communication skills. In a three-chamber social communication test, Gabrb3$^{ECKO}$ mice showed no preference for a stranger mouse and spent approximately similar time in investigating stranger mouse versus an inanimate object. Like Gabrb3$^{ECKO}$ mutants, interneuron-only Gabrb3$^{ECKO}$ mice and interneuron+control endothelial cells co-transplanted Gabrb3$^{ECKO}$ mice showed no preference for the stranger mouse (FIG. 5$e$). In contrast, interneuron+periventricular endothelial cells co-transplanted Gabrb3$^{ECKO}$ mice interacted with the stranger mouse for a significantly longer duration than with the inanimate object (FIG. 5E; FIGS. 14A-D).

To confirm that the rescue of behavioral deficits in interneuron+periventricular endothelial cell co-transplanted Gabrb3$^{ECKO}$ mice was due to the dispersion of GABAergic interneurons facilitated by periventricular endothelial cells, and not due to GABA released by periventricular endothelial cells only, we assessed behavioral function of periventricular endothelial cells-only transplanted Gabrb3$^{ECKO}$ mice. Though there was widespread distribution of human periventricular endothelial cells in the cortex, these mice continued to show behavioral deficits that were comparable to the Gabrb3$^{ECKO}$ mice. Periventricular endothelial cell—only transplanted mice continued to show behavioral deficits that was comparable to Gabrb3$^{ECKO}$ mice and interneurons only—Gabrb3$^{ECKO}$ mice. They had poor nest building ability, long immobility time in tail suspension test, high self-grooming time, high exploration time in dark in light-dark box test assay, and poor social interaction ability.

Together, these behavioral assays show that co-transplantation of periventricular endothelial cells and interneurons rescue behavioral deficits of Gabrb3$^{ECKO}$ mice within one month of transplantation, as opposed to interneuron-only, periventricular endothelial cell-only or interneuron+control endothelial cell transplants that do not show a rescue effect during the same duration.

REFERENCES

1. Lewis D A, Levitt P. Schizophrenia as a disorder of neurodevelopment. Annu Rev Neurosci 2002; 25: 409-432.
2. Lewis D A, Hashimoto T, Volk, D W. Cortical inhibitory neurons and schizophrenia. Nat Rev Neurosci 2005; 6: 312-324.
3. Marin, O. Interneuron dysfunction in psychiatric disorders. Nat Rev Neurosci 2012; 13: 107-120.
4. Levitt P, Eagleson K L, Powell E M. Regulation of neocortical interneuron development and the implications for neurodevelopmental disorders. Trends Neurosci 2004; 27: 400-406.
5. Treiman D M. GABAergic mechanisms in epilepsy. Epilepsia 2001; 42 Suppl 3: 8-12.
6. Alvarez-Dolado M, Calcagnotto M E, Karkar K M, Southwell D G, Jones-Davis D M, Estrada R C et al. Cortical inhibition modified by embryonic neural precursors grafted into the postnatal brain. J Neurosci 2006; 26: 7380-7389.
7. Castiglioni V, Onorati M, Rochon C, Cattaneo E. Induced pluripotent stem cell lines from Huntington's disease mice undergo neuronal differentiation while showing alterations in the lysosomal pathway. Neurobiology of disease 2012; 46: 30-40.
8. Bellin M, Marchetto M C, Gage F H, Mummery, C L. Induced pluripotent stem cells: the new patient? Nat Rev Mol Cell Biol 2012; 13: 713-726.
9. Marin O, Rubenstein, J L. A long, remarkable journey: tangential migration in the telencephalon. Nat Rev Neurosci 2001; 2: 780-790.
10. Corbin J G, Nery S, Fishell G. Telencephalic cells take a tangent: non-radial migration in the mammalian forebrain. Nat Neurosci 2001; 4 Sunni: 1177-1182.
11. Wonders C P, Anderson S A. The origin and specification of cortical interneurons. Nat Rev Neurosci 2006; 7: 687-696.
12. Vasudevan A, Long J E, Crandall J E, Rubenstein J L, Bhide P G. Compartment-specific transcription factors orchestrate angiogenesis gradients in the embryonic brain. Nat Neurosci 2008; 11: 429-439.
13. Won C, Lin Z, Kumar T P, Li S, Ding L, Elkhal A, Won C et al. Autonomous vascular networks synchronize GABA neuron migration in the embryonic forebrain. Nat Commun 2013; 4: 2149.
14. Li S, Haigh K, Haigh J J, Vasudevan A. Endothelial VEGF sculpts cortical cytoarchitecture. J Neurosci 2013; 33: 14809-14815.
15. Li S, Kumar T P, Joshee S, Kirschstein T, Subburaju S, Khalili J S et al. Endothelial cell-derived GABA signaling modulates neuronal migration and postnatal behavior. Cell Res 2018; 28: 221-248.

16. Matsui T, Akamatsu W, Nakamura M, Okano H. Regeneration of the damaged central nervous system through reprogramming technology: basic concepts and potential application for cell replacement therapy. Exp Neurol 2014; 260: 12-18.

17. Brennand K J, Simone A, Jou J, Gelboin-Burkhart C, Tran N, Sangar S et al. Modelling schizophrenia using human induced pluripotent stem cells. Nature 2011; 473, 221-225.

18. Lee G, Ramirez C N, Kim H, Zeltner N, Liu B, Radu C et al. Large-scale screening using familial dysautonomia induced pluripotent stem cells identifies compounds that rescue IKBKAP expression. Nat Biotechnol 2012; 30: 1244-1248.

19. Egawa N, Kitaoka S, Tsukita K, Naitoh M, Takahashi K, Yamamoto T et al. Drug screening for ALS using patient-specific induced pluripotent stem cells. Sci Transl Med 2012; 4: 145ra104.

20. Parent J M, Anderson S A. Reprogramming patient-derived cells to study the epilepsies. Nat Neurosci 2015; 18: 360-366.

21. Ardhanareeswaran K, Mariani J, Coppola G, Abyzov A, Vaccarino, F M. Human induced pluripotent stem cells for modelling neurodevelopmental disorders. Nat Rev Neurol 2017; 13, 265-278.

22. Tabar V, Studer L. Pluripotent stem cells in regenerative medicine: challenges and recent progress. Nat Rev Genet 2014; 15, 82-92.

23. Kim T G, Yao R, Monnell T, Cho J H, Vasudevan A, Koh A et al. Efficient specification of interneurons from human pluripotent stem cells by dorsoventral and rostrocaudal modulation. Stem Cells 2014; 32, 1789-1804.

24. Maroof A M, Keros S, Tyson J A, Ying S W, Ganat Y M, Merkle F T et al. Directed differentiation and functional maturation of cortical interneurons from human embryonic stem cells. Cell Stem Cell 2013; 12: 559-572.

25. Nicholas C R, Chen J, Tang Y, Southwell D G, Chalmers N, Vogt D et al. Functional maturation of hPSC-derived forebrain interneurons requires an extended timeline and mimics human neural development. Cell Stem Cell 2013; 12, 573-586.

26. Liu Y, Weick J P, Liu H, Krencik R, Zhang X, Ma L et al. Medial ganglionic eminence-like cells derived from human embryonic stem cells correct learning and memory deficits. Nat Biotechnol 2013; 31: 440-447.

27. Zhu Q, Naegele J R, Chung S. Cortical GABAergic Interneuron/Progenitor Transplantation as a Novel Therapy for Intractable Epilepsy 2018; Front Cell Neurosci 12, 167.

28. Hunt R F, Baraban S C. Interneuron Transplantation as a Treatment for Epilepsy. Cold Spring Harb Perspect Med 2015; 5.

29. Shetty A K, Bates A. Potential of GABA-ergic cell therapy for schizophrenia, neuropathic pain, and Alzheimer's and Parkinson's diseases. Brain Res 2016; 1638: 74-87.

30. Southwell D G, Nicholas C R, Basbaum A I, Stryker M P, Kriegstein A R, Rubenstein J L et al. Interneurons from embryonic development to cell-based therapy. Science 2014; 344: 1240622.

31. Tyson J A, Anderson S A. GABAergic interneuron transplants to study development and treat disease. Trends Neurosci 2014; 37: 169-177.

32. Spatazza J, Mancia Leon W R, Alvarez-Buylla A. Transplantation of GABAergic interneurons for cell-based therapy. Prog Brain Res 2017; 231: 57-85.

33. Cunningham M, Cho J H, Leung A, Savvidis G, Ahn S, Moon M et al. hPSC-derived maturing GABAergic interneurons ameliorate seizures and abnormal behavior in epileptic mice. Cell Stem Cell 2014; 15: 559-573.

34. Upadhya D, Hattiangady B, Castro O W, Shuai B, Kodali M, Attaluri S et al. Human induced pluripotent stem cell-derived MGE cell grafting after status epilepticus attenuates chronic epilepsy and comorbidities via synaptic integration. Proc Natl Acad Sci U S A 2019; 116: 287-296.

35. Alvarez Dolado M, Broccoli V. GABAergic neuronal precursor grafting: implications in brain regeneration and plasticity. Neural plasticity 2011; 2011: 384216.

36. Nolte M W, Loscher W, Herden C, Freed W J, Gernert M. Benefits and risks of intranigral transplantation of GABA-producing cells subsequent to the establishment of kindling-induced seizures. Neurobiology of disease 2008; 31: 342-354.

37. Wichterle H, Garcia-Verdugo J M, Herrera D G, Alvarez-Buylla A. Young neurons from medial ganglionic eminence disperse in adult and embryonic brain. Nat Neurosci 1999; 2: 461-466.

38. Lassiter C M, Gal J S, Becker S, Hartman N W, Grabel L. Embryonic stem cell-derived neural progenitors transplanted to the hippocampus migrate on host vasculature. Stem Cell Res 2016; 16: 579-588.

39. Lippmann E S, Azarin S M, Kay J E, Nessler R A, Wilson H K, Al-Ahmad A et al. Derivation of blood-brain barrier endothelial cells from human pluripotent stem cells. Nat Biotechnol 2012; 30: 783-791.

40. Appelt-Menzel A, Cubukova A, Gunther K, Edenhofer F, Piontek J, Krause G et al. Establishment of a human blood-brain barrier co-culture model mimicking the neurovascular unit using induced pluri- and multipotent stem cells. Stem Cell Reports 2017; 8: 894-906.

41. Ribecco-Lutkiewicz M, Sodja C, Haukenfrers J, Haqqani A S, Ly D, Zachar P et al. A novel human induced pluripotent stem cell blood-brain barrier model: Applicability to study antibody-triggered receptor-mediated transcytosis. Sci Rep 2018; 8: 1873.

42. Li Y, Sun X, Liu H, Huang L, Meng G, Ding Y et al. Development of human in vitro brain-blood barrier model from induced pluripotent stem cell-derived endothelial cells to predict the in vivo permeability of drugs. Neurosci Bull 2019; epub ahead of print 11 May 2019; doi: 10.1007/s12264-019-00384-7.

43. Mansour A A, Gonsalves J T, Bloyd C W, Li H, Fernandes S, Quang D et al. An in vivo model of functional and vascularized human brain organoids. Nat Biotechnol 2018; 36: 432-441.

44. Ritchie M E, Phipson B, Wu D, Hu Y, Law C W, Shi W et al. limma powers differential expression analyses for RNA-sequencing and microarray studies. Nucleic Acids Res 2015; 43: e47.

45. Jiao X, Sherman B T, da. Huang W, Stephens R, Baseler M W, Lane H C et al. DAVID-WS: a stateful web service to facilitate gene/protein list analysis. Bioinformatics 2012; 28: 1805-1806.

46. Hess S E, Rohr S, Dufour B D, Gaskill B N, Pajor E A, Garner J P et al. Home improvement: C57BL/6J mice given more naturalistic nesting materials build better nests. J Am Assoc Lab Anim Sci 2008; 47: 25-31.

47. Silverman J L, Tolu S S, Barkan C L, Crawley J N. Repetitive self-grooming behavior in the BTBR mouse model of autism is blocked by the mGluR5 antagonist MPEP. Neuropsychopharmacology 2010; 35: 976-989.

48. Takao K, Miyakawa, T. Light/dark transition test for mice. J Vis Exp 2006; 104.

49. Can A, Dao D T, Terrillion C E, Piantadosi S C, Bhat S, Gould T D. The tail suspension test. J Vis Exp 2012; e3769.

50. Moy S S, Nadler J J, Perez A, Barbaro R P, Johns J M, Magnuson T R et al. Sociability and preference for social novelty in five inbred strains: an approach to assess autistic-like behavior in mice. Genes Brain Behav 200; 3: 287-302.

51. Livak K J, Schmittgen T D. Analysis of relative gene expression data using real-time quantitative PCR and the 2(-Delta Delta C(T)) Method. Methods 2001; 25: 402-408.

52. Kumar P T, Vasuderan A. Isolation and Culture of Endothelial Cells from the Embryonic Forebrain. J Vis Exp (83), e51021, doi:10.3791/51021 (2014).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of generating a population of human forebrain periventricular endothelial cells, the method comprising:

providing a population of pluripotent stem cells;

(i) culturing the population of pluripotent stem cells in a first, stem cell media comprising Wnt7a protein and gamma amino-butyric acid (GABA), for a first time period sufficient to generate mesodermal cells;

(ii) culturing the mesodermal cells in a second, vascular inducing medium comprising an inhibitor of transforming growth factor beta (TGFβ) signaling, vascular endothelial growth factor-A (VEGF-A), Wnt Family Member 7A (WNT7A), and GABA, for a time sufficient to generate endothelial-like cells;

(iii) culturing the endothelial-like cells in a third, endothelial cell culture medium, comprising growth factors and GABA, for a time sufficient for development of a population of cells comprising CD31⁺ gamma-aminobutyric acid type A receptor subunit beta3 (GABRB3⁺) endothelial cells, and (iv) optionally isolating CD31⁺GABRB3⁺ cells from the mixture, thereby generating a population of human forebrain periventricular endothelial cells.

2. The method of claim 1, wherein the population of pluripotent stem cells comprise human embryonic stem cells or induced pluripotent stem cells (iPSC), optionally wherein the iPSC express one organic cation/carnitine transporter 4 (OCT4) and/or TRA1-60.

3. The method of claim 1, wherein the first, stem cell media comprises E8 media with one or more growth factors; bone morphogenetic protein 4 (BMP4); Activin A; and a small molecule activator of wingless (WNT) signaling.

4. The method of claim 3, wherein the growth factors comprise Fibroblast growth factor 2 (FGF2) and either TGFβ or nodal growth differentiation factor (NODAL).

5. The method of claim 3, wherein the small molecule activator of WNT signaling is a compound selected from the group consisting of CHIR-98023; CHIR-99021; CHIR-99030; Hymenialdisine; debromohymeialdisine; dibromo-cantherelline; Meridianine A; alsterpaullone; cazapaullone; Aloisine A; NSC 693868; (1H-Pyrazolo[3,4-b]quinoxalin-3-amine); Indirubin-3'-oxime; (Indirubin-3'-monoxime; 3-[1,3-Dihydro-3-(hydroxyimino)-2H-indol-2-ylidene]-1,3-dihydro-2H-indol-2-one); A 1070722; (1-(7-Methoxyquino-lin-4-yl)-3-[6-(trifluoromethyl) pyridin-2-yl]urea); L803; L803-mts; TDZD8; NP00111; HMK-32; Manzamine A; Palinurin; Tricantin; IM-12; (3-(4-Fluorophenylethyl-amino)-1-methyl-4-(2-methyl-1H-indol-3-yl)-1H-pyrrole-2, 5-dione); NP031112; NP00111; NP031115; VP 2.51; VP2.54; VP 3.16; and VP 3.35.

6. The method of claim 1, wherein the inhibitor of TGFβ signaling is a small molecule inhibitor of TGF-β/Smad signaling pathway.

7. The method of claim 1, wherein the endothelial-like cells express CD31 and von Willebrand Factor (vWF).

8. The method of claim 1, wherein the growth factors in the third, endothelial cell culture medium comprise VEGF and FGF2.

9. The method of claim 8, wherein the cells in the population of human forebrain perivascular endothelial cells express one or more periventricular endothelial cell markers selected from the group consisting of GABRB3, GABA, NK2 homeobox (NKX2.1), paired box 6 (PAX6), and ISL LIM homeobox 1 (ISL1).

10. The method of claim 1, further comprising maintaining the purified CD31⁺GABRB3⁺ cells in endothelial cell culture medium comprising growth factors and GABA.

11. The method of claim 1, wherein the concentration of GABA in the first and second media is 1-10 uM.

12. The method of claim 5, wherein the small molecule activator of WNT signaling is CHIR99021.

13. The method of claim 6, wherein the inhibitor of TGFβ signaling is SB431542.

14. The method of claim 11, wherein the concentration of GABA in the first and second media is 5 uM.

* * * * *